(12) United States Patent
Shahbazian et al.

(10) Patent No.: US 10,913,981 B2
(45) Date of Patent: *Feb. 9, 2021

(54) REAGENTS AND METHODS FOR SEQUENCING

(71) Applicant: Life Technologies Corporation, Carlsbad, CA (US)

(72) Inventors: Mona Shahbazian, Martinez, CA (US); Kara Norman, San Diego, CA (US); Aron Lau, San Leandro, CA (US); Nakul Nataraj, Davis, CA (US)

(73) Assignee: Life Technologies Corporation, Carlsbad, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 16/427,782

(22) Filed: May 31, 2019

(65) Prior Publication Data

US 2019/0284632 A1 Sep. 19, 2019

Related U.S. Application Data

(63) Continuation of application No. 14/461,306, filed on Aug. 15, 2014, now Pat. No. 10,364,465.

(60) Provisional application No. 61/903,268, filed on Nov. 12, 2013.

(51) Int. Cl.
| | | |
|---|---|---|
| C12N 15/11 | (2006.01) |
| C12Q 1/6883 | (2018.01) |
| C12Q 1/6869 | (2018.01) |
| C12Q 1/6876 | (2018.01) |

(52) U.S. Cl.
CPC ......... *C12Q 1/6883* (2013.01); *C12Q 1/6869* (2013.01); *C12Q 1/6876* (2013.01); *C12N 15/11* (2013.01); *C12Q 2600/156* (2013.01); *C12Q 2600/16* (2013.01); *C12Q 2600/166* (2013.01)

(58) Field of Classification Search
CPC .. C12Q 1/6883; C12Q 1/6869; C12Q 1/6876; C12N 15/11
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 5,035,996 | A | 7/1991 | Hartley |
| 5,854,033 | A | 12/1998 | Lizardi |
| 6,797,470 | B2 | 9/2004 | Barany et al. |
| RE39,007 | E | 3/2006 | Dattagupta et al. |
| 10,364,465 | B2 * | 7/2019 | Shahbazian .......... C12Q 1/6869 |
| 2004/0265897 | A1 | 12/2004 | Lizardi |
| 2010/0121582 | A1 | 5/2010 | Pan et al. |
| 2012/0277112 | A1 | 11/2012 | Linn et al. |

FOREIGN PATENT DOCUMENTS

| | | |
|---|---|---|
| WO | WO 1994/016108 A1 | 7/1994 |
| WO | WO 2000/050632 A2 | 8/2000 |
| WO | WO 2006/081222 A2 | 8/2006 |
| WO | WO 2006/087574 A2 | 8/2006 |
| WO | WO 2010/057650 A1 | 5/2010 |

OTHER PUBLICATIONS

Rome et al.; "Anatomic Barriers Influence the Distribution of In Vivo Gene Transfer Into the Arterial Wall"; Arteriosclerosis, Thrombosis, and Vascular Biology; vol. 14 No. 1; Jan. 1994; p. 148-161.
European Patent Application No. 14802752.7; Office Action—Article 94(3); dated Jan. 11, 2018; 4 pages.
Communication European Patent Application No. 14761917.5 (dated Mar. 21, 2017 5 pages).
Spinella et al. Tandem Arrayed Ligation of Expressed Sequence Tags (TALEST): A New Method For Generating Global Gene Expression Profiles, Nucleic Acids Research, 27 (1999) 1-8.
Powers et al. Efficient and accurate whole genome assembly and methylome profiling of *E. coli*, BMC Genomics, 14 (2013) 675 (1-18).
International Preliminary Report on Patentability issued in International Patent Application No. PCT/US2014/051373 (dated May 17, 2016, 5 pages).
Communication issued in European Patent Application No. 14761917.5 (dated Jul. 21, 2016 2 pages).
"Next-generation Sequencing: Standardization of Clinical Testing (Nes-StoCT) Workgroup Principles and Guidelines", Nature Biotechnology: Assuring the Quality of Next-Generation Sequencing in Clinical Laboratory Practice: Supplemental Guidelines, vol. 30 (doi:10.1038/nbt.2403), Nov. 8, 2012, 1-64.
Bullard, J. et al., "Evaluation of statistical methods for normalization and differential expression in mRNA-Seq experiments", BMC Bioinformatics, vol. 11 (94), 2010, 1-13.
Frampton, G. et al., "Development and validation of a clinical cancer genomic profiling test based on massively parallel DNA sequencing", Nature Biotechnology, http://www.nature.com/nbt/journal/vaop/ncurrent/full/nbt.2696.html, Oct. 20, 2013, 1-22.
Illumina, "Using a PhiX Control for HiSeq Sequencing Runs: A low-concentration spike-in of Illumina PhiX Control v3 provides quality and calibration controls", Technical Note: Seguencing, Mar. 21, 2013, 2 Pages.
Jiang, L. et al., "Synthetic spike-in standards for RNA-seq experiments", Genome Research, vol. 21, Aug. 4, 2011, 1543-1551.
Life Technologies Corporation, "AcroMetrix Oncology Hotspot Control", Catalog No. 969056, Document No. MAN0010820, 2014, 5 Pages.
PCT/US2014/051373, "International Search Report and Written Opinion dated Nov. 25, 2014", dated Nov. 25, 2014, 11 Pages.
Rehm, H. et al., "ACMG clinical laboratory standards for next-generation sequencing", ACMG Practice Guidelines: Genetics in Medicine, Jul. 25, 2013, 1-15.
Lewin, Gene Expression, vol. 2, John Wiley & Sons, London, 1974, pp. 156-165.

(Continued)

*Primary Examiner* — James Martinell
(74) *Attorney, Agent, or Firm* — BakerHostetler

(57) ABSTRACT

The disclosure provides a plurality of nucleic acid sequences comprising multiple variants of a reference sequence. The disclosure further provides plasmids, cells, methods and kits comprising the same.

18 Claims, 11 Drawing Sheets

Specification includes a Sequence Listing.

(56) References Cited

OTHER PUBLICATIONS

Bellon et al.; "External Quality Assessment for KRAS Testing Is Needed: Setup of a European Program and Report of the First Joined Regional Quality Assessment Rounds"; The Oncologist; vol. 16; 2011; p. 467-478.

Gargis et al.; "Assuring the quality of next-generation sequencing in clinical laboratory practice"; Nature Biotechnology; vol. 30, 2012; p. 1033-1036.

Rehm et al.; "ACMG clinical laboratory standards for next-generation sequencing"; Genetics in Medicine; vol. 15; 2013; p. 733-747.

Tang et al.; "Characterization of a recurrent 3.8 kb deletion involving exons 17a and 17b within the CFTR gene"; Journal of Cystic Fibrosis; vol. 12; 2013; p. 290-294.

Wu et al.; "The Ligation Amplification Reaction (LAR)—Amplification of Specific DNA Sequences Using Sequential Rounds of Template-Dependent Ligation"; Genomics 4; 1989; p. 560-569.

F. Barany; "Genetic disease detection and DNA amplification using cloned thermostable ligase"; Proceedings of the Nat'l Acad. Of Sciences; vol. 88; Jan. 1991; p. 189-193.

Lizardi et al.; "Mutation detection and single-molecule counting using isothermal rolling-circle amplification"; Nature Genetics; vol. 19; 1998; p. 225-232.

Baner et al.; "Signal amplification of padlock probes by rolling circle replication"; Nucleic Acids Research; vol. 26; 1998; p. 5073-5078.

Little et al.; "Strand Displacement Amplification and Homogeneous Real-Time Detection Incorporated in a Second-Generation DNA Probe System, BDProbeTecET"; Clinical Chemistry; vol. 45; 1999; p. 777-784.

Kegg Pathyway Database; https://www.genome.jp.kegg/pathway/html; Jul. 2019; accessed Jul. 25, 2019; 11 pages.

* cited by examiner

SEQUENCE LISTING

<160> NUMBER OF SEQ ID NOS: 33

<210> SEQ ID NO 1
<211> LENGTH: 8
<212> TYPE: DNA
<213> ORGANISM: Homo sapiens

<400> SEQUENCE: 1 ccaagctc                                                                                8

<210> SEQ ID NO 2
<211> LENGTH: 10
<212> TYPE: DNA
<213> ORGANISM: Homo sapiens

<400> SEQUENCE: 2
aggatcttga                                                                             10

<210> SEQ ID NO 3
<211> LENGTH: 10
<212> TYPE: DNA
<213> ORGANISM: Homo sapiens

<400> SEQUENCE: 3
aactgaattc                                                                             10

<210> SEQ ID NO 4
<211> LENGTH: 6
<212> TYPE: DNA
<213> ORGANISM: Homo sapiens

<400> SEQUENCE: 4 aaaaag                                                                                  6

<210> SEQ ID NO 5
<211> LENGTH: 10
<212> TYPE: DNA
<213> ORGANISM: Artificial Sequence
<220> FEATURE:
<223> OTHER INFORMATION: Synthetic fragment

<400> SEQUENCE: 5
atcaaagtgc                                                                             10

<210> SEQ ID NO 6
<211> LENGTH: 8
<212> TYPE: DNA
<213> ORGANISM: Artificial Sequence
<220> FEATURE:
<223> OTHER INFORMATION: Synthetic fragment

<400> SEQUENCE: 6 ccaatctc                                                                                8

<210> SEQ ID NO 7
<211> LENGTH: 10
<212> TYPE: DNA
<213> ORGANISM: Artificial Sequence
<220> FEATURE:
<223> OTHER INFORMATION: Synthetic fragment

<400> SEQUENCE: 7
aggaacttga                                                                             10

```
<210> SEQ ID NO 8
<211> LENGTH: 10
<212> TYPE: DNA
<213> ORGANISM: Artificial Sequence
<220> FEATURE:
<223> OTHER INFORMATION: Synthetic fragment

<400> SEQUENCE: 8
aactcaattc                                                              10

<210> SEQ ID NO 9
<211> LENGTH: 6
<212> TYPE: DNA
<213> ORGANISM: Artificial Sequence
<220> FEATURE:
<223> OTHER INFORMATION: Synthetic fragment

<400> SEQUENCE: 9 ataaag                                                                   6

<210> SEQ ID NO 10
<211> LENGTH: 10
<212> TYPE: DNA
<213> ORGANISM: Artificial Sequence
<220> FEATURE:
<223> OTHER INFORMATION: Synthetic fragment

<400> SEQUENCE: 10
atgaaagtgc                                                              10

<210> SEQ ID NO 11
<211> LENGTH: 18
<212> TYPE: DNA
<213> ORGANISM: Homo sapiens

<400> SEQUENCE: 11 ggggggggttt tccccccc                                                    18

<210> SEQ ID NO 12
<211> LENGTH: 20
<212> TYPE: DNA
<213> ORGANISM: Homo sapiens

<400> SEQUENCE: 12
ggggggggga accccccccc                                                   20

<210> SEQ ID NO 13
<211> LENGTH: 6
<212> TYPE: DNA
<213> ORGANISM: Artificial Sequence
<220> FEATURE:
<223> OTHER INFORMATION: Synthetic fragment

<400> SEQUENCE: 13 gggggg                                                                   6

<210> SEQ ID NO 14
<211> LENGTH: 6
<212> TYPE: DNA
<213> ORGANISM: Artificial Sequence
<220> FEATURE:
<223> OTHER INFORMATION: Synthetic fragment

<400> SEQUENCE: 14 gggggа                                                                   6
```

```
<210> SEQ ID NO 15
<211> LENGTH: 6
<212> TYPE: DNA
<213> ORGANISM: Artificial Sequence
<220> FEATURE:
<223> OTHER INFORMATION: Synthetic fragment

<400> SEQUENCE: 15 ggggaa                                                                    6

<210> SEQ ID NO 16
<211> LENGTH: 6
<212> TYPE: DNA
<213> ORGANISM: Artificial Sequence
<220> FEATURE:
<223> OTHER INFORMATION: Synthetic fragment

<400> SEQUENCE: 16 gggaaa                                                                    6

<210> SEQ ID NO 17
<211> LENGTH: 6
<212> TYPE: DNA
<213> ORGANISM: Artificial Sequence
<220> FEATURE:
<223> OTHER INFORMATION: Synthetic fragment

<400> SEQUENCE: 17 ggaaaa                                                                    6

<210> SEQ ID NO 18
<211> LENGTH: 6
<212> TYPE: DNA
<213> ORGANISM: Artificial Sequence
<220> FEATURE:
<223> OTHER INFORMATION: Synthetic fragment

<400> SEQUENCE: 18 gaaaaa                                                                    6

<210> SEQ ID NO 19
<211> LENGTH: 16
<212> TYPE: DNA
<213> ORGANISM: Artificial Sequence
<220> FEATURE:
<223> OTHER INFORMATION: Synthetic fragment

<400> SEQUENCE: 19
gcccagatgg acatga                                                        16

<210> SEQ ID NO 20
<211> LENGTH: 26
<212> TYPE: DNA
<213> ORGANISM: Artificial Sequence
<220> FEATURE:
<223> OTHER INFORMATION: Synthetic fragment

<400> SEQUENCE: 20
acttcctcct cctccataca ggaaac                                             26

<210> SEQ ID NO 21
<211> LENGTH: 42
<212> TYPE: DNA
<213> ORGANISM: Artificial Sequence
<220> FEATURE:
<223> OTHER INFORMATION: Synthetic fragment
```

<400> SEQUENCE: 21
ctataagaaa gagataacag cgcatattat gatttaattt tt                                42

<210> SEQ ID NO 22
<211> LENGTH: 32
<212> TYPE: DNA
<213> ORGANISM: Artificial Sequence
<220> FEATURE:
<223> OTHER INFORMATION: Synthetic fragment

<400> SEQUENCE: 22
tgatcatatt catattctct gaaatcaacg ag                                          32

<210> SEQ ID NO 23
<211> LENGTH: 31
<212> TYPE: DNA
<213> ORGANISM: Artificial Sequence
<220> FEATURE:
<223> OTHER INFORMATION: Synthetic fragment

<400> SEQUENCE: 23
ctcgttgatt tcagagaata tgaatatgat c                                           31

<210> SEQ ID NO 24
<211> LENGTH: 10
<212> TYPE: DNA
<213> ORGANISM: Artificial Sequence
<220> FEATURE:
<223> OTHER INFORMATION: Synthetic fragment

<400> SEQUENCE: 24
cactgcttga                                                                   10

<210> SEQ ID NO 25
<211> LENGTH: 16
<212> TYPE: DNA
<213> ORGANISM: Artificial Sequence
<220> FEATURE:
<223> OTHER INFORMATION: Synthetic fragment

<400> SEQUENCE: 25
aggaattaag agaagc                                                            16

<210> SEQ ID NO 26
<211> LENGTH: 13
<212> TYPE: DNA
<213> ORGANISM: Artificial Sequence
<220> FEATURE:
<223> OTHER INFORMATION: Synthetic fragment

<400> SEQUENCE: 26
gaaaaaacaa gga                                                               13

<210> SEQ ID NO 27
<211> LENGTH: 42
<212> TYPE: DNA
<213> ORGANISM: Artificial Sequence
<220> FEATURE:
<223> OTHER INFORMATION: Synthetic fragment

<400> SEQUENCE: 27
taataacata taaagtaaaa ctaaaaagtc aacataaata ta                               42

<210> SEQ ID NO 28

```
<211> LENGTH: 13
<212> TYPE: DNA
<213> ORGANISM: Artificial Sequence
<220> FEATURE:
<223> OTHER INFORMATION: Synthetic fragment

<400> SEQUENCE: 28
gagctgtgcc gca                                                        13

<210> SEQ ID NO 29
<211> LENGTH: 14
<212> TYPE: DNA
<213> ORGANISM: Artificial Sequence
<220> FEATURE:
<223> OTHER INFORMATION: Synthetic fragment

<400> SEQUENCE: 29
tagaacatat catc                                                       14

<210> SEQ ID NO 30
<211> LENGTH: 22
<212> TYPE: DNA
<213> ORGANISM: Artificial Sequence
<220> FEATURE:
<223> OTHER INFORMATION: Synthetic fragment

<400> SEQUENCE: 30
gatcatattc atattctctg aa                                              22

<210> SEQ ID NO 31
<211> LENGTH: 21
<212> TYPE: DNA
<213> ORGANISM: Artificial Sequence
<220> FEATURE:
<223> OTHER INFORMATION: Synthetic fragment

<400> SEQUENCE: 31
ttcagagaat atgaatatga t                                               21

<210> SEQ ID NO 32
<211> LENGTH: 31
<212> TYPE: DNA
<213> ORGANISM: Artificial Sequence
<220> FEATURE:
<223> OTHER INFORMATION: Synthetic fragment

<400> SEQUENCE: 32
ggtgtgatta cagtcaaaag gcctctacgg t                                    31

<210> SEQ ID NO 33
<211> LENGTH: 13
<212> TYPE: DNA
<213> ORGANISM: Artificial Sequence
<220> FEATURE:
<223> OTHER INFORMATION: Synthetic fragment

<400> SEQUENCE: 33
agcatacgtg atg                                                        13
```

REAGENTS AND METHODS FOR SEQUENCING

CROSS-REFERENCE TO RELATED APPLICATIONS

This application is a continuation of application Ser. No. 14/461,306, filed Aug. 15, 2014, which claims priority to U.S. provisional application No. 61/903,268, filed Nov. 12, 2013, all of which are incorporated herein by reference in their entirety.

SEQUENCE LISTING

The instant application contains a Sequence Listing, which has been submitted electronically in ASCII format and is hereby incorporated by reference in its entirety. The Sequence Listing, labeled "059545.000016_SequenceListing_May2019_ST25.txt," was created on May 30, 2019, and is 7 KB.

BACKGROUND OF THE INVENTION

A significant challenge facing testing laboratories is quality control. Some reports have indicated that mutations in cancer genes were correctly identified by only 70% of testing laboratories (Bellon, et al. External Quality Assessment for KRAS Testing Is Needed: Setup of a European Program and Report of the First Joined Regional Quality Assessment Rounds. *Oncologist.* 2011 April; 16(4): 467-478). Questions have been raised regarding how to monitor next generation sequencing and assays as well as the concordance of variant calls across multiple platforms, library preparation methods, and bioinformatic pipelines. Compositions and methods providing a flexible, single reagent representing a large number of genetic variants are desired by those of ordinary skill in the art and are described herein.

SUMMARY OF THE INVENTION

The disclosure provides compositions, controls, plasmids, cells, methods and kits comprising nucleic acid molecules.

In one embodiment, a nucleic acid molecule comprising multiple variants of a reference is disclosed. In other embodiments, a mixture or combination of nucleic acid molecules comprising variants of the reference sequence are disclosed.

In certain embodiments, the nucleic acid molecule or mixture of nucleic acid molecules comprise one or more variants present at a high or low-frequency.

In certain embodiments, the disclosure provides a control reagent comprising multiple nucleic acid molecules.

In yet another embodiment, a kit comprising at least one nucleic acid molecule or mixture of nucleic acid molecules comprising variants is disclosed In another embodiment, a method for confirming the validity of a sequencing reaction is disclosed. The method comprises including a known number of representative sequences and/or variants thereof in a mixture comprising a test sample potentially comprising a test nucleic acid sequence, and sequencing the nucleic acids in the mixture, wherein detection of all of the representative sequences and/or variants in the mixture indicates the sequencing reaction was accurate.

The disclosure also provides a composition comprising multiple nucleic acid species wherein the nucleic acid sequence of each species differs from its neighbor species by a predetermined percentage.

In certain embodiments, a method is provided that comprises sequencing a nucleic acid species in order to calibrate a sequencing instrument.

In yet other embodiments, the disclosure provides plasmids and cells encoding the nucleic acids or mixture of nucleic acids disclosed herein.

The disclosure also provides a plasmid and/or a cell comprising multiple nucleic acid species wherein the nucleic acid sequence of each species differs from its neighbor species by a predetermined percentage.

The disclosure further provides a frequency ladder. The frequency ladder comprises a plurality of variants at different frequencies.

DETAILED DESCRIPTION OF THE INVENTION

Figure 1:
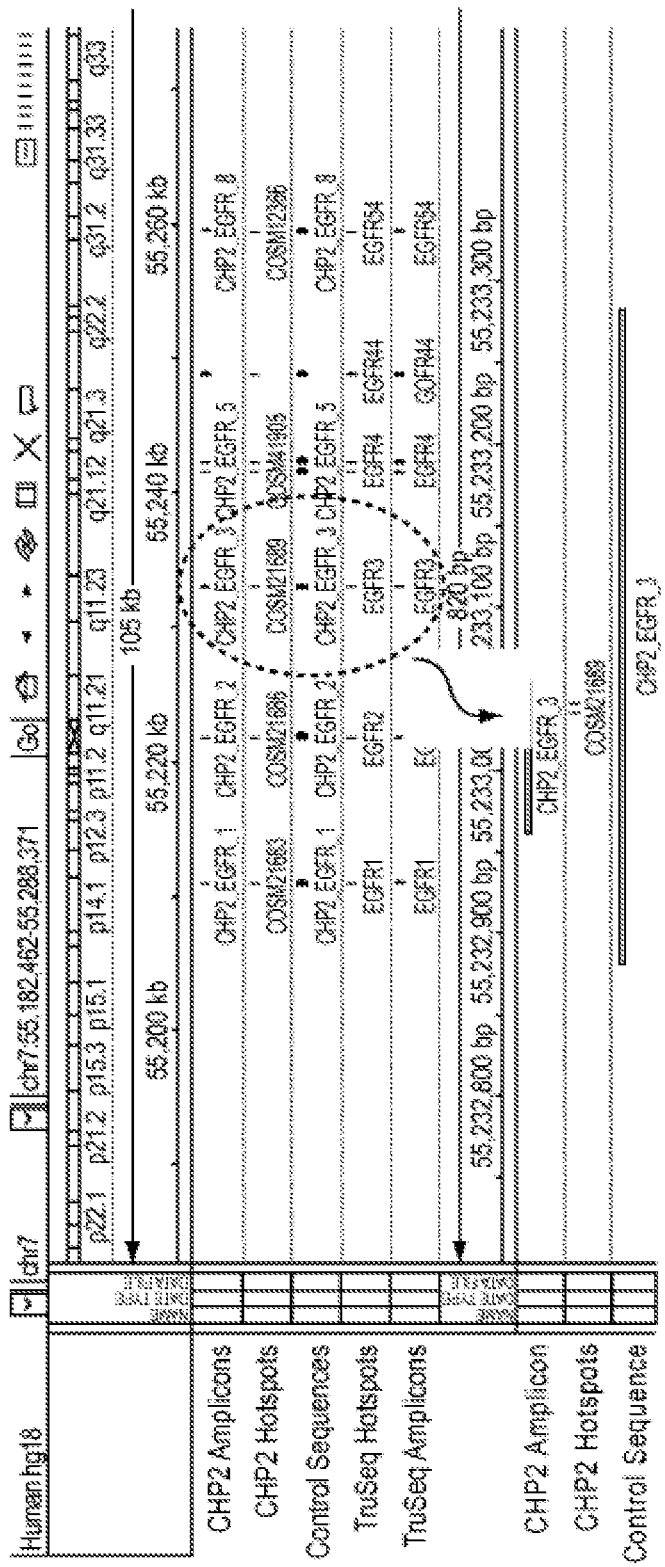
FIG. 1. Exemplary EGFR amplicon selection.

Provided herein are compositions, methods, kits, plasmids, and cells comprising nucleic acid reference sequences and variants of a reference sequence. The compositions disclosed herein have a variety of uses, including but not limited to, assay optimization, validation, and calibration; peer-to-peer comparison; training and PT/EQA, QC monitoring, reagent QC, and system installation assessment.

There is a recognized need in the market for flexible, reliable control materials for NGS testing (see Assuring the Next Quality of Next-Generation Sequencing in Clinical Laboratory Practice; Next Generation Sequencing: Standardization of Clinical Testing (Nex-SToCT) Working group Principles and Guidelines, Nature Biotechnology, doi: 10.1038/nbt.2403; and ACMG Clinical laboratory standards for next generation sequencing, *American College of Medical Genetics and Genomics*,doi: 10.1038/gim.2013.92). This disclosure provides such control materials.

This disclosure relates to control reagents representing reference sequences and/or variants thereof (e.g., mutations) that may be used for various purposes such as, for instance, assay validation/quality control in sequencing reactions (e.g., next generation sequencing (NGS) assays). Traditional metrics used to characterize the quality of a sequencing reaction include, for instance, read length, minimum quality scores, percent target-mapped reads, percent pathogen-specific reads, percent unique reads, coverage levels, uniformity, percent of non-covered targeted bases and/or real-time error rate. Parameters that may affect quality include, for instance, the types and/or number of analytes being monitored (e.g., the types and number of polymorphisms (single or multiple nucleotide polymorphisms (SNPs, MNPs)), insertions and/or deletions, amplicons, assay contexts and/or limits of detection), sample type (e.g., mammalian cells, infectious organism, sample source), commutability (e.g., validation across multiple technology platforms and/or types of screening panels being utilized), sample preparation (e.g., library preparation type/quality and/or type of sequencing reaction (e.g., run conditions, sequence context)), and/or other parameters. Those of ordinary skill in the art realize, for instance, that the quality of such reactions may vary between laboratories due to subtle differences in guidelines, the metrics and parameters mentioned above, the reference standards used, and the fact that many NGS technologies are highly complex and evolving. This disclosure provides quality control reagents that may be used in different laboratories, under different conditions, with different types of samples, and/or across various technology platforms to confirm that that assays are being carried out correctly and that results from different laboratories may be reliably compared to one another (e.g, that each is of suitable quality). In some embodiments, the problem of confirming the quality of a sequencing reaction is solved using a multiplex control comprising multiple nucleic acid fragments, each representing a different variant of a reference sequence.

In certain embodiments, a control reagent for use in sequencing reactions is provided. The control reagent may comprise one or more components that may be used alone or combined to assess the quality of a particular reaction. For instance, some assays are carried out to identify genetic variants present within a biological sample. The control reagents described herein may also provide users with the ability to compare results between laboratories, across technology platforms, and/or with different sample types. For instance, in some embodiments, the control reagent may represent a large number of low percentage (e.g., low frequency) variants of different cancer-related genes that could be used to detect many low percentage variants in a single assay and/or confirm the reliability of an assay. The control reagent could be used to generate numerous data points to compare reactions (e.g., run-to-run comparisons). The control reagent may be used to determine the reproducibility of variant detection over time across multiple variables. The control reagent may be used to assess the quality of a sequencing run (i.e., that the instrument has sufficient sensitivity to detect the included variants at the given frequencies). The control reagent may also be used to differentiate between a proficient and a non-proficient user by comparing their sequencing runs, and/or to differentiate the quality of reagents between different lots. The control reagent may also aid in assay validation studies, as many variants are combined in one sample material. This obviates the need for multiple samples containing one or two variants each, and greatly shortens the work and time required to validate the assay.

The control reagent typically comprises one or more nucleic acid (e.g., DNA, RNA, circular RNA, hairpin DNA and/or RNA) fragments containing a defined reference sequence of a reference genome (defined as chromosome and nucleotide range) and/or one or more variants of the reference sequence. The source material for the variants may be genomic DNA, synthetic DNA, and combinations thereof. A variant typically includes nucleotide sequence variations relative to the reference sequence. The variant and reference sequence typically share at least 50% or about 75-100% (e.g., any of about 75, 76, 77, 78, 79, 80, 81, 82, 83, 84, 85, 86, 87, 88, 89, 90, 91, 92, 93, 94, 95, 96, 97, 98, 99%) sequence identity. In some embodiments, however, the identity shared may be significantly less where, for example, the variant represents a deletion or insertion mutation (either of which may be up to several kilobases or more). An exemplary deletion may be, for instance, recurrent 3.8 kb deletion involving exons 17a and 17b within the CFTR gene as described by Tang, et al. (J. Cystic Fibrosis, 12(3): 290-294 (2013) (describing a c.2988+1616_c.3367+356de13796ins62 change, flanked by a pair of perfectly inverted repeats of 32 nucleotides)). In some embodiments, variants may include at least one of a single nucleotide polymorphism (SNP), one or more multiple nucleotide polymorphism(s) (MNV), insertion(s), deletion(s), copy number variation(s), gene fusion(s), duplication(s), inversion(s), repeat polymorphism(s), homopolymer(s), non-human sequence(s), or any combination thereof. Such variants (which may include by reference any combinations) may be included in a control reagent as part of the same or different components. The reference sequence(s) and/or variants may be arranged within a control reagent as cassettes.

Cassettes contains a reference sequence or variant adjoined and/or operably linked to one or more restriction enzyme site(s), sequencing primer(s) site, and/or hairpin-forming site(s). In some embodiments, it may be useful to include different types of sequences adjacent to each cassette; for instance, it may be useful to design one cassette to be adjacent to a restriction enzyme and/or a hairpin sequence. Doing so may help prevent problems such as cross-amplification between adjacent fragments/cassettes. As such, each reference sequence and/or variant may be releasable and/or detectable separate from any other reference sequence and/or variant. The typical cassette may be about 400 bp in length but may vary between 50-20,000 bp (e.g., such as about any of 50, 100, 200, 300, 400, 500, 600, 700, 800, 900, 1000, 2000, 3000, 4000, 5000, 6000, 7000, 800, 900, 1000, 2500, 5000, 7500, 10000, 12500, 15000, 17500, or 20000 bp). Each control reagent may comprise one or more cassettes, each representing one or more reference sequence(s) and/or variant(s) (e.g., each being referred to as a "control sequence"). Each reference sequence and/or variant may be present in a control sequence and/or control reagent at percentage of about any of 0.1% to 100% (e.g., about any 0.1, 0.2, 0.3, 0.4, 0.5, 0.6, 0.7, 0.8, 0.9, 1, 2.5, 5, 7.5, 10, 15, 20, 25, 30, 35, 40, 45, 50, 55, 60, 65, 70, 75, 80, 85, 90, 95, or 100%). For instance, a control sequence or control reagent that is 100% reference sequence or variant would be a reagent representing only one reference sequence or variant. Similarly, a control sequence or control reagent comprising 50% of a variant would be a control reagent representing only up to two reference sequences and/or variants. The remaining percentage could consist of other sequences such as control sequences and the like.

In certain embodiments a T7 or other promoter can be present upstream of each cassette. This allows for massively parallel transcription of many gene regions. This technique facilitates construction of a control containing equivalent amounts of each target sequence. When there are equivalent amounts of many targets, ease of use of the control is increased. For example, contamination in a control in a patient sample would be easier to detect because all transcripts would show up in the contaminated sample. It is highly unlikely for patient samples to contain, e.g., a large number of fusion transcripts, such an assay result would signal the user that that a contamination issue is present. This is in contrast to a situation in which only one transcript is present at a much higher abundance in a contaminated sample—which could lead to the contaminant being mistaken for a true positive signal. The ability to construct a control with equivalent amounts of each target sequence eliminates the potential for this type of error.

In certain embodiments, the reference sequence(s) and/or variants may be adjoined and/or operably linked to one or more different restriction enzyme sites, sequencing primer site(s), and/or hairpin-forming sites. As described above, certain designs may be used to prevent problems such as cross-amplification between reference sequences and/or variants. In some embodiments, the control sequences and/or cassettes may optionally be arranged such that the same are releasable from the control reagent. This may be accomplished by, for instance, including restriction enzyme (RE) sites at either end of the control sequence. A control reagent may therefore be arranged as follows: RE site/control sequence/RE site. The RE sites may be the same and/or different from one another. The RE sites in one cassette may also be the same and/or different to those present in any other cassette. As such, the control sequences may be released from the cassette as desired by the user by treating the control sequence with one or more particular restriction enzymes.

In some embodiments, the control reagent may comprise multiple components that may be used together. In certain embodiments, the multiple components comprise a first and a second component which may be plasmids comprising different control sequences and/or different arrangements of the same control sequences. Thus, the components may represent the same or different reference sequences and/or variants. Such components may be used together as a panel, for instance, such that a variety of reference sequences and/or variants may be assayed together. Where the reference sequences and/or variants are the same, each component may include those variants in different cassette arrangements and/or forms. In some embodiments, the multiple components may comprise a first component representing one or more SNP variants and a second component representing one or more multiple nucleotide polymorphism(s), insertion(s), deletion(s), copy number variation(s), gene fusion(s), duplication(s), inversion(s), repeat polymorphism(s), homopolymer(s), and/or non-human sequence(s). The components may be the same or different types of nucleic acids such as plasmids, with each comprising the same or different variants of one or more reference sequences arranged as described herein or as may be otherwise determined to be appropriate by one of ordinary skill in the art. In some embodiments, different types of plasmids may be combined to provide a multi-component control reagent representing many different reference sequences and/or variants.

Plasmids can be quantified by any known means. In one embodiment, quantitation of each plasmid is performed using a non-human 'xeno' digital PCR target sequence. The exact copy number of the plasmid is determined. The exact copy number of genomic DNA is also determined (obtained by quantification of genomic target site(s)). With this information, controls can be accuratley and reproducibly developed that contain all targets/variants within a tight frequency range.

The variants may be contained within the control reagent as DNA fragments, each containing a defined sequence derived from a reference genome (defined as chromosome and nucleotide range) with one or more variations (e.g., nucleotide differences) introduced into the fragment. A variant may be, for instance, a sequence having one or more nucleotide sequence differences from the defined sequence (e.g., a reference sequence). For instance, an exemplary reference sequence may comprise "hostpots" suitable for modification. Such hotspots may represent nucleotides and/or positions in a reference sequence that occur in nature (e.g., mutations observed in cancer cells). One or more of such hotspots may be modified by changing one or more nucleotides therein to produce a control sequence (or portion thereof) that may be incorporated into a control reagent. For example, modification of the exemplary epidermal growth factor receptor (EGFR) Ex19 reference sequence to produce control sequences (Hotspots 1, 2, 3, 4, 5) is shown below (see also, FIG. 1):

Wild Type (e.g., EGFR Ex19) CCAAGCTC (SEQ ID NO: 1) . . . AGGATCTTGA (SEQ ID NO: 2) . . . AACTGAATTC (SEQ ID NO: 3) . . . AAAAAG (SEQ ID NO: 4) . . . ATCAAAGTGC (SEQ ID NO: 5) (400 bp)

Hotspot ID 1 CCAA<u>T</u>CTC (SEQ ID NO: 6) . . . AGGATCTTGA (SEQ ID NO: 2) . . . AACTGAATTC (SEQ ID NO: 3) . . . AAAAAG (SEQ ID NO: 4) . . . ATCAAAGTGC (SEQ ID NO: 5)

Control Sequence Contains Multiple Hotspots

CCAA<u>T</u>CTC (SEQ ID NO: 6; HOTSPOT ID 1) . . . AGGA<u>A</u>CTTGA (SEQ ID NO: 7; HOTSPOT ID 2) . . . AACT<u>C</u>AATTC (SEQ ID NO: 8; HOTSPOT ID 3) . . . A<u>T</u>AAAG (SEQ ID NO: 9; HOTSPOT ID 4) . . . AT<u>G</u>AAAGTGC (SEQ ID NO: 10; HOTSPOT ID 5). This exemplary control sequence thereby represents multiple EGFR variants (e.g., Hotspot IDs 1, 2, 3, 4, 5, etc.) A control reagent may comprise multiple control sequences, each representing one or more variants of the same or different reference sequences. Any number of variants may be represented by a control sequence, and any number of control sequences may be included in a control reagent. A control reagent may comprise, for instance, a number of variants such that the all possible variants of a particular reference sequence are represented by a single control reagent. For instance, the control reagent may comprise multiple SNPs, MNPs, deletions, insertions and the like, each representing a different variant of the reference sequence. Additional, exemplary, non-limiting variants are shown in Tables 1A and 1B and Table 6.

Control reagents may also be designed to represent multiple types of control sequences. For instance, control reagents may be designed that represent multiple types of reference sequences and/or variants thereof (which may be found in control sequences alone or in combination). Exemplary categories of control sequences for which the control reagents described herein could have relevance include not only the aforementioned cancer-related areas but also fields of inherited disease, microbiology (e.g., with respect to antibiotic resistance mutations, immune-escape related mutations), agriculture (e.g. plant microbe and/or drug resistance-related mutations), livestock (e.g., mutations related to particular livestock traits), food and water testing, and other areas. Exemplary combinations (e.g., panels) of cancer-related reference sequences that may be represented by a particular control reagent (or combinations thereof) are shown in Table 2.

The control reagents and methods for using the same described herein may provide consistent control materials for training, proficiency testing and quality control monitoring. For instance, the control reagents may be used to confirm that an assay is functioning properly by including a specific number of representative sequences and/or variants thereof that should be detected in an assay and then calculating the number that were actually detected. This is exemplified by the data presented in Table 3:

As illustrated in Table 3, a "bad run" is identified where the number of variants detected does not match the number of variants expected to be detected (e.g., included in the assay). As shown in the exemplary assay of Table 3, if a particular control reagent (or combination thereof) used in an assay includes 15 representative sequences and/or variants thereof, all 15 should be detected if the assay is properly carried out. If less than 15 of these control sequences are not detected, the assay is identified as inaccurate (e.g., a "Bad Run"). If all 15 of the sequences are detected, the assay is identified as accurate (e.g., a "Good Run"). Variations of this concept are also contemplated herein, as would be understood by those of ordinary skill in the art.

In certain embodiments, the control reagent may be prepared by mixing variant DNA fragments (e.g., as may be incorporated into a plasmid) with genomic DNA or synthesized DNA comprising "wild-type" (e.g., non-variant) sequence. Such sequence may be obtained from or present in control cells (e.g., naturally occurring or engineered/cultured cell lines). In some embodiments, the wild-type sequence may be included on a DNA fragment along with the variant sequence, or the variant sequences may be transfected into and/or mixed with cells (e.g., control cells). In certain embodiments, such mixtures may be used to prepare formalin-fixed, paraffin-embedded (FFPE) samples (e.g., control FFPE samples), for example. For instance, in some embodiments, the control reagent may be prepared and tested by designing a control sequence (e.g., an amplicon) comprising a representative sequence and/or variant thereof; designing restriction sites to surround each amplicon; synthesizing a nucleic acid molecule comprising a cassette comprising the amplicon and the restriction sites; and, incorporating the cassette into a plasmid backbone. The construct may then be tested by sequencing it alone (e.g, providing an expected frequency of 100%) or after mixing the same with, for example, genomic DNA at particular expected frequencies (e.g., 50%). Such constructs may also be mixed with cells for various uses, including as FFPE controls.

In certain embodiments, the control reagents described herein can also be used to provide a frequency ladder. A frequency ladder is composed of many variants at different frequencies. In some embodiments, the control reagent could be used to provide an "ladder" in, for example, 5% increments of abundance (e.g., about any of 1, 5, 10, 15, 20, 25, 30, 35, 40, 45, 50, 55, 60, 65, 70, 75, 80, 85, 90, 95, or 100% abundance). For example, the ladder could be constructed by taking a single sample with many different variants present at high (e.g., 80% allele frequency) and making dilutions down to low frequencies. Alternatively, the ladder could be a single sample containing variants at different frequencies. The ladder could be used as a reference for many sample types, including somatic variants at low abundance (e.g., tumor single nucleotide polymorphisms), or germline variants present at, as a non-limiting example, about 50% abundance. Such a ladder may also be used to determine instrument limits of detection for many different variants at the same time. This saves users time in finding materials containing one to a few variants and resources for testing because all variants are present in a single sample rather than many. An example is provided in Table 8:

As shown in Table 8, a ladder was constructed by diluting a sample containing 555 variants starting at approximately 50% frequency down to ~3% frequency. The ladder was tested in duplicate using the Ion AMPLISEQ® Cancer Hotspot Panel v2 using the Ion Torrent PERSONAL GENOME MACHINE® (PGM). The frequencies for 35 of the variants are reported for each sample tested. The shaded cells indicate that the variant was not detected. Such data could be used to establish the limit of detection for each variant.

Figure 2:
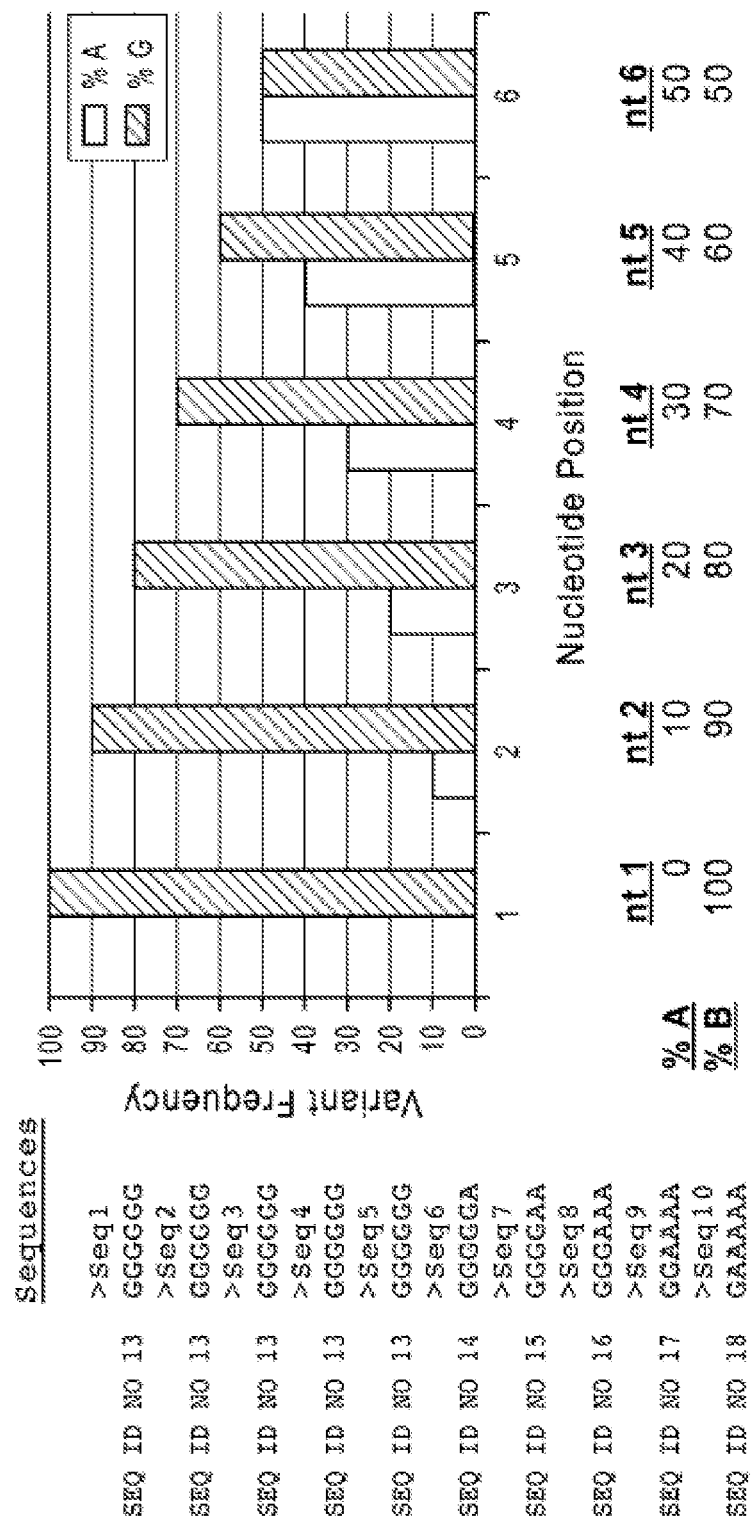
FIG. 2 is a graph showing variant frequency at each nucleotide position as well as percentage A and G content. Sequences 1-5 are the same and are used to dilute out sequences 6-10. Each sequence is found in its own cassette, and all cassettes are found in the same plasmid. This design provides an absolute truth—e.g., there is 10% sequence 6 in this design. In contrast to mixing with genomic sequence, this provides the most precision when making a 10% mix. This could be used to calibrate assays.
Figure 3:
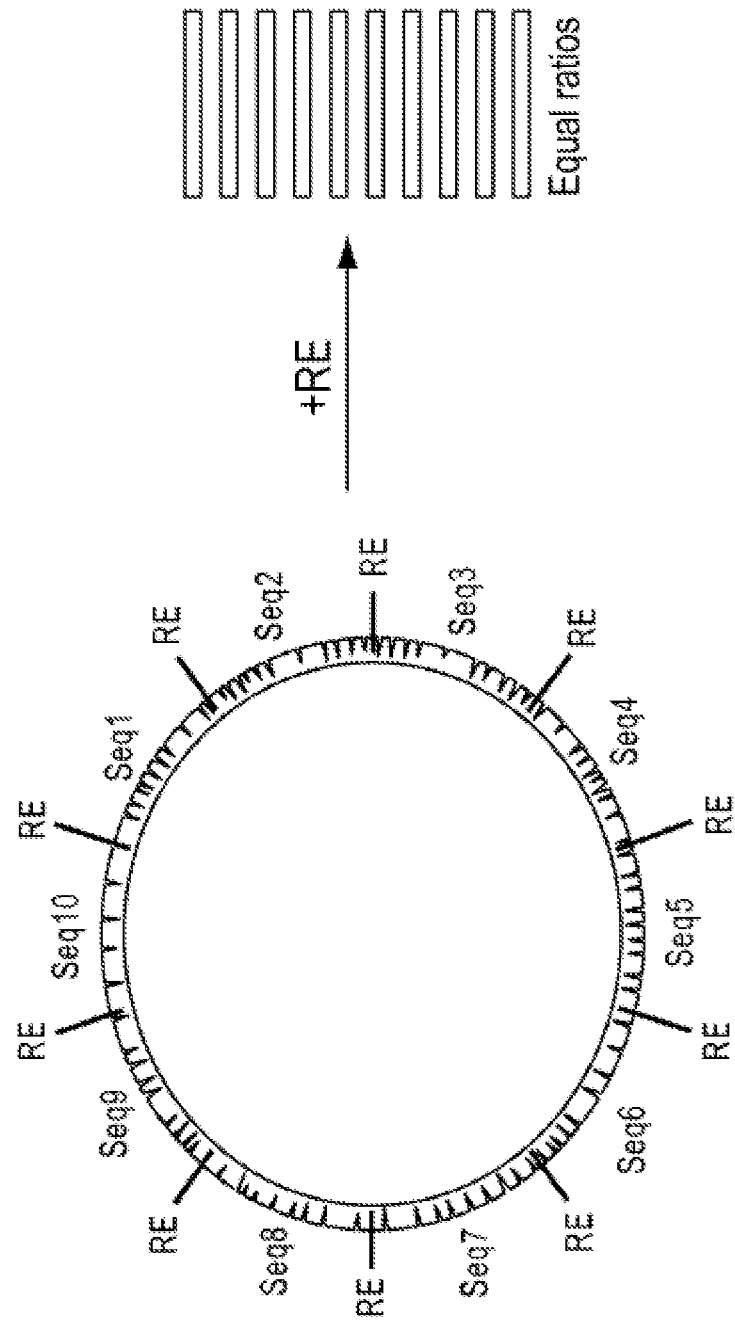
FIG. 3 is a schematic of an exemplary plasmid with 10 sequences and restriction sites, leading to equal ratios of each sequence.
Figure 4:
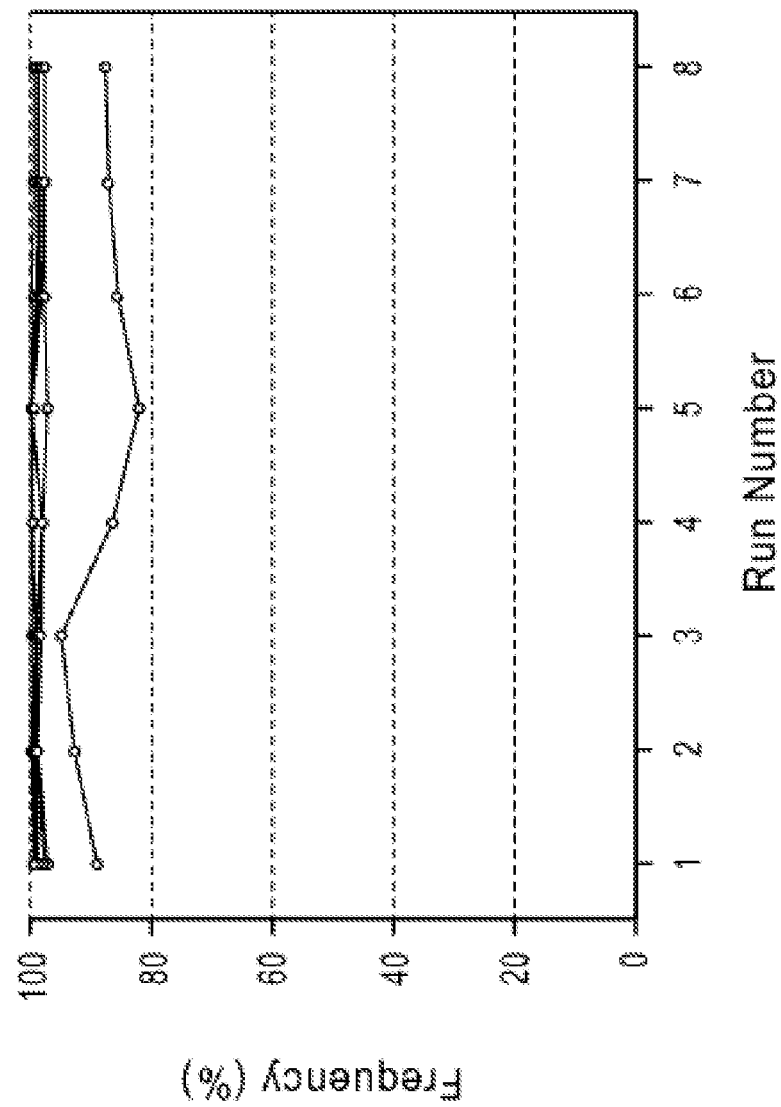
FIG. 4 is a graph showing the frequency percentage per run comprising Panel A (FLT3, PDGFRA, FGFR3, CSF1R, EGFR, HRAS, and TP53).
Figure 5:
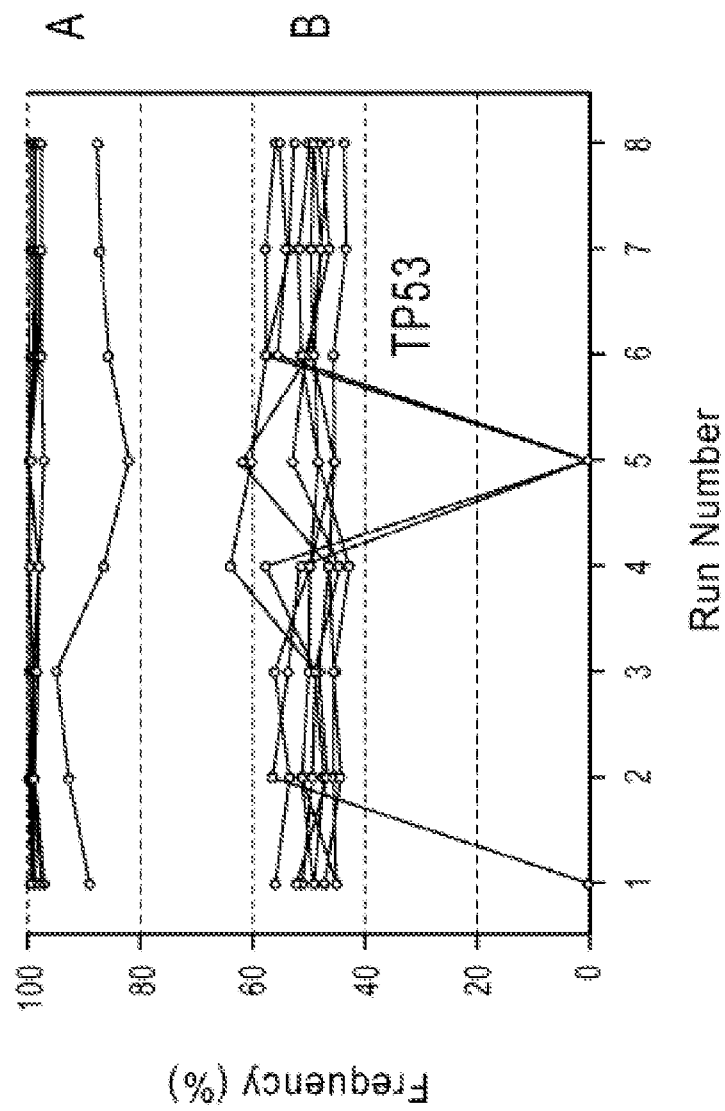
FIG. 5 is a graph showing the frequency percentage per run of Panel A and Panel B (TP53, PIK3CA, GNA11, VHL, FBXW7, RET, HNF1A, and STK11)
Figure 6:
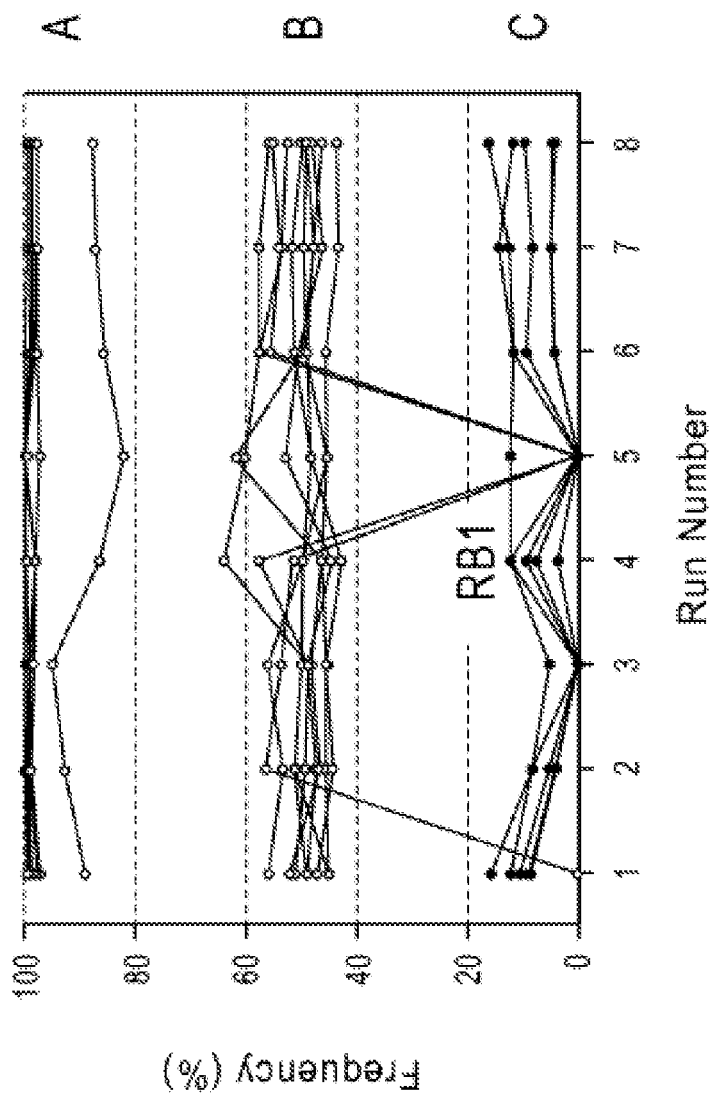
FIG. 6 is a graph showing the frequency percentage per run of Panel A, Panel B, and Panel C (RB1, EGFR, ABL1, ERBB2, and ATM).
Figure 7:
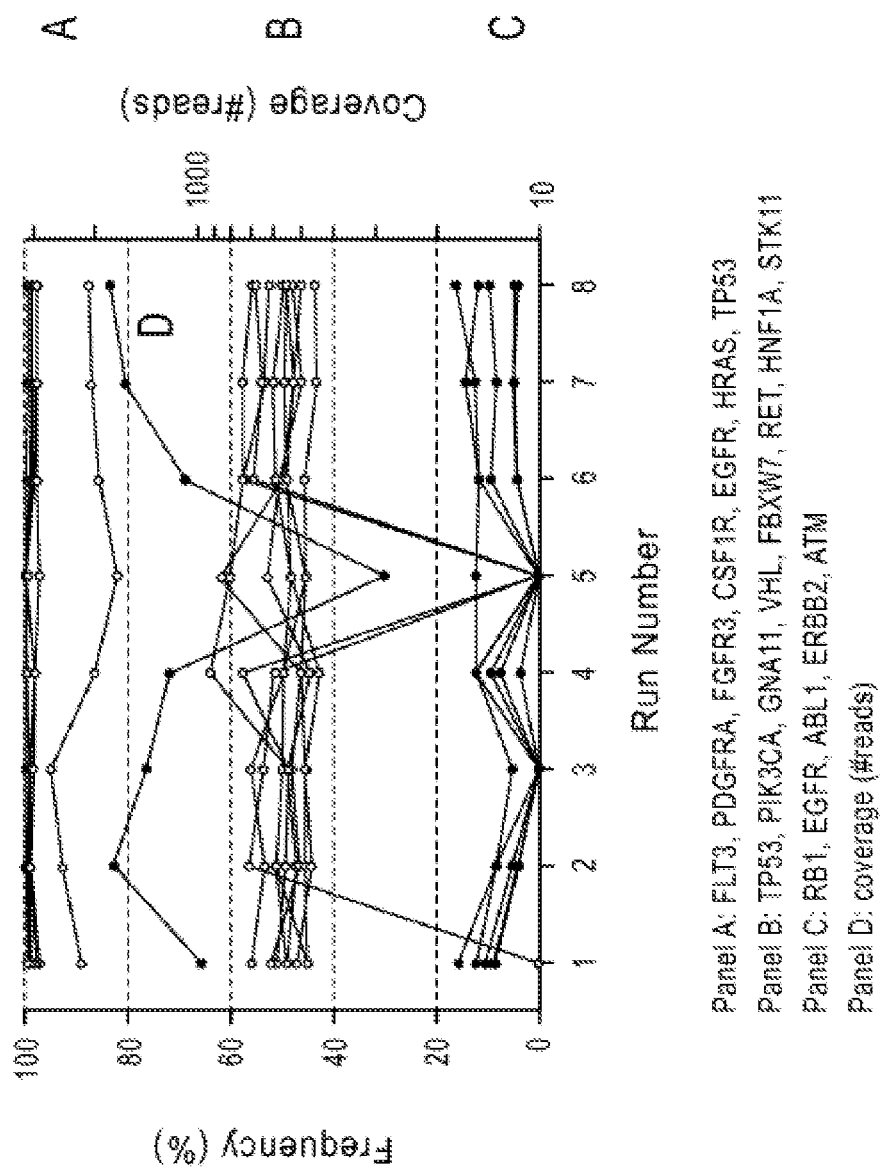
FIG. 7 is a graph showing the frequency percentage per run of Panel A, Panel B, Panel C, and Line D, which represents the number of reads (i.e., coverage)

The ladder could be used across many platforms, including Sanger sequencing and next generation platforms, and both RUO and IVD applications could benefit from use of this standard. The frequency ladder could also serve as internal controls in sequencing reactions, much like the 1 kb DNA ladder serves as a reference in almost every agarose gel. As an example, one design would provide five unique and five identical sequences as shown in FIGS. 2 and 3. As shown therein, in one sequence position, there is a variant present in only one of these ten sequences. At a second position, the variant is present in two of the ten sequences. At the third position, the variant is present in three of the sequences, and so on. This would yield variants at 10% frequency increments from 0-100%. This is a simplified example and random intervening sequences may be necessary to prevent sequencing artifacts. The product could take any suitable form such as an oligonucleotide (e.g., PCR fragment or synthetic oligonucleotide), plasmids, or one plasmid with concatenated sequences separated by identical restriction enzyme sites (FIG. 3). An advantage of having all sequence variants on one plasmid is that the relative levels of all ten sequences within a mixture would be well controlled; during manufacturing, the plasmid could be cleaved between each sequence with the same enzyme, giving rise to ten fragments at equal ratios. As would be understood by those of ordinary skill in the art, derivations of such a ladder could include different variant types (e.g., insertions and/or deletions), every nucleotide change could be incorporated into the design (e.g., A→C, A→T, etc.), and/or smaller increments could provide fine-tuned measurement at abundances lower than 10%. For instance, a second plasmid with other mutations could be added to the initial plasmid at a one to nine ratio, yielding variants at even lower frequencies. Such a low frequency sequencing ladder could be an essential control when measuring somatic mutations that appear, for example, at <10% abundance. In some embodiments, such a sequencing ladder may comprise multiple nucleic acid species wherein the nucleic acid sequence of each species differs from its neighbor species by a predetermined percentage (e.g., about any of 1, 2, 3, 4, 5, 6, 7, 8, 9, 10% or more). Each species may comprise, for instance, any suitable number of nucleotides (e.g., about any of 5, 10, 20, 40, 50, 60, 70, 80, 90, 100, 125, 150, 175, 200, 225, 250, 275, 300, 325, 350, 375, 400, 425, 450, 475, or 500). Each species may also comprise a homopolymer sequence of at least 3 nucleotides. In some embodiments, the nucleic acid of the species is DNA, and these may be encoded on vectors such as plasmids and/or by and/or within cells. In some embodiments, each species may comprise a nucleic acid bar code that may be unique to each species. Methods comprising sequencing the nucleic acid species to calibrate a sequencing instrument, to obtain data for sequencing instrument development work, including algorithm development, base calling, variant calling, and/or verify that an instrument is functioning properly (e.g., IQ/OQ/PQ) are also contemplated.

One of ordinary skill in the art would understand that the control reagents described herein are broadly useful in a variety of sequencing systems and/or platforms. For instance, the control reagents described herein may be used in any type of sequencing procedure including but not limited to Ion Torrent semiconductor sequencing, Illumina MISEQ®, capillary electrophoresis, microsphere-based systems (e.g., Luminex), Roche 454 system, DNA replication-based systems (e.g., SMRT by Pacific Biosciences), nanoball- and/or probe-anchor ligation-based systems (Complete Genomics), nanopore-based systems and/or any other suitable system.

One of ordinary skill in the art would also understand that the control reagents described herein are broadly useful in a variety of nucleic acid amplification-based systems and/or platforms. The control reagents described herein may used in and/or with any in vitro system for multiplying the copies of a target sequence of nucleic acid, as may be ascertained by one of ordinary skill in the art. Such systems may include, for instance, linear, logarithmic, and/or any other amplification method including both polymerase-mediated amplification reactions (such as polymerase chain reaction (PCR), helicase-dependent amplification (HDA), recombinase-polymerase amplification (RPA), and rolling chain amplification (RCA)), as well as ligase-mediated amplification reactions (such as ligase detection reaction (LDR), ligase chain reaction (LCR), and gap-versions of each), and combinations of nucleic acid amplification reactions such as LDR and PCR (see, for example, U.S. Pat. No. 6,797,470). Such systems and/or platforms may therefore include, for instance, PCR (U.S. Pat. Nos. 4,683,202; 4,683,195; 4,965,188; and/or 5,035,996), isothermal procedures (using one or more RNA polymerases (see, e.g., PCT Publication No. WO 2006/081222)), strand displacement (see, e.g., U.S. Pat. No. RE39007E), partial destruction of primer molecules (see, e.g., PCT Publication No. WO 2006/087574)), ligase chain reaction (LCR) (see, e.g., Wu, et al., Genomics 4: 560-569 (1990)), and/or Barany, et al. Proc. Natl. Acad. Sci. USA 88:189-193 (1991)), Qβ RNA replicase systems (see, e.g., PCT Publication No. WO 1994/016108), RNA transcription-based systems (e.g., TAS, 3SR), rolling circle amplification (RCA) (see, e.g., U.S. Pat. No. 5,854,033; U.S. Patent Application Publication No. 2004/265897; Lizardi et al. Nat. Genet. 19: 225-232 (1998); and/or Bailer et al. Nucleic Acid Res., 26: 5073-5078 (1998)), and/or strand displacement amplification (SDA) (Little, et al. Clin. Chem. 45:777-784 (1999)), among others. These systems, along with the many other systems available to the skilled artisan, may be suitable for use with the control reagents described herein.

In one embodiment, a control reagent may be designed and tested using one or more of the steps below:

designing a control sequence (e.g., an amplicon) comprising a representative sequence of a particular gene of interest and/or variants thereof (e.g., those targeted by commercially-available NGS tests such as the AMPLISEQ Cancer Hotspot Panel v2, and/or the TRUSEQ Amplicon Cancer Panel);

identifying sequence from a genome reference source (e.g., Genome Reference Consortium Human Reference 37 (GRCh37)) encompassing the amplicon;

designing a cassette comprising an ~400 bp sequence comprising the amplicon surrounded by (e.g., 5' and 3') the genomic sequence identified in step b);

designing restriction sites to surround each cassette prepared in step c) (e.g., where one version may additionally include sequences that create a hairpin when the DNA is single-stranded);

synthesizing a nucleic acid molecule comprising the cassette of step c) and restriction sites of step d) using a common vector (e.g., pUC57) (e.g., "plasmid V1");

preparing a second plasmid (e.g., "plasmid V2") comprising multiple fragments of the gene of interest (and/or variants thereof) with a hairpin structure and a restriction site between each region;

optionally, linearizing the variant sequences contained within plasmids V1 and/or V2 with a restriction enzyme;

mixing the variants with genomic DNA (e.g., wild-type gDNA) at a particular expected variant frequency (e.g., approximately 50%);

optionally, testing the "variant sequence" alone (e.g., providing an expected variant frequency of 100%);

performing variant detection using NGS.

In certain embodiment, individual cassettes can be synthesized for all genes of interest and combined with wild type. In certain embodiments, a cassette can be designed with a plurality of variants, which do not interfere with the detection of variants near or adjacent thereto.

In some embodiments, NGS may be performed using the Ion Personal Genome Machine (PGM) by first constructing libraries following the user manuals for the Ion AMPLISEQ® Library Preparation Manual with AMPLISEQ® Cancer Hotspot Panel v2 reagents; preparing template-positive Ion sphere particles (ISPs) and enriching the same using the Ion OneTouch2 instrument following the Ion PGM Template OT2 200 Kit Manual; sequencing using the Ion PGM Sequencing 200 Kit v2 Manual or Sequencing on the Illumina MISEQ® following the TRUSEQ® Amplicon Cancer Panel user manual or the Illumina MiSeq® user manual; and, performing data analysis for PGM using the Torrent Variant Caller v3.4 and v3.6, and for MISEQ® using the MISEQ® Reporter v2.3).

The reagents and methods described herein may be used in a variety of settings with a variety of samples. For instance, these reagents and methods may be used to analyze biological samples such as serum, whole blood, saliva, tissue, urine, dried blood on filter paper (e.g, for newborn screening), nasal samples, stool samples or the like obtained from a patient and/or preparations thereof (e.g., FFPE preparations). In some embodiments, control preparations comprising the control reagents described herein may be provided.

This disclosure further relates to kits comprising one or more control reagents described herein. The kits may be used to carry out the methods described herein or others available to those of ordinary skill in the art along with, optionally, instructions for use. A kit may include, for instance, control sequence(s) including multiple reference sequences and/or variations thereof in the form of, for instance, one or more plasmids. In some embodiments, the kit may contain a combination of control sequences organized to provide controls for many variations of one or more reference sequences. In some embodiments, the variations may relate to an oncogene that is diagnostic for a particular cancer. In some embodiments, for instance, the kit may comprise control reagents and/or control samples (e.g., tissue samples) known to cover the breadth of mutations known for a particular cancer. In some embodiments, the variations of the marker are variations of a mutation in a gene that are prognostic for the usefulness of treating with a drug. In some embodiments, the marker or markers are for a particular disease and/or a variety of diseases (e.g., cancer, infectious disease). In some embodiments, the control reagent(s) may be included in a test to ascertain the efficacy of a drug in testing for the presence of a disease and/or progression thereof. In some embodiments, the kit may comprise control reagents for testing for a series of diseases that have common characteristics and/or symptoms (e.g., related diseases). In some embodiments, the marker may have unknown significance but may otherwise be of interest to the user (e.g., for basic research purposes). The kit may also include a container (e.g., vial, test tube, flask, bottle, syringe or other packaging system (e.g., include injection or blow-molded plastic containers) into which one or more control reagents may be placed/contained, and in some embodiments, aliquoted). Where more than one component is included in the kit, it will generally include at least one second, third or other additional container into which the additional components can be separately placed. Various combinations of components may also be packaged in a single container. The kits may also include reagent containers in close confinement for commercial sale. When the components of the kit are provided in one and/or more liquid solutions, the liquid solution comprises an aqueous solution that may be a sterile aqueous solution. As mentioned above, the kit may also include instructions for employing the kit components as well as the use of any other reagent not included in the kit. Instructions may include variations that may optionally be implemented. The instructions may be provided as a separate part of the kit (e.g., a paper or plastic insert or attachment) or as an internet-based application. In some embodiments, the kit may control reagents relating to between any number of reference sequences and/or variants thereof which may be detected alone or in combination with one another (e.g., a multiplex assay). In some embodiments, the kit may also comprise at least one other sample containing a defined amount of control reagent and "control" test cell admixed such that the same may provide a reference point for the user. Kits may further comprise one or more of a polymerase and/or one or more oligonucleotide primers. Other variations and arrangements for the kits of this disclosure are contemplated as would be understood by those of ordinary skill in the art.

Thus, in some embodiments, the disclosure provides a nucleic acid molecule or mixture of nucleic acid molecules comprising multiple variants of a reference sequence, each variant sequence may optionally be releasable from the nucleic acid molecule. In certain embodiments, the nucleic acid molecule or mixture of nucleic acid molecules comprises variants releasable from the nucleic acid molecule using a restriction enzyme.

In some embodiments, the nucleic acid molecule or mixture of nucleic acid molecules comprises at least one single nucleotide polymorphism (SNP), multiple nucleotide polymorphisms (MNP), insertion, deletion, copy number variation, gene fusion, duplication, inversion, repeat polymorphism, homopolymer of a reference sequence, and/or a non-human sequence. In some embodiments, the nucleic acid molecule or mixture of nucleic acid molecules comprises at least 5 variants. In certain embodiments, at least 15, 20, 30, 50, 100, 200, 300 400, 700, 1000 variants are present. In yet other embodiments, greater than 1000 variants are present. In some embodiments, each variant is present (e.g., in the sample being tested) at a high or low-frequency. For instance, in certain embodiments, each variant may be present at a frequency of 1%, 5%, 10%, 15%, 20%, 30%, 40% or 50% or more. In other embodiments, each variant may be present at a frequency of less than 50%, less than 40%, less than 20%, less than 15%, less than 10%, less than 5%, less than 3%, less than 1%, less than 0.5%, less than 0.1%, and any integer in between.

An advantage of the disclosed control materials is that the "truth" of a sample is known. There are currently no reference materials for which absolute frequency (i.e, the truth) is known, that is, the actual frequency of a given variant or combination of variants present are not known. In contrast, in the disclosed control materials, the actual frequency of variants is known.

Attendant to the teachings of this disclosure, standardized control materials for next generation sequencing (NGS) assays can be produced. Issues such as variant call differences between sites, variability of reagents across instruments, variation introduced by diverse bioinformatics pipelines and filters, run-to-run and lab-to-lab variability can be identified and resolved and/or obviated utilizing the control materials.

A further advantage is that the control materials disclosed herein can comprise any number and type of variants, including insertions and deletions of differing lengths, large numbers of SNPs, etc. No other control material exists that provide such diversity.

The variants can be any of interest. There is no limit provided herein with respect to the type and number of variants that can be utilized in the current disclosure.

In certain embodiments, modified nucleotides can be utilized as variants. In certain embodiments, methylation can be detected. For example, CpG methylation can be utilized as a biomarker variant.

This disclosure also provides reagents and methods for confirming the validity of a sequencing reaction by including a known number of representative sequences and/or variants thereof in a mixture comprising a test sample potentially comprising a test nucleic acid sequence and sequencing the nucleic acids in the mixture, wherein detection of all of the representative sequences and/or variants in the mixture indicates the sequencing reaction was accurate. The representative sequences and/or variants may be of the type described herein. Compositions comprising the same are also provided. The pre-determined percentage may be, for instance, about 1, 5 or 10%. And each species may be from, for instance, 20-500 nucleotides. Each species may comprise a homopolymer sequence of at least 3 nucleotides. The nucleic acids may be DNA. Each species may possess a nucleic acid barcode that may be unique to each species. The nucleic acid species described herein may be used to calibrate a sequencing instrument, for instance. Kits comprising such species, optionally further comprising one or more polymerases and/or one or more oligonucleotide primers are also provided. Plasmids and/or cells comprising multiple nucleic acid species wherein the nucleic acid sequence of each species differs from its neighbor species by a predetermined percentage are also provided.

It is to be understood that the descriptions of this disclosure are exemplary and explanatory only and are not intended to limit the scope of the current teachings. In this application, the use of the singular includes the plural unless specifically stated otherwise. Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y". Whenever a range of values is provided herein, the range is meant to include the starting value and the ending value and any value or value range therebetween unless otherwise specifically stated. For example, "from 0.2 to 0.5" may mean 0.2, 0.3, 0.4, and 0.5; ranges therebetween such as 0.2-0.3, 0.3-0.4, 0.2-0.4; increments there between such as 0.25, 0.35, 0.225, 0.335, 0.49; increment ranges there between such as 0.26-0.39; and the like. The term "about" or "approximately" may refer the ordinary meaning of the term but may also indicate a value or values within about any of 1-10 percent of the listed value.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art. Certain embodiments are further described in the following examples. These embodiments are provided as examples only and are not intended to limit the scope of the claims in any way.

Aspects of this disclosure may be further understood in light of the following examples, which should not be construed as limiting the scope of the disclosure in any way.

EXAMPLES

Example 1

An exemplary control reagent was prepared and tested as described below:

a) amplicons were designed comprising the fragments shown in Tables 1-3;

b) genomic sequences were selected to encompass each amplicon (the selected genomic sequences being the chromosome and nucleotide positions of the reference genome corresponding to the 5' nucleotide of the forward and reverse primers for each amplicon and all the sequence between these two nucleotides);

c) a cassette was designed comprising an ~400 bp EGFR sequence comprising the amplicon surrounded by (e.g., 5' and 3') the genomic sequence identified in step b) (the reference sequence is added in roughly equally amounts to each end of the region defined in step b) to comprise a ~400 bp region);

d) restriction enzyme and other sites were designed to each cassette prepared in step c) (e.g., where one version may additionally include sequences that create a hairpin when the DNA is single-stranded; the restriction enzymes being chosen such that the sequences of interest are not digested but simply released from the control reagent) as shown below:

EGFR V1**

**EGFR_1, etc. represent EGFR variants; restriction enzyme sites for ClaI, HindIII, SmaI, XhoI and Not I enzymes were positioned between variants.
EGFR_1-ClaI-EGFR_2-HindIII-EGFR_3-SmaI-EGFR_4-XhoI-EGFR_5-NotI-EGFR_6/7-EGFR_8

EGFR V2***

***Hairpin 7 (HP(7)): GGGGGGGTTTTCCCCCCC (SEQ ID NO: 11); HindIII=HindIII RE site;
EGFR_4-HP(7)-ClaI-EGFR_5-HP(7)-HindIII-EGFR_6/7-HP(9)-Sma1-EGFR_8
Hairpin 9 (HP(9)): GGGGGGGGGAACCCCCCCCC (SEQ ID NO: 12); SmaI=SmaI RE site e) the cassette of step d) was incorporated into a common vector (pUC57) (e.g., plasmid V1) by automated synthesis of oligonucleotides on solid-phase synthesizers followed by ligation of overlapping oligonucleotides;

f) a second plasmid (e.g., "plasmid V2") comprising multiple fragments of the gene of interest (and/or variants thereof) with a hairpin structure and a restriction site between each region (e.g., as in exemplary construct EGFR V2 above and Table 4) was also prepared by automated synthesis of oligonucleotides on solid-phase synthesizers followed by ligation of overlapping oligonucleotides;

g) the variant sequences (Tables 4-6) contained within plasmids V1 and/or V2 were then linearized HindIII;

h) the variants were then mixed with genomic DNA (e.g., wild-type gDNA) at a particular expected variant frequency (e.g., approximately 50%) (plasmid DNA and human embryonic kidney (HEK-293) genomic DNA were quantified using a fluorometer (QUBIT®) to determine the concentration; plasmid and genomic DNA were then mixed together to obtain a 1:1 molecular ratio (50% variant frequency));

i) the "variant sequences" were then tested alone to provide an expected variant frequency of 100%) to confirm sequencing; and, j) variants of step h) were detected by NGS using the Ion Personal Genome Machine (PGM) and Illumina MiSeq (results are presented in Table 7).

Example 2

FFPE-Embedded Controls

The results of monitoring assays using FFPE-embedded controls are presented in FIGS. 4-7. As shown therein, FFPE-embedded control reagents may be used to monitor variant detection, including low frequency variants (e.g., RB1 as indicated by "C" in the figures). Variants may be tracked by the amplicon per se, GC content, sequence context, and/or variant type as desired by those of ordinary skill in the art.

Each embodiment disclosed herein may be used or otherwise combined with any of the other embodiments disclosed. Any element of any embodiment may be used in any embodiment. Although the invention has been described with reference to specific embodiments, it will be understood by those skilled in the art that various changes may be made and equivalents may be substituted for elements thereof without departing from the true spirit and scope of the invention. In addition, modification may be made without departing from the essential teachings of the invention.

Example 3

555-Variant Control Performance Across Multiple Test Sites

A control sample was constructed that contained 555 variants from 53 different genes and tested with the Ion AMPLISEQ® Cancer Hotspot Panel v2 (CHPv2), TRUSEQ® Amplicon Cancer Panel (TSACP) and the TRUSIGHT® Tumor Panel. For each panel, two lots of the AcroMetrix® Oncology Hotspot Control were tested in duplicate, in at least two sites. Additional sites only tested one of the lots at least twice or both lots once. Sources of variation between sites may include different instruments, operators and general workflows. Also, variation in bioinformatics pipelines may have contributed significantly to variation in performance results.

Figure 8:
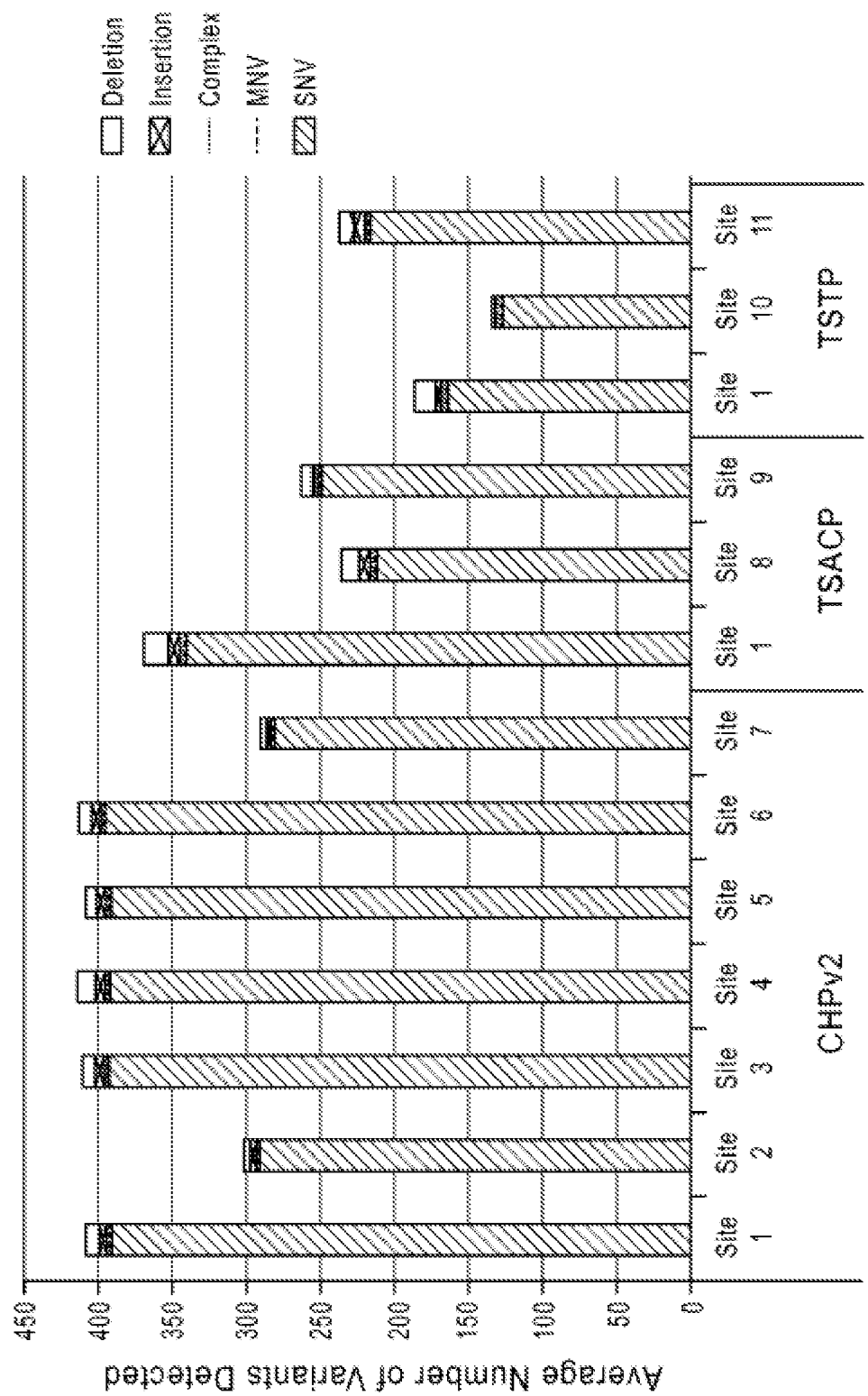
FIG. 8 is a graph showing the number of variants (deletions, insertions, complex, multiple nucleotide variants (MNV), and single nucleotide variants (SNV)) and average number of variants detected across multiple sites using CHPv2 (AMPLISEQ™ Cancer Hotspot Panel version 2), TSACP(TRUSEQ™ Amplicon Cancer Panel), and TSTP (TRUSIGHT™ Tumor Panel).

FIG. 8 shows performance across different sites and panels. The average number of variants of different types detected in the ACROMETRIX® Oncology Hotspot Control are reported by site and grouped by panel. Note: The total number of variants of each type is different for each panel. See FIGS. 8-11.

Figure 9:
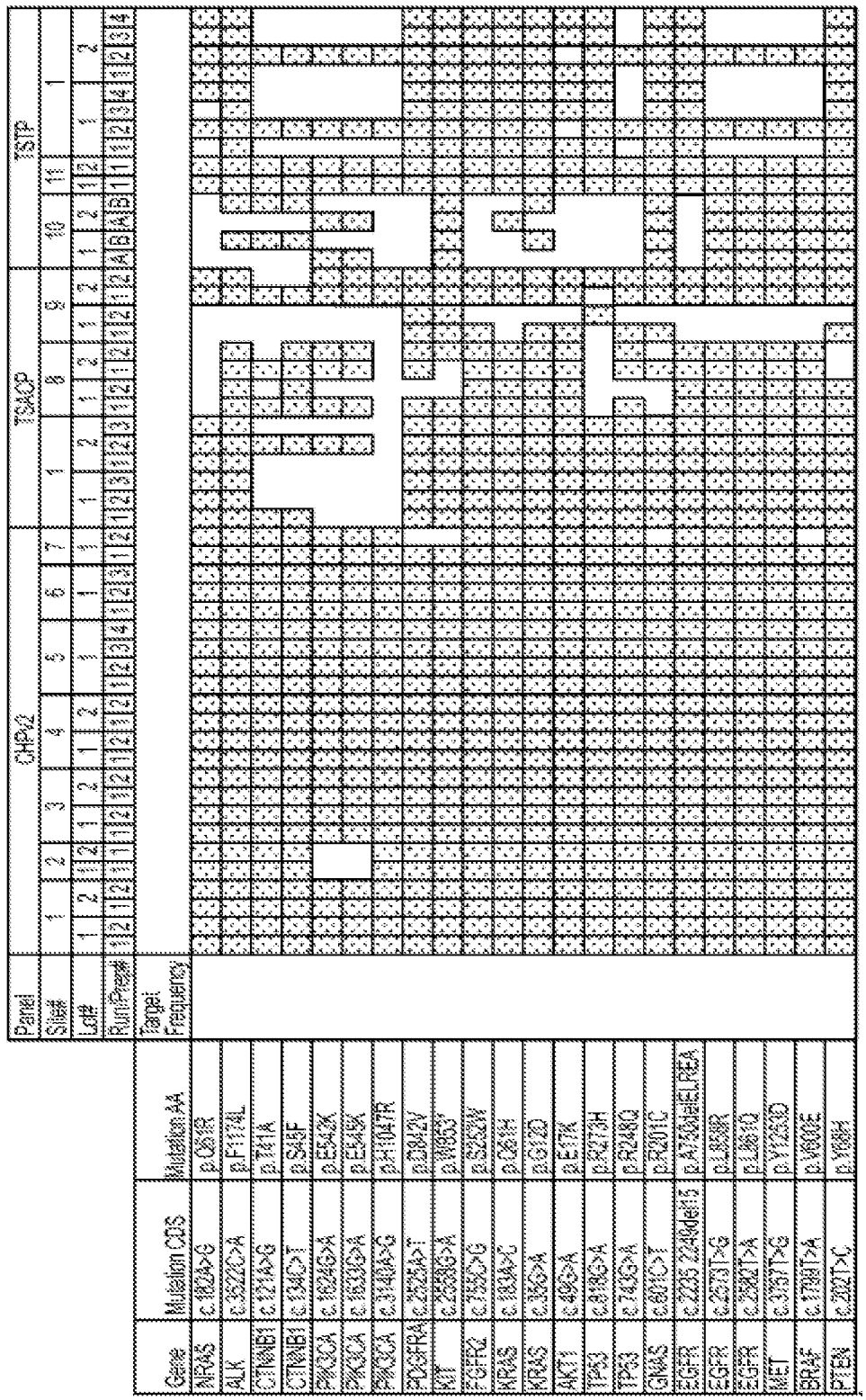
FIG. 9 is a graph showing analysis conducted with data from sites that tested two lots of the control at least once or one lot at least twice. Detection is indicated in dark squares and absence light squares.
Figure 10:
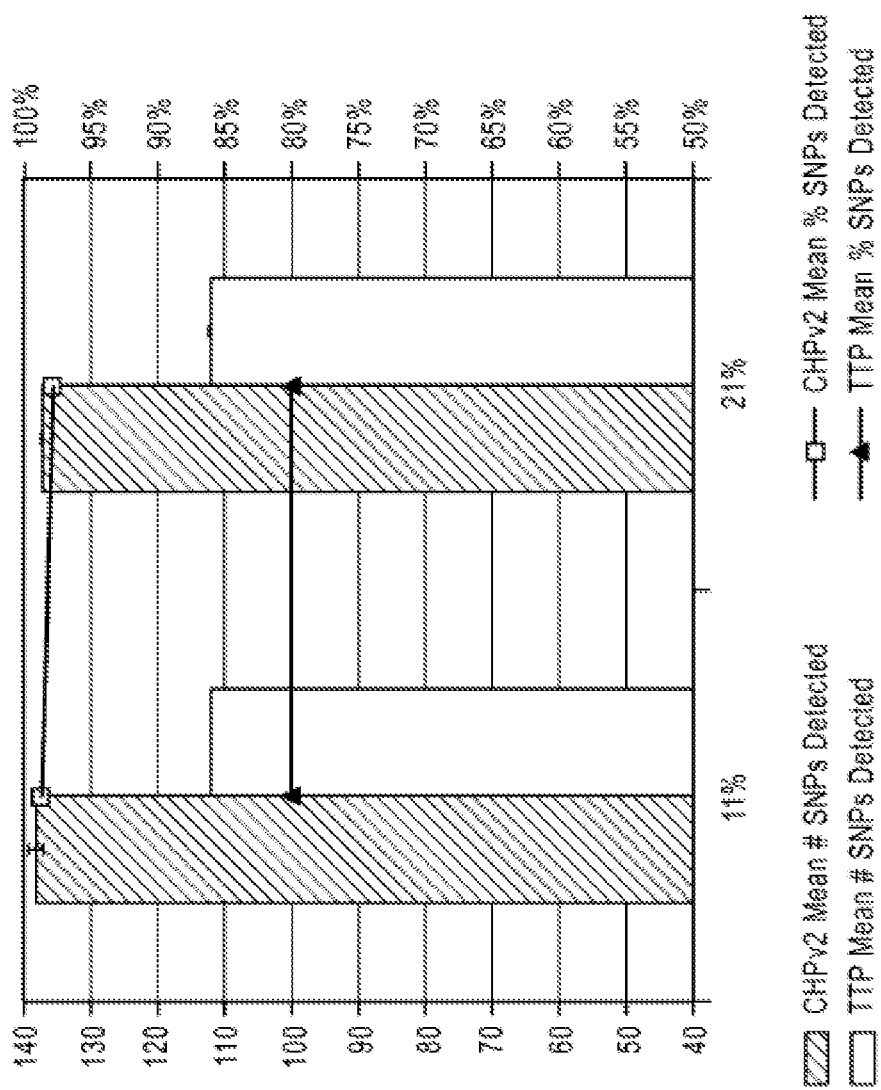
FIG. 10 is a graph showing the mean number and mean percentage SNPs detected for CHPv2 and TTP.
Figure 11:
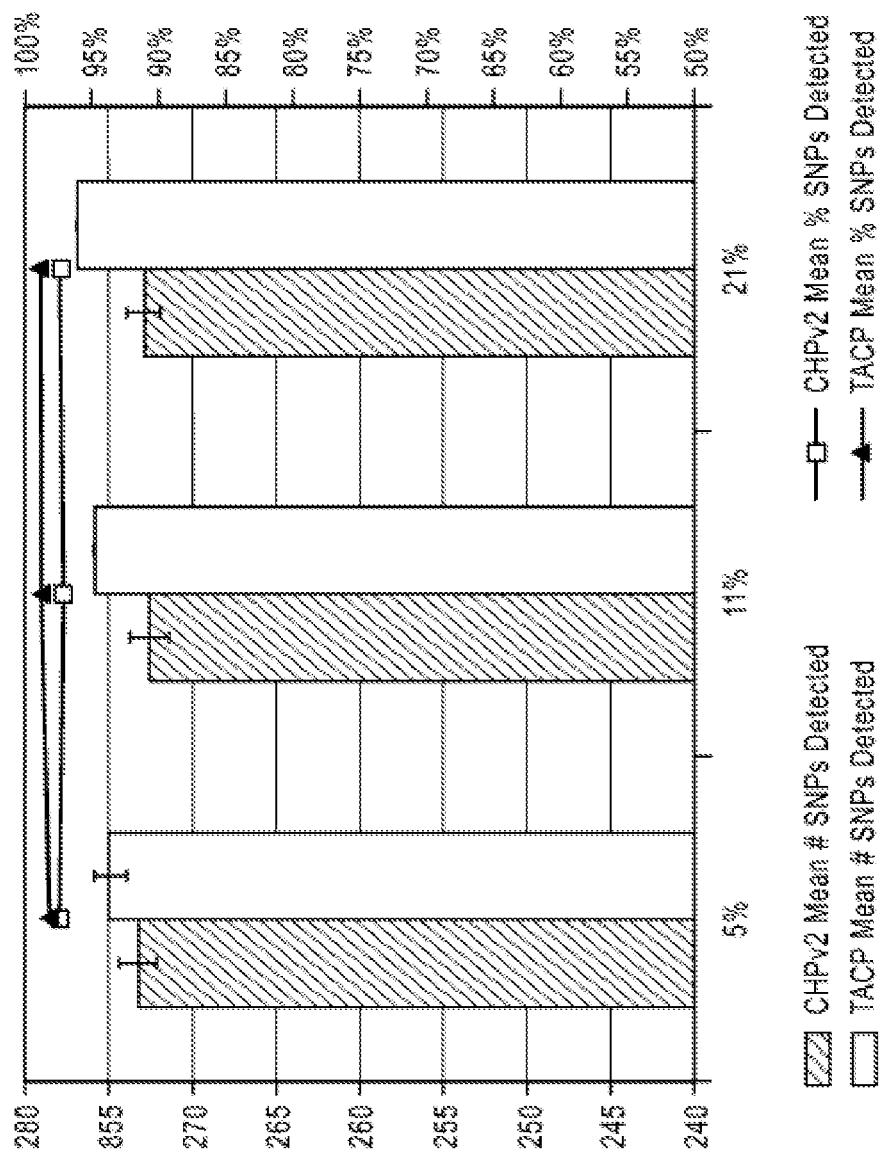
FIG. 11 is a graph showing the mean number and mean percentage of SNPs detected for CHPv2 and TACP.

To assess the detection of specific variants across different panels, twenty-two clinically-relevant variants that were targeted by three panels were selected. FIG. 9 shows detection of 22 selected variants across panels. Analysis was conducted with data from sites that tested two lots of the control at least once or one lot at least twice. Detection is indicated in dark squares and absence indicated in light squares. Site-to-site differences are apparent, even amongst those utilizing the same library preparation method, indicating the likelihood of the bioinformatics pipeline having an impact on performance.

Example 4

Performance of the control material comprising 555 variants is shown in Table 9, wherein SNV (single nucleotide variant), MNV (multiple nucleotide variant), DEL (deletion), INS (insertion), for CHPv2 (AMPLISEQ® Cancer Hotspot Panel v2), TSACP (TRUSEQ® Amplicon cancer panel), and TSTP (TRUSIGHT® tumor panel) are shown. A variant was considered to be covered by the test method if the variant was positioned between the upstream and downstream primers. A variant was considered detected if it was detected in at least one run of the control. Sanger sequencing was performed on the synthetic DNA prior to dilution with genomic DNA. Variants detected in the genomic DNA were confirmed using publicly available whole genome sequencing information for GM24385.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 1A

Exemplary Hotspot (HS) Variants

| Gene name | Mutation ID | Mutation CDS | Mutation Description | Chr | Start | End |
|---|---|---|---|---|---|---|
| MPL | 27286 | c.1514G > A | Substitution - Missense | 1 | 43814979 | 43814979 |
| MPL | 18918 | c.1544G > T | Substitution - Missense | 1 | 43815009 | 43815009 |
| MPL | 27290 | c.1555G > A | Substitution - Missense | 1 | 43815020 | 43815020 |
| NRAS | 584 | c.182A > G | Substitution - Missense | 1 | 115256529 | 115256529 |
| NRAS | 1332933 | c.174A > G | Substitution - coding silent | 1 | 115256537 | 115256537 |
| NRAS | 577 | c.52G > A | Substitution - Missense | 1 | 115258730 | 115258730 |
| NRAS | 564 | c.35G > A | Substitution - Missense | 1 | 115258747 | 115258747 |
| NRAS | 24850 | c.29G > A | Substitution - Missense | 1 | 115258753 | 115258753 |
| ALK | 28056 | c.3824G > A | Substitution - Missense | 2 | 29432664 | 29432664 |
| ALK | 28055 | c.3522C > A | Substitution - Missense | 2 | 29443695 | 29443695 |
| MSH6 | 13399 | c.3246G > T | Substitution - coding silent | 2 | 48030632 | 48030632 |
| MSH6 | 13395 | c.3261delC | Deletion - Frameshift | 2 | 48030647 | 48030647 |
| MSH6 | 1021299 | c.3300G > A | Substitution - coding silent | 2 | 48030686 | 48030686 |
| IDH1 | 28746 | c.395G > A | Substitution - Missense | 2 | 209113112 | 209113112 |
| IDH1 | 1404902 | c.388A > G | Substitution - Missense | 2 | 209113119 | 209113119 |
| IDH1 | 96922 | c.367G > A | Substitution - Missense | 2 | 209113140 | 209113140 |
| ERBB4 | 48362 | c.2791G > T | Substitution - Missense | 2 | 212288954 | 212288955 |
| ERBB4 | 169572 | c.2782G > T | Substitution - Nonsense | 2 | 212288963 | 212288964 |
| ERBB4 | 232263 | c.1835G > A | Substitution - Missense | 2 | 212530083 | 212530084 |
| ERBB4 | 573362 | c.1828C > A | Substitution - Missense | 2 | 212530090 | 212530091 |
| ERBB4 | 1405173 | c.1784A > G | Substitution - Missense | 2 | 212530134 | 212530135 |
| ERBB4 | 1614287 | c.1089T > C | Substitution - coding silent | 2 | 212576809 | 212576810 |
| ERBB4 | 110095 | c.1022C > T | Substitution - Missense | 2 | 212576876 | 212576877 |
| ERBB4 | 573356 | c.1003G > T | Substitution - Missense | 2 | 212576895 | 212576896 |
| ERBB4 | 1405181 | c.909T > C | Substitution - coding silent | 2 | 212578347 | 212578348 |
| ERBB4 | 160825 | c.885T > G | Substitution - Missense | 2 | 212578371 | 212578372 |
| ERBB4 | 1015994 | c.829C > A | Substitution - Missense | 2 | 212587171 | 212587172 |
| ERBB4 | 1251447 | c.804C > A | Substitution - Nonsense | 2 | 212587196 | 212587197 |
| ERBB4 | 1405184 | c.730A > G | Substitution - Missense | 2 | 212589811 | 212589812 |

TABLE 1A-continued

Exemplary Hotspot (HS) Variants

| Gene name | Mutation ID | Mutation CDS | Mutation Description | Chr | Start | End |
|---|---|---|---|---|---|---|
| ERBB4 | 573353 | c.704C > T | Substitution - Missense | 2 | 212589837 | 212589838 |
| ERBB4 | 1015997 | c.633G > A | Substitution - coding silent | 2 | 212589908 | 212589909 |
| ERBB4 | 48369 | c.542A > G | Substitution - Missense | 2 | 212652763 | 212652764 |
| ERBB4 | 442267 | c.515C > G | Substitution - Missense | 2 | 212652790 | 212652791 |
| VHL | 14305 | c.266T > A | Substitution - Missense | 3 | 10183797 | 10183797 |
| VHL | 18080 | c.277G > C | Substitution - Missense | 3 | 10183808 | 10183808 |
| VHL | 17658 | c.286C > T | Substitution - Nonsense | 3 | 10183817 | 10183817 |
| VHL | 17886 | c.296delC | Deletion - Frameshift | 3 | 10183827 | 10183827 |
| VHL | 17752 | c.343C > A | Substitution - Missense | 3 | 10188200 | 10188200 |
| VHL | 14312 | c.353T > C | Substitution - Missense | 3 | 10188210 | 10188210 |
| VHL | 14407 | c.388G > C | Substitution - Missense | 3 | 10188245 | 10188245 |
| VHL | 14412 | c.431delG | Deletion - Frameshift | 3 | 10188288 | 10188288 |
| VHL | 17657 | c.472C > G | Substitution - Missense | 3 | 10191479 | 10191479 |
| VHL | 17612 | c.481C > T | Substitution - Nonsense | 3 | 10191488 | 10191488 |
| VHL | 14311 | c.499C > T | Substitution - Nonsense | 3 | 10191506 | 10191506 |
| VHL | 17837 | c.506T > C | Substitution - Missense | 3 | 10191513 | 10191513 |
| MLH1 | 26085 | c.1151T > A | Substitution - Missense | 3 | 37067240 | 37067240 |
| CTNNB1 | 5677 | c.98C > G | Substitution - Missense | 3 | 41266101 | 41266101 |
| CTNNB1 | 5662 | c.110C > T | Substitution - Missense | 3 | 41266113 | 41266113 |
| CTNNB1 | 5664 | c.121A > G | Substitution - Missense | 3 | 41266124 | 41266124 |
| CTNNB1 | 5667 | c.134C > T | Substitution - Missense | 3 | 41266137 | 41266137 |
| FOXL2 | 33661 | c.402C > G | Substitution - Missense | 3 | 138665163 | 138665163 |
| PIK3CA | 27495 | c.35G > A | Substitution - Missense | 3 | 178916648 | 178916648 |
| PIK3CA | 27376 | c.93A > G | Substitution - Missense | 3 | 178916706 | 178916706 |
| PIK3CA | 1420738 | c.180A > G | Substitution - coding silent | 3 | 178916793 | 178916793 |
| PIK3CA | 1041454 | c.210C > T | Substitution - coding silent | 3 | 178916823 | 178916823 |
| PIK3CA | 27497 | c.323G > A | Substitution - Missense | 3 | 178916936 | 178916936 |
| PIK3CA | 13570 | c.331A > G | Substitution - Missense | 3 | 178916944 | 178916944 |
| PIK3CA | 125368 | c.344G > T | Substitution - Missense | 3 | 178916957 | 178916957 |
| PIK3CA | 1420774 | c.536A > G | Substitution - Missense | 3 | 178917661 | 178917661 |
| PIK3CA | 21462 | c.971C > T | Substitution - Missense | 3 | 178921489 | 178921489 |
| PIK3CA | 353193 | c.1002C > T | Substitution - coding silent | 3 | 178921520 | 178921520 |
| PIK3CA | 754 | c.1035T > A | Substitution - Missense | 3 | 178921553 | 178921553 |
| PIK3CA | 1420804 | c.1213T > C | Substitution - Missense | 3 | 178927450 | 178927450 |
| PIK3CA | 757 | c.1258T > C | Substitution - Missense | 3 | 178927980 | 178927980 |
| PIK3CA | 1420828 | c.1370A > G | Substitution - Missense | 3 | 178928092 | 178928092 |
| PIK3CA | 759 | c.1616C > G | Substitution - Missense | 3 | 178936074 | 178936074 |
| PIK3CA | 760 | c.1624G > A | Substitution - Missense | 3 | 178936082 | 178936082 |
| PIK3CA | 763 | c.1633G > A | Substitution - Missense | 3 | 178936091 | 178936091 |
| PIK3CA | 1420865 | c.1640A > G | Substitution - Missense | 3 | 178936098 | 178936098 |
| PIK3CA | 778 | c.2102A > C | Substitution - Missense | 3 | 178938860 | 178938860 |
| PIK3CA | 769 | c.2702G > T | Substitution - Missense | 3 | 178947827 | 178947827 |
| PIK3CA | 770 | c.2725T > C | Substitution - Missense | 3 | 178947850 | 178947850 |
| PIK3CA | 328026 | c.3110A > G | Substitution - Missense | 3 | 178952055 | 178952055 |
| PIK3CA | 775 | c.3140A > G | Substitution - Missense | 3 | 178952085 | 178952085 |
| PIK3CA | 12464 | c.3204_3205insA | Insertion - Frameshift | 3 | 178952150 | 178952150 |
| FGFR3 | 715 | c.746C > G | Substitution - Missense | 4 | 1803568 | 1803568 |
| FGFR3 | 29446 | c.753C > T | Substitution - coding silent | 4 | 1803575 | 1803575 |
| FGFR3 | 723 | c.850delC | Deletion - Frameshift | 4 | 1803672 | 1803672 |
| FGFR3 | 716 | c.1108G > T | Substitution - Missense | 4 | 1806089 | 1806089 |
| FGFR3 | 24842 | c.1138G > A | Substitution - Missense | 4 | 1806119 | 1806119 |
| FGFR3 | 724 | c.1150T > C | Substitution - Missense | 4 | 1806131 | 1806131 |
| FGFR3 | 721 | c.1172C > A | Substitution - Missense | 4 | 1806153 | 1806153 |
| FGFR3 | 1428724 | c.1928A > G | Substitution - Missense | 4 | 1807869 | 1807869 |
| FGFR3 | 719 | c.1948A > G | Substitution - Missense | 4 | 1807889 | 1807889 |
| FGFR3 | 24802 | c.2089G > T | Substitution - Missense | 4 | 1808331 | 1808331 |
| PDGFRA | 12418 | c.1698_1712del15 | Complex - deletion inframe | 4 | 55141052 | 55141066 |
| PDGFRA | 1430085 | c.1743T > C | Substitution - coding silent | 4 | 55141097 | 55141097 |
| PDGFRA | 22415 | c.1977C > A | Substitution - Missense | 4 | 55144148 | 55144148 |
| PDGFRA | 1430086 | c.2001A > G | Substitution - coding silent | 4 | 55144172 | 55144172 |
| PDGFRA | 743 | c.2021C > T | Substitution - Missense | 4 | 55144547 | 55144547 |
| PDGFRA | 587613 | c.2517G > T | Substitution - coding silent | 4 | 55152085 | 55152085 |
| PDGFRA | 736 | c.2525A > T | Substitution - Missense | 4 | 55152093 | 55152093 |
| PDGFRA | 28052 | c.2544C > A | Substitution - Missense | 4 | 55152112 | 55152112 |
| KIT | 77973 | c.92C > T | Substitution - Missense | 4 | 55561702 | 55561702 |
| KIT | 1146 | c.154G > A | Substitution - Missense | 4 | 55561764 | 55561764 |
| KIT | 1430106 | c.218A > G | Substitution - Missense | 4 | 55561828 | 55561828 |
| KIT | 24637 | c.1405T > C | Substitution - Missense | 4 | 55592081 | 55592081 |
| KIT | 41602 | c.1416A > G | Substitution - coding silent | 4 | 55592092 | 55592092 |
| KIT | 1326 | c.1509_1510insGCCTAT | Insertion - In frame | 4 | 55592185 | 55592186 |
| KIT | 96867 | c.1516T > C | Substitution - Missense | 4 | 55592192 | 55592192 |
| KIT | 96885 | c.1526A > T | Substitution - Missense | 4 | 55592202 | 55592202 |
| KIT | 1430136 | c.1535A > G | Substitution - Missense | 4 | 55592211 | 55592211 |
| KIT | 1155 | c.1588G > A | Substitution - Missense | 4 | 55593431 | 55593431 |
| KIT | 1275 | c.1698C > T | Substitution - coding silent | 4 | 55593632 | 55593632 |

TABLE 1A-continued

Exemplary Hotspot (HS) Variants

| Gene name | Mutation ID | Mutation CDS | Mutation Description | Chr | Start | End |
|---|---|---|---|---|---|---|
| KIT | 1290 | c.1727T > C | Substitution - Missense | 4 | 55593661 | 55593661 |
| KIT | 1299 | c.1755C > T | Substitution - coding silent | 4 | 55593689 | 55593689 |
| KIT | 1304 | c.1924A > G | Substitution - Missense | 4 | 55594221 | 55594221 |
| KIT | 12706 | c.1961T > C | Substitution - Missense | 4 | 55594258 | 55594258 |
| KIT | 36053 | c.2089G > T | Substitution - Missense | 4 | 55595599 | 55595599 |
| KIT | 1430171 | c.2148T > C | Substitution - coding silent | 4 | 55597500 | 55597500 |
| KIT | 21303 | c.2209G > A | Substitution - Missense | 4 | 55597561 | 55597561 |
| KIT | 20402 | c.2410C > T | Substitution - Missense | 4 | 55599284 | 55599284 |
| KIT | 19194 | c.2484 + 43T > A | Unknown | 4 | 55599401 | 55599401 |
| KIT | 133767 | c.2558G > A | Substitution - Nonsense | 4 | 55602737 | 55602737 |
| KDR | 35855 | c.4008C > T | Substitution - coding silent | 4 | 55946171 | 55946171 |
| KDR | 1430203 | c.3433G > A | Substitution - Missense | 4 | 55955112 | 55955112 |
| KDR | 48464 | c.2917G > T | Substitution - Missense | 4 | 55961023 | 55961023 |
| KDR | 1430212 | c.2619A > G | Substitution - coding silent | 4 | 55962505 | 55962505 |
| KDR | 32339 | c.824G > T | Substitution - Missense | 4 | 55979623 | 55979623 |
| FBXW7 | 1427592 | c.2079A > G | Substitution - coding silent | 4 | 153244078 | 153244078 |
| FBXW7 | 27083 | c.2065C > T | Substitution - Missense | 4 | 153244092 | 153244092 |
| FBXW7 | 732399 | c.2033C > G | Substitution - Nonsense | 4 | 153244124 | 153244124 |
| FBXW7 | 34018 | c.2001delG | Deletion - Frameshift | 4 | 153244156 | 153244156 |
| FBXW7 | 27913 | c.1580A > G | Substitution - Missense | 4 | 153247222 | 153247222 |
| FBXW7 | 30599 | c.1576T > C | Substitution - Missense | 4 | 153247226 | 153247226 |
| FBXW7 | 30598 | c.1558G > A | Substitution - Missense | 4 | 153247244 | 153247244 |
| FBXW7 | 34016 | c.1451G > T | Substitution - Missense | 4 | 153247351 | 153247351 |
| FBXW7 | 22974 | c.1436G > A | Substitution - Missense | 4 | 153247366 | 153247366 |
| FBXW7 | 22965 | c.1394G > A | Substitution - Missense | 4 | 153249384 | 153249384 |
| FBXW7 | 22986 | c.1338G > A | Substitution - Nonsense | 4 | 153249440 | 153249440 |
| FBXW7 | 161024 | c.1322G > T | Substitution - Missense | 4 | 153249456 | 153249456 |
| FBXW7 | 22973 | c.1177C > T | Substitution - Nonsense | 4 | 153250883 | 153250883 |
| FBXW7 | 22971 | c.832C > T | Substitution - Missense | 4 | 153258983 | 153258983 |
| FBXW7 | 1052125 | c.744G > T | Substitution - Missense | 4 | 153259071 | 153259071 |
| APC | 18979 | c.2543_2544insA | Insertion - Frameshift | 5 | 112173834 | 112173835 |
| APC | 18852 | c.2626C > T | Substitution - Nonsense | 5 | 112173917 | 112173917 |
| APC | 19230 | c.2639T > C | Substitution - Missense | 5 | 112173930 | 112173930 |
| APC | 19330 | c.2656C > T | Substitution - Nonsense | 5 | 112173947 | 112173947 |
| APC | 19065 | c.2752G > T | Substitution - Nonsense | 5 | 112174043 | 112174043 |
| APC | 13872 | c.3286C > T | Substitution - Nonsense | 5 | 112174577 | 112174577 |
| APC | 1432250 | c.3305A > G | Substitution - Missense | 5 | 112174596 | 112174596 |
| APC | 1432260 | c.3435A > G | Substitution - coding silent | 5 | 112174726 | 112174726 |
| APC | 41617 | c.3700delA | Deletion - Frameshift | 5 | 112174991 | 112174991 |
| APC | 1432280 | c.3795A > G | Substitution - coding silent | 5 | 112175086 | 112175086 |
| APC | 19072 | c.3871C > T | Substitution - Nonsense | 5 | 112175162 | 112175162 |
| APC | 18960 | c.3880C > T | Substitution - Nonsense | 5 | 112175171 | 112175171 |
| APC | 18719 | c.3923_3924insA | Insertion - Frameshift | 5 | 112175214 | 112175215 |
| APC | 18702 | c.3964G > T | Substitution - Nonsense | 5 | 112175255 | 112175255 |
| APC | 19048 | c.4057G > T | Substitution - Nonsense | 5 | 112175348 | 112175348 |
| APC | 19652 | c.4063T > C | Substitution - Missense | 5 | 112175354 | 112175354 |
| APC | 18862 | c.4132C > T | Substitution - Nonsense | 5 | 112175423 | 112175423 |
| APC | 143913 | c.4141C > T | Substitution - Missense | 5 | 112175432 | 112175432 |
| APC | 18993 | c.4189_4190delGA | Deletion - Frameshift | 5 | 112175480 | 112175481 |
| APC | 19087 | c.4216C > T | Substitution - Nonsense | 5 | 112175507 | 112175507 |
| APC | 18836 | c.4285C > T | Substitution - Nonsense | 5 | 112175576 | 112175576 |
| APC | 13864 | c.4393_4394delAG | Deletion - Frameshift | 5 | 112175684 | 112175685 |
| APC | 1173082 | c.4540delC | Deletion - Frameshift | 5 | 112175831 | 112175831 |
| APC | 1183180 | c.4561G > T | Substitution - Nonsense | 5 | 112175852 | 112175852 |
| APC | 13879 | c.4639G > T | Substitution - Nonsense | 5 | 112175930 | 112175930 |
| APC | 41616 | c.4654G > T | Substitution - Nonsense | 5 | 112175945 | 112175945 |
| APC | 18561 | c.4666_4667insA | Insertion - Frameshift | 5 | 112175957 | 112175958 |
| APC | 18875 | c.4773_4774insA | Insertion - Frameshift | 5 | 112176064 | 112176065 |
| APC | 42906 | c.4826C > T | Substitution - Nonsense | 5 | 112176117 | 112176117 |
| CSF1R | 947 | c.2906A > G | Substitution - Missense | 5 | 149433644 | 149433645 |
| CSF1R | 310349 | c.2878G > A | Substitution - Missense | 5 | 149433672 | 149433673 |
| NPM1 | 17559 | c.863_864insTCTG | Insertion - Frameshift | 5 | 170837547 | 170837548 |
| EGFR | 21683 | c.323G > A | Substitution - Missense | 7 | 55211080 | 55211080 |
| EGFR | 174732 | c.340G > A | Substitution - Missense | 7 | 55211097 | 55211097 |
| EGFR | 1451540 | c.408C > T | Substitution - coding silent | 7 | 55211165 | 55211165 |
| EGFR | 21687 | c.866C > T | Substitution - Missense | 7 | 55221822 | 55221822 |
| EGFR | 43067 | c.874G > T | Substitution - Missense | 7 | 55221830 | 55221830 |
| EGFR | 21690 | c.1793G > T | Substitution - Missense | 7 | 55233043 | 55233043 |
| EGFR | 35825 | c.1859G > A | Substitution - Missense | 7 | 55233109 | 55233109 |
| EGFR | 13177 | c.2063T > C | Substitution - Missense | 7 | 55241615 | 55241615 |
| EGFR | 41905 | c.2092G > A | Substitution - Missense | 7 | 55241644 | 55241644 |
| EGFR | 6239 | c.2156G > C | Substitution - Missense | 7 | 55241708 | 55241708 |
| EGFR | 13979 | c.2170G > A | Substitution - Missense | 7 | 55241722 | 55241722 |
| EGFR | 53194 | c.2197C > T | Substitution - Missense | 7 | 55242427 | 55242427 |
| EGFR | 13182 | c.2203G > A | Substitution - Missense | 7 | 55242433 | 55242433 |
| EGFR | 17570 | c.2222C > T | Substitution - Missense | 7 | 55242452 | 55242452 |

TABLE 1A-continued

Exemplary Hotspot (HS) Variants

| Gene name | Mutation ID | Mutation CDS | Mutation Description | Chr | Start | End |
|---|---|---|---|---|---|---|
| EGFR | 6223 | c.2235_2249del15 | Deletion - In frame | 7 | 55242465 | 55242479 |
| EGFR | 28603 | c.2293G > A | Substitution - Missense | 7 | 55248995 | 55248995 |
| EGFR | 13190 | c.2375T > C | Substitution - Missense | 7 | 55249077 | 55249077 |
| EGFR | 12986 | c.2429G > A | Substitution - Missense | 7 | 55249131 | 55249131 |
| EGFR | 28610 | c.2441T > C | Substitution - Missense | 7 | 55249143 | 55249143 |
| EGFR | 53291 | c.2485G > A | Substitution - Missense | 7 | 55259427 | 55259427 |
| EGFR | 13424 | c.2497T > G | Substitution - Missense | 7 | 55259439 | 55259439 |
| EGFR | 6227 | c.2504A > T | Substitution - Missense | 7 | 55259446 | 55259446 |
| EGFR | 13430 | c.2515G > A | Substitution - Missense | 7 | 55259457 | 55259457 |
| EGFR | 6224 | c.2573T > G | Substitution - Missense | 7 | 55259515 | 55259515 |
| EGFR | 6213 | c.2582T > A | Substitution - Missense | 7 | 55259524 | 55259524 |
| EGFR | 14070 | c.2588G > A | Substitution - Missense | 7 | 55259530 | 55259530 |
| EGFR | 13008 | c.2612C > G | Substitution - Missense | 7 | 55259554 | 55259554 |
| MET | 706 | c.504G > T | Substitution - Missense | 7 | 116339642 | 116339642 |
| MET | 710 | c.1124A > G | Substitution - Missense | 7 | 116340262 | 116340262 |
| MET | 29633 | c.3082 + 1G > A | Unknown | 7 | 116412044 | 116412044 |
| MET | 1447462 | c.3336T > C | Substitution - coding silent | 7 | 116417465 | 116417465 |
| MET | 697 | c.3370C > G | Substitution - Missense | 7 | 116417499 | 116417499 |
| MET | 43064 | c.3534G > C | Substitution - Missense | 7 | 116418969 | 116418969 |
| MET | 1214928 | c.3562C > T | Substitution - Nonsense | 7 | 116418997 | 116418997 |
| MET | 1447471 | c.3573T > C | Substitution - coding silent | 7 | 116419008 | 116419008 |
| MET | 1330154 | c.3668T > G | Substitution - Missense | 7 | 116422133 | 116422133 |
| MET | 700 | c.3757T > G | Substitution - Missense | 7 | 116423428 | 116423428 |
| MET | 48565 | c.3778G > T | Substitution - Missense | 7 | 116423449 | 116423449 |
| MET | 695 | c.3785A > G | Substitution - Missense | 7 | 116423456 | 116423456 |
| MET | 691 | c.3803T > C | Substitution - Missense | 7 | 116423474 | 116423474 |
| SMO | 13145 | c.595C > T | Substitution - Missense | 7 | 128845101 | 128845101 |
| SMO | 13147 | c.970G > A | Substitution - Missense | 7 | 128846040 | 128846040 |
| SMO | 216037 | c.1234C > T | Substitution - Missense | 7 | 128846398 | 128846398 |
| SMO | 13146 | c.1604G > T | Substitution - Missense | 7 | 128850341 | 128850341 |
| SMO | 13150 | c.1918A > G | Substitution - Missense | 7 | 128851593 | 128851593 |
| BRAF | 476 | c.1799T > A | Substitution - Missense | 7 | 140453136 | 140453136 |
| BRAF | 471 | c.1790T > G | Substitution - Missense | 7 | 140453145 | 140453145 |
| BRAF | 467 | c.1781A > G | Substitution - Missense | 7 | 140453154 | 140453154 |
| BRAF | 462 | c.1742A > G | Substitution - Missense | 7 | 140453193 | 140453193 |
| BRAF | 450 | c.1391G > T | Substitution - Missense | 7 | 140481417 | 140481417 |
| BRAF | 27986 | c.1380A > G | Substitution - coding silent | 7 | 140481428 | 140481428 |
| BRAF | 1448625 | c.1359T > C | Substitution - coding silent | 7 | 140481449 | 140481449 |
| BRAF | 6262 | c.1330C > T | Substitution - Missense | 7 | 140481478 | 140481478 |
| EZH2 | 37028 | c.1937A > T | Substitution - Missense | 7 | 148508727 | 148508727 |
| FGFR1 | 1292693 | c.816C > T | Substitution - coding silent | 8 | 38282147 | 38282147 |
| FGFR1 | 187237 | c.448C > T | Substitution - Missense | 8 | 38285864 | 38285864 |
| FGFR1 | 1456955 | c.421A > G | Substitution - Missense | 8 | 38285891 | 38285891 |
| FGFR1 | 601 | c.374C > T | Substitution - Missense | 8 | 38285938 | 38285938 |
| JAK2 | 12600 | c.1849G > T | Substitution - Missense | 9 | 5073770 | 5073770 |
| JAK2 | 27063 | c.1860C > A | Substitution - Missense | 9 | 5073781 | 5073781 |
| CDKN2A | 12479 | c.358G > T | Substitution - Nonsense | 9 | 21971000 | 21971000 |
| CDKN2A | 12476 | c.341C > T | Substitution - Missense | 9 | 21971017 | 21971017 |
| CDKN2A | 12547 | c.330G > A | Substitution - Nonsense | 9 | 21971028 | 21971028 |
| CDKN2A | 13489 | c.322G > T | Substitution - Missense | 9 | 21971036 | 21971036 |
| CDKN2A | 12504 | c.247C > T | Substitution - Missense | 9 | 21971111 | 21971111 |
| CDKN2A | 12475 | c.238C > T | Substitution - Nonsense | 9 | 21971120 | 21971120 |
| CDKN2A | 13281 | c.205G > T | Substitution - Nonsense | 9 | 21971153 | 21971153 |
| CDKN2A | 12473 | c.172C > T | Substitution - Nonsense | 9 | 21971186 | 21971186 |
| GNAQ | 1110323 | c.1002C > T | Substitution - coding silent | 9 | 80336317 | 80336317 |
| GNAQ | 52975 | c.548G > A | Substitution - Missense | 9 | 80412493 | 80412493 |
| GNAQ | 1463119 | c.523A > T | Substitution - Missense | 9 | 80412518 | 80412518 |
| ABL1 | 12631 | c.742C > G | Substitution - Missense | 9 | 133738342 | 133738342 |
| ABL1 | 12577 | c.749G > A | Substitution - Missense | 9 | 133738349 | 133738349 |
| ABL1 | 12576 | c.757T > C | Substitution - Missense | 9 | 133738357 | 133738357 |
| ABL1 | 12573 | c.763G > A | Substitution - Missense | 9 | 133738363 | 133738363 |
| ABL1 | 12602 | c.827A > G | Substitution - Missense | 9 | 133747520 | 133747520 |
| ABL1 | 235737 | c.878_879insGCC | Complex - insertion inframe | 9 | 133747571 | 133747572 |
| ABL1 | 12578 | c.1052T > C | Substitution - Missense | 9 | 133748391 | 133748391 |
| ABL1 | 12611 | c.1064A > G | Substitution - Missense | 9 | 133748403 | 133748403 |
| ABL1 | 12605 | c.1075T > G | Substitution - Missense | 9 | 133748414 | 133748414 |
| ABL1 | 49071 | c.1150C > A | Substitution - Missense | 9 | 133750319 | 133750319 |
| ABL1 | 12604 | c.1187A > G | Substitution - Missense | 9 | 133750356 | 133750356 |
| NOTCH1 | 87862 | c.7412C > A | Substitution - Nonsense | 9 | 139390779 | 139390779 |
| NOTCH1 | 13070 | c.7386delC | Deletion - Frameshift | 9 | 139390805 | 139390805 |
| NOTCH1 | 12776 | c.7375C > T | Substitution - Missense | 9 | 139390816 | 139390816 |
| NOTCH1 | 13061 | c.7318C > T | Substitution - Nonsense | 9 | 139390873 | 139390873 |
| NOTCH1 | 13048 | c.5033T > C | Substitution - Missense | 9 | 139397768 | 139397768 |
| NOTCH1 | 308587 | c.5025C > T | Substitution - coding silent | 9 | 139397776 | 139397776 |
| NOTCH1 | 12771 | c.4799T > C | Substitution - Missense | 9 | 139399344 | 139399344 |
| NOTCH1 | 13053 | c.4793G > C | Substitution - Missense | 9 | 139399350 | 139399350 |

TABLE 1A-continued

Exemplary Hotspot (HS) Variants

| Gene name | Mutation ID | Mutation CDS | Mutation Description | Chr | Start | End |
|---|---|---|---|---|---|---|
| NOTCH1 | 13042 | c.4778T > C | Substitution - Missense | 9 | 139399365 | 139399365 |
| NOTCH1 | 12772 | c.4721T > C | Substitution - Missense | 9 | 139399422 | 139399422 |
| RET | 29803 | c.1852T > C | Substitution - Missense | 10 | 43609096 | 43609096 |
| RET | 29804 | c.1858T > C | Substitution - Missense | 10 | 43609102 | 43609102 |
| RET | 1048 | c.1894_1906 > AGCT | Complex - deletion inframe | 10 | 43609942 | 43609954 |
| RET | 1223553 | c.1942G > A | Substitution - Missense | 10 | 43609990 | 43609990 |
| RET | 976 | c.1991C > A | Substitution - Missense | 10 | 43610039 | 43610039 |
| RET | 21338 | c.2304G > C | Substitution - Missense | 10 | 43613840 | 43613840 |
| RET | 977 | c.2647_2648GC > TT | Substitution - Missense | 10 | 43615568 | 43615569 |
| RET | 963 | c.2701G > A | Substitution - Missense | 10 | 43615622 | 43615622 |
| RET | 965 | c.2753T > C | Substitution - Missense | 10 | 43617416 | 43617416 |
| PTEN | 5298 | c.19G > T | Substitution - Nonsense | 10 | 89624245 | 89624245 |
| PTEN | 5101 | c.40A > G | Substitution - Missense | 10 | 89624266 | 89624266 |
| PTEN | 5153 | c.49C > T | Substitution - Nonsense | 10 | 89624275 | 89624275 |
| PTEN | 5107 | c.71A > G | Substitution - Missense | 10 | 89624297 | 89624297 |
| PTEN | 5134 | c.80A > G | Substitution - Missense | 10 | 89653782 | 89653782 |
| PTEN | 5142 | c.112C > T | Substitution - Missense | 10 | 89653814 | 89653814 |
| PTEN | 5050 | c.142A > G | Substitution - Missense | 10 | 89653844 | 89653844 |
| PTEN | 1349479 | c.156T > C | Substitution - coding silent | 10 | 89653858 | 89653858 |
| PTEN | 5129 | c.163A > G | Substitution - Missense | 10 | 89653865 | 89653865 |
| PTEN | 5257 | c.166T > G | Substitution - Missense | 10 | 89685271 | 89685271 |
| PTEN | 5036 | c.202T > C | Substitution - Missense | 10 | 89685307 | 89685307 |
| PTEN | 5916 | c.209 + 5G > A | Unknown | 10 | 89685319 | 89685319 |
| PTEN | 5102 | c.212G > A | Substitution - Missense | 10 | 89690805 | 89690805 |
| PTEN | 4956 | c.227_228delAT | Deletion - Frameshift | 10 | 89690820 | 89690821 |
| PTEN | 5205 | c.245A > C | Substitution - Missense | 10 | 89690838 | 89690838 |
| PTEN | 5983 | c.253 + 1G > A | Unknown | 10 | 89690847 | 89690847 |
| PTEN | 5139 | c.263A > G | Substitution - Missense | 10 | 89692779 | 89692779 |
| PTEN | 5109 | c.302T > C | Substitution - Missense | 10 | 89692818 | 89692818 |
| PTEN | 5266 | c.314G > T | Substitution - Missense | 10 | 89692830 | 89692830 |
| PTEN | 5199 | c.334C > G | Substitution - Missense | 10 | 89692850 | 89692850 |
| PTEN | 5123 | c.395G > A | Substitution - Missense | 10 | 89692911 | 89692911 |
| PTEN | 5130 | c.449A > G | Substitution - Missense | 10 | 89692965 | 89692965 |
| PTEN | 5144 | c.464A > G | Substitution - Missense | 10 | 89692980 | 89692980 |
| PTEN | 5287 | c.477G > T | Substitution - Missense | 10 | 89692993 | 89692993 |
| PTEN | 5907 | c.493-12delT | Unknown | 10 | 89711863 | 89711863 |
| PTEN | 35406 | c.578T > C | Substitution - Missense | 10 | 89711960 | 89711960 |
| PTEN | 4978 | c.595_597delATG | Deletion - In frame | 10 | 89711977 | 89711979 |
| PTEN | 5279 | c.610C > A | Substitution - Missense | 10 | 89711992 | 89711992 |
| PTEN | 5072 | c.615G > A | Substitution - Missense | 10 | 89711997 | 89711997 |
| PTEN | 5154 | c.697C > T | Substitution - Nonsense | 10 | 89717672 | 89717672 |
| PTEN | 5292 | c.703G > T | Substitution - Nonsense | 10 | 89717678 | 89717678 |
| PTEN | 35849 | c.721T > C | Substitution - Missense | 10 | 89717696 | 89717696 |
| PTEN | 43075 | c.787A > T | Substitution - Nonsense | 10 | 89717762 | 89717762 |
| PTEN | 5809 | c.800delA | Deletion - Frameshift | 10 | 89717775 | 89717775 |
| PTEN | 1349606 | c.879A > G | Substitution - coding silent | 10 | 89720728 | 89720728 |
| PTEN | 5312 | c.895G > T | Substitution - Nonsense | 10 | 89720744 | 89720744 |
| PTEN | 4958 | c.955_958delACTT | Deletion - Frameshift | 10 | 89720804 | 89720807 |
| PTEN | 1349625 | c.1025A > G | Substitution - Missense | 10 | 89720874 | 89720874 |
| PTEN | 5966 | c.1027 – 2A > G | Unknown | 10 | 89725042 | 89725042 |
| PTEN | 4936 | c.1040_1041delTC | Deletion - Frameshift | 10 | 89725057 | 89725058 |
| PTEN | 1349633 | c.1055A > G | Substitution - Missense | 10 | 89725072 | 89725072 |
| PTEN | 23645 | c.1091C > G | Substitution - Missense | 10 | 89725108 | 89725108 |
| FGFR2 | 36912 | c.1647T > A | Substitution - Missense | 10 | 123258034 | 123258034 |
| FGFR2 | 36906 | c.1144T > C | Substitution - Missense | 10 | 123274774 | 123274774 |
| FGFR2 | 36904 | c.1124A > G | Substitution - Missense | 10 | 123274794 | 123274794 |
| FGFR2 | 1346272 | c.1108A > G | Substitution - Missense | 10 | 123274810 | 123274810 |
| FGFR2 | 36901 | c.929A > G | Substitution - Missense | 10 | 123279503 | 123279503 |
| FGFR2 | 29824 | c.913G > A | Substitution - Missense | 10 | 123279519 | 123279519 |
| FGFR2 | 36903 | c.755C > G | Substitution - Missense | 10 | 123279677 | 123279677 |
| HRAS | 499 | c.182A > G | Substitution - Missense | 11 | 533874 | 533874 |
| HRAS | 495 | c.175G > A | Substitution - Missense | 11 | 533881 | 533881 |
| HRAS | 249860 | c.81T > C | Substitution - coding silent | 11 | 534242 | 534242 |
| HRAS | 483 | c.35G > T | Substitution - Missense | 11 | 534288 | 534288 |
| ATM | 21323 | c.1009C > T | Substitution - Missense | 11 | 108117798 | 108117798 |
| ATM | 21825 | c.1229T > C | Substitution - Missense | 11 | 108119823 | 108119823 |
| ATM | 22499 | c.1810C > T | Substitution - Missense | 11 | 108123551 | 108123551 |
| ATM | 1158828 | c.1898 + 2T > A | Unknown | 11 | 108123641 | 108123641 |
| ATM | 21826 | c.2572T > C | Substitution - Missense | 11 | 108138003 | 108138003 |
| ATM | 22507 | c.3925G > A | Substitution - Missense | 11 | 108155132 | 108155132 |
| ATM | 21920 | c.5044G > T | Substitution - Missense | 11 | 108170479 | 108170479 |
| ATM | 218294 | c.5152C > G | Substitution - Missense | 11 | 108170587 | 108170587 |
| ATM | 49005 | c.5178 – 1G > T | Unknown | 11 | 108172374 | 108172374 |
| ATM | 172204 | c.5188C > T | Substitution - Nonsense | 11 | 108172385 | 108172385 |

TABLE 1A-continued

Exemplary Hotspot (HS) Variants

| Gene name | Mutation ID | Mutation CDS | Mutation Description | Chr | Start | End |
|---|---|---|---|---|---|---|
| ATM | 21918 | c.5224G > C | Substitution - Missense | 11 | 108172421 | 108172421 |
| ATM | 12792 | c.5380C > T | Substitution - coding silent | 11 | 108173640 | 108173640 |
| ATM | 1183962 | c.5476T > G | Substitution - Missense | 11 | 108173736 | 108173736 |
| ATM | 21922 | c.5821G > C | Substitution - Missense | 11 | 108180945 | 108180945 |
| ATM | 12951 | c.7325A > C | Substitution - Missense | 11 | 108200958 | 108200958 |
| ATM | 12791 | c.7996A > G | Substitution - Missense | 11 | 108204681 | 108204681 |
| ATM | 21636 | c.8084G > C | Substitution - Missense | 11 | 108205769 | 108205769 |
| ATM | 1235404 | c.8095C > A | Substitution - Missense | 11 | 108205780 | 108205780 |
| ATM | 22481 | c.8174A > T | Substitution - Missense | 11 | 108206594 | 108206594 |
| ATM | 1183939 | c.8624A > G | Substitution - Missense | 11 | 108218045 | 108218045 |
| ATM | 22485 | c.8668C > G | Substitution - Missense | 11 | 108218089 | 108218089 |
| ATM | 21930 | c.8839A > T | Substitution - Missense | 11 | 108225590 | 108225590 |
| ATM | 21626 | c.9023G > A | Substitution - Missense | 11 | 108236087 | 108236087 |
| ATM | 1351060 | c.9054A > G | Substitution - coding silent | 11 | 108236118 | 108236118 |
| ATM | 21624 | c.9139C > T | Substitution - Nonsense | 11 | 108236203 | 108236203 |
| KRAS | 41307 | c.491G > A | Substitution - Missense | 12 | 25362805 | 25362805 |
| KRAS | 19940 | c.351A > C | Substitution - Missense | 12 | 25378647 | 25378647 |
| KRAS | 554 | c.183A > C | Substitution - Missense | 12 | 25380275 | 25380275 |
| KRAS | 546 | c.175G > A | Substitution - Missense | 12 | 25380283 | 25380283 |
| KRAS | 1169214 | c.101C > T | Substitution - Missense | 12 | 25398207 | 25398207 |
| KRAS | 14208 | c.104C > T | Substitution - Missense | 12 | 25398215 | 25398215 |
| KRAS | 521 | c.35G > A | Substitution - Missense | 12 | 25398284 | 25398284 |
| KRAS | 507 | c.24A > G | Substitution - coding silent | 12 | 25398295 | 25398295 |
| PTPN11 | 13011 | c.181G > T | Substitution - Missense | 12 | 112888165 | 112888165 |
| PTPN11 | 13013 | c.205G > A | Substitution - Missense | 12 | 112888189 | 112888189 |
| PTPN11 | 13015 | c.215C > T | Substitution - Missense | 12 | 112888199 | 112888199 |
| PTPN11 | 13000 | c.226G > A | Substitution - Missense | 12 | 112888210 | 112888210 |
| PTPN11 | 13034 | c.1472C > T | Substitution - Missense | 12 | 112926852 | 112926852 |
| PTPN11 | 13027 | c.1508G > C | Substitution - Missense | 12 | 112926888 | 112926888 |
| PTPN11 | 1358900 | c.1519A > G | Substitution - Missense | 12 | 112926899 | 112926899 |
| PTPN11 | 13031 | c.1528C > A | Substitution - Missense | 12 | 112926908 | 112926908 |
| HNF1A | 21471 | c.617G > T | Substitution - Missense | 12 | 121431413 | 121431413 |
| HNF1A | 24900 | c.632A > C | Substitution - Missense | 12 | 121431428 | 121431428 |
| HNF1A | 24832 | c.685C > T | Substitution - Nonsense | 12 | 121431481 | 121431481 |
| HNF1A | 21474 | c.710A > G | Substitution - Missense | 12 | 121431506 | 121431506 |
| HNF1A | 24923 | c.779C > T | Substitution - Missense | 12 | 121432032 | 121432032 |
| HNF1A | 24692 | c.787C > T | Substitution - Missense | 12 | 121432040 | 121432040 |
| HNF1A | 21481 | c.872_873insC | Insertion - Frameshift | 12 | 121432125 | 121432126 |
| FLT3 | 1166729 | c.2516A > G | Substitution - Missense | 13 | 28592629 | 28592629 |
| FLT3 | 783 | c.2503G > T | Substitution - Missense | 13 | 28592642 | 28592642 |
| FLT3 | 25248 | c.2492G > A | Substitution - Missense | 13 | 28592653 | 28592653 |
| FLT3 | 786 | c.2039C > T | Substitution - Missense | 13 | 28602329 | 28602329 |
| FLT3 | 27907 | c.1800_1801ins21 | Insertion - In frame | 13 | 28608255 | 28608256 |
| FLT3 | 19522 | c.1775T > C | Substitution - Missense | 13 | 28608281 | 28608281 |
| FLT3 | 28042 | c.1352C > T | Substitution - Missense | 13 | 28610138 | 28610138 |
| RB1 | 890 | c.409G > T | Substitution - Nonsense | 13 | 48919244 | 48919244 |
| RB1 | 915 | c.596T > A | Substitution - Nonsense | 13 | 48923148 | 48923148 |
| RB1 | 28816 | c.940 − 2A > T | Unknown | 13 | 48941628 | 48941628 |
| RB1 | 891 | c.958C > T | Substitution - Nonsense | 13 | 48941648 | 48941648 |
| RB1 | 1367204 | c.968A > G | Substitution - Missense | 13 | 48941658 | 48941658 |
| RB1 | 1367206 | c.982A > G | Substitution - Missense | 13 | 48941672 | 48941672 |
| RB1 | 879 | c.1072C > T | Substitution - Nonsense | 13 | 48942685 | 48942685 |
| RB1 | 895 | c.1363C > T | Substitution - Nonsense | 13 | 48953760 | 48953760 |
| RB1 | 887 | c.1654C > T | Substitution - Nonsense | 13 | 48955538 | 48955538 |
| RB1 | 888 | c.1666C > T | Substitution - Nonsense | 13 | 48955550 | 48955550 |
| RB1 | 1367255 | c.1687T > C | Substitution - Missense | 13 | 48955571 | 48955571 |
| RB1 | 892 | c.1735C > T | Substitution - Nonsense | 13 | 49027168 | 49027168 |
| RB1 | 35483 | c.1814 + 2T > C | Unknown | 13 | 49027249 | 49027249 |
| RB1 | 870 | c.2028_2040del13 | Deletion - Frameshift | 13 | 49033891 | 49033903 |
| RB1 | 13117 | c.2053C > T | Substitution - Nonsense | 13 | 49033916 | 49033916 |
| RB1 | 942 | c.2063T > C | Substitution - Missense | 13 | 49033926 | 49033926 |
| RB1 | 1042 | c.2107 − 2A > G | Unknown | 13 | 49037865 | 49037865 |
| RB1 | 883 | c.2117G > T | Substitution - Missense | 13 | 49037877 | 49037877 |
| RB1 | 940 | c.2143A > T | Substitution - Nonsense | 13 | 49037903 | 49037903 |
| RB1 | 1367309 | c.2153A > G | Substitution - Missense | 13 | 49037913 | 49037913 |
| RB1 | 868 | c.2242G > T | Substitution - Nonsense | 13 | 49039164 | 49039164 |
| RB1 | 916 | c.2261T > G | Substitution - Missense | 13 | 49039183 | 49039183 |
| RB1 | 551465 | c.2267A > G | Substitution - Missense | 13 | 49039189 | 49039189 |
| RB1 | 254910 | c.2293A > T | Substitution - Nonsense | 13 | 49039215 | 49039215 |
| AKT1 | 33765 | c.49G > A | Substitution - Missense | 14 | 105246551 | 105246551 |
| IDH2 | 33733 | c.515G > A | Substitution - Missense | 15 | 90631838 | 90631838 |
| IDH2 | 1375400 | c.474A > G | Substitution - coding silent | 15 | 90631879 | 90631879 |
| IDH2 | 41590 | c.419G > A | Substitution - Missense | 15 | 90631934 | 90631934 |
| CDH1 | 1379165 | c.1058A > G | Substitution - Missense | 16 | 68846087 | 68846087 |
| CDH1 | 19748 | c.1108G > C | Substitution - Missense | 16 | 68846137 | 68846137 |
| CDH1 | 19750 | c.1204G > A | Substitution - Missense | 16 | 68847282 | 68847282 |

TABLE 1A-continued

Exemplary Hotspot (HS) Variants

| Gene name | Mutation ID | Mutation CDS | Mutation Description | Chr | Start | End |
|---|---|---|---|---|---|---|
| CDH1 | 25267 | c.1733_1734insC | Insertion - Frameshift | 16 | 68855925 | 68855926 |
| CDH1 | 19746 | c.1742T > C | Substitution - Missense | 16 | 68855934 | 68855934 |
| CDH1 | 19758 | c.1774G > A | Substitution - Missense | 16 | 68855966 | 68855966 |
| CDH1 | 19743 | c.1849G > A | Substitution - Missense | 16 | 68856041 | 68856041 |
| CDH1 | 19822 | c.1901C > T | Substitution - Missense | 16 | 68856093 | 68856093 |
| CDH1 | 19418 | c.1913G > A | Substitution - Nonsense | 16 | 68856105 | 68856105 |
| TP53 | 13747 | c.1146delA | Deletion - Frameshift | 17 | 7572963 | 7572963 |
| TP53 | 307348 | c.1123C > T | Substitution - Nonsense | 17 | 7572986 | 7572986 |
| TP53 | 1191161 | c.1101 − 2A > G | Unknown | 17 | 7573010 | 7573010 |
| TP53 | 11073 | c.1024C > T | Substitution - Nonsense | 17 | 7574003 | 7574003 |
| TP53 | 11286 | c.1015G > T | Substitution - Nonsense | 17 | 7574012 | 7574012 |
| TP53 | 11071 | c.1009C > T | Substitution - Missense | 17 | 7574018 | 7574018 |
| TP53 | 11514 | c.1001G > T | Substitution - Missense | 17 | 7574026 | 7574026 |
| TP53 | 11354 | c.991C > T | Substitution - Nonsense | 17 | 7576855 | 7576855 |
| TP53 | 44823 | c.981T > G | Substitution - Nonsense | 17 | 7576865 | 7576865 |
| TP53 | 46088 | c.963A > G | Substitution - coding silent | 17 | 7576883 | 7576883 |
| TP53 | 10786 | c.949C > T | Substitution - Nonsense | 17 | 7576897 | 7576897 |
| TP53 | 10663 | c.916C > T | Substitution - Nonsense | 17 | 7577022 | 7577022 |
| TP53 | 10710 | c.892G > T | Substitution - Nonsense | 17 | 7577046 | 7577046 |
| TP53 | 10863 | c.833C > T | Substitution - Missense | 17 | 7577105 | 7577105 |
| TP53 | 10660 | c.818G > A | Substitution - Missense | 17 | 7577120 | 7577120 |
| TP53 | 10662 | c.743G > A | Substitution - Missense | 17 | 7577538 | 7577538 |
| TP53 | 6932 | c.733G > A | Substitution - Missense | 17 | 7577548 | 7577548 |
| TP53 | 10812 | c.722C > T | Substitution - Missense | 17 | 7577559 | 7577559 |
| TP53 | 10725 | c.701A > G | Substitution - Missense | 17 | 7577580 | 7577580 |
| TP53 | 10758 | c.659A > G | Substitution - Missense | 17 | 7578190 | 7578190 |
| TP53 | 44317 | c.653T > A | Substitution - Missense | 17 | 7578196 | 7578196 |
| TP53 | 10667 | c.646G > A | Substitution - Missense | 17 | 7578203 | 7578203 |
| TP53 | 43947 | c.614A > G | Substitution - Missense | 17 | 7578235 | 7578235 |
| TP53 | 10738 | c.542G > A | Substitution - Missense | 17 | 7578388 | 7578388 |
| TP53 | 10808 | c.488A > G | Substitution - Missense | 17 | 7578442 | 7578442 |
| TP53 | 10739 | c.481G > A | Substitution - Missense | 17 | 7578449 | 7578449 |
| TP53 | 10670 | c.469G > T | Substitution - Missense | 17 | 7578461 | 7578461 |
| TP53 | 10801 | c.404G > A | Substitution - Missense | 17 | 7578526 | 7578526 |
| TP53 | 11582 | c.395A > G | Substitution - Missense | 17 | 7578535 | 7578535 |
| TP53 | 11462 | c.388C > G | Substitution - Missense | 17 | 7578542 | 7578542 |
| TP53 | 44226 | c.380C > T | Substitution - Missense | 17 | 7578550 | 7578550 |
| TP53 | 44985 | c.375 + 17G > A | Unknown | 17 | 7579295 | 7579295 |
| TP53 | 43904 | c.375G > A | Substitution - coding silent | 17 | 7579312 | 7579312 |
| TP53 | 10716 | c.329G > T | Substitution - Missense | 17 | 7579358 | 7579358 |
| TP53 | 46103 | c.319T > G | Substitution - Missense | 17 | 7579368 | 7579368 |
| TP53 | 44492 | c.273G > A | Substitution - Nonsense | 17 | 7579414 | 7579414 |
| TP53 | 43910 | c.245C > T | Substitution - Missense | 17 | 7579442 | 7579442 |
| TP53 | 12168 | c.166G > T | Substitution - Nonsense | 17 | 7579521 | 7579521 |
| TP53 | 44907 | c.151G > T | Substitution - Nonsense | 17 | 7579536 | 7579536 |
| TP53 | 43664 | c.134T > C | Substitution - Missense | 17 | 7579553 | 7579553 |
| TP53 | 46286 | c.112C > T | Substitution - Nonsense | 17 | 7579575 | 7579575 |
| TP53 | 85573 | c.80delC | Deletion - Frameshift | 17 | 7579716 | 7579716 |
| ERBB2 | 14060 | c.2264T > C | Substitution - Missense | 17 | 37880220 | 37880220 |
| ERBB2 | 1251412 | c.2305G > T | Substitution - Missense | 17 | 37880261 | 37880261 |
| ERBB2 | 20959 | c.2324_2325ins12 | Insertion - In frame | 17 | 37880995 | 37880996 |
| ERBB2 | 14065 | c.2524G > A | Substitution - Missense | 17 | 37881332 | 37881332 |
| ERBB2 | 686 | c.2570A > G | Substitution - Missense | 17 | 37881378 | 37881378 |
| ERBB2 | 21985 | c.2632C > T | Substitution - Missense | 17 | 37881440 | 37881440 |
| SMAD4 | 1389031 | c.306T > C | Substitution - coding silent | 18 | 48575112 | 48575112 |
| SMAD4 | 14229 | c.377T > C | Substitution - Missense | 18 | 48575183 | 48575183 |
| SMAD4 | 218557 | c.389C > T | Substitution - Missense | 18 | 48575195 | 48575195 |
| SMAD4 | 14168 | c.403C > T | Substitution - Nonsense | 18 | 48575209 | 48575209 |
| SMAD4 | 13115 | c.431C > G | Substitution - Missense | 18 | 48575671 | 48575671 |
| SMAD4 | 14118 | c.502G > T | Substitution - Nonsense | 18 | 48581198 | 48581198 |
| SMAD4 | 1226725 | c.533C > A | Substitution - Nonsense | 18 | 48581229 | 48581229 |
| SMAD4 | 308153 | c.547C > T | Substitution - Nonsense | 18 | 48581243 | 48581243 |
| SMAD4 | 14057 | c.733C > T | Substitution - Nonsense | 18 | 48584560 | 48584560 |
| SMAD4 | 22901 | c.766C > T | Substitution - Nonsense | 18 | 48584593 | 48584593 |
| SMAD4 | 14217 | c.776_777delCT | Deletion - Frameshift | 18 | 48584603 | 48584604 |
| SMAD4 | 14163 | c.931C > T | Substitution - Nonsense | 18 | 48586262 | 48586262 |
| SMAD4 | 14167 | c.955 + 5G > C | Unknown | 18 | 48586291 | 48586291 |
| SMAD4 | 1389054 | c.1001A > G | Substitution - Missense | 18 | 48591838 | 48591838 |
| SMAD4 | 1389057 | c.1010A > G | Substitution - Missense | 18 | 48591847 | 48591847 |
| SMAD4 | 14109 | c.1018A > G | Substitution - Missense | 18 | 48591855 | 48591855 |
| SMAD4 | 14111 | c.1028C > G | Substitution - Missense | 18 | 48591865 | 48591865 |
| SMAD4 | 14249 | c.1156G > C | Substitution - Missense | 18 | 48593405 | 48593405 |
| SMAD4 | 14103 | c.1216G > A | Substitution - Missense | 18 | 48593465 | 48593465 |
| SMAD4 | 14223 | c.1229_1230insCA | Insertion - Frameshift | 18 | 48593478 | 48593479 |
| SMAD4 | 1389077 | c.1248A > G | Substitution - coding silent | 18 | 48593497 | 48593497 |
| SMAD4 | 14096 | c.1333C > T | Substitution - Nonsense | 18 | 48603032 | 48603032 |

TABLE 1A-continued

Exemplary Hotspot (HS) Variants

| Gene name | Mutation ID | Mutation CDS | Mutation Description | Chr | Start | End |
|---|---|---|---|---|---|---|
| SMAD4 | 14114 | c.1504A > G | Substitution - Missense | 18 | 48604682 | 48604682 |
| SMAD4 | 1389099 | c.1519A > G | Substitution - Missense | 18 | 48604697 | 48604697 |
| SMAD4 | 14134 | c.1576G > T | Substitution - Nonsense | 18 | 48604754 | 48604754 |
| SMAD4 | 1389106 | c.1591C > A | Substitution - coding silent | 18 | 48604769 | 48604769 |
| STK11 | 21212 | c.169delG | Deletion - Frameshift | 19 | 1207077 | 1207077 |
| STK11 | 21570 | c.465 – 1G > T | Unknown | 19 | 1220371 | 1220371 |
| STK11 | 27316 | c.475C > T | Substitution - Nonsense | 19 | 1220382 | 1220382 |
| STK11 | 20944 | c.580G > T | Substitution - Missense | 19 | 1220487 | 1220487 |
| STK11 | 25229 | c.595G > T | Substitution - Nonsense | 19 | 1220502 | 1220502 |
| STK11 | 29005 | c.816C > T | Substitution - coding silent | 19 | 1221293 | 1221293 |
| STK11 | 21355 | c.842C > T | Substitution - Missense | 19 | 1221319 | 1221319 |
| STK11 | 21360 | c.1062C > G | Substitution - Missense | 19 | 1223125 | 1223125 |
| GNA11 | 21651 | c.547C > T | Substitution - Missense | 19 | 3115012 | 3115012 |
| GNA11 | 52969 | c.626A > T | Substitution - Missense | 19 | 3118942 | 3118942 |
| JAK3 | 34213 | c.2164G > A | Substitution - Missense | 19 | 17945696 | 17945696 |
| JAK3 | 34214 | c.1715C > T | Substitution - Missense | 19 | 17948009 | 17948009 |
| SRC | 1227526 | c.1460C > T | Substitution - Missense | 20 | 36031630 | 36031631 |
| GNAS | 244725 | c.489C > T | Substitution - coding silent | 20 | 57480494 | 57480494 |
| GNAS | 27887 | c.601C > T | Substitution - Missense | 20 | 57484420 | 57484420 |
| GNAS | 27888 | c.680A > T | Substitution - Missense | 20 | 57484596 | 57484596 |
| SMARCB1 | 1002 | c.118C > T | Substitution - Nonsense | 22 | 24133967 | 24133967 |
| SMARCB1 | 991 | c.141C > A | Substitution - Nonsense | 22 | 24133990 | 24133990 |
| SMARCB1 | 24595 | c.157C > T | Substitution - Nonsense | 22 | 24134006 | 24134006 |
| SMARCB1 | 992 | c.472C > T | Substitution - Nonsense | 22 | 24143240 | 24143240 |
| SMARCB1 | 51386 | c.566_567ins19 | Insertion - Frameshift | 22 | 24145547 | 24145548 |
| SMARCB1 | 993 | c.601C > T | Substitution - Nonsense | 22 | 24145582 | 24145582 |
| SMARCB1 | 999 | c.607G > A | Substitution - Missense | 22 | 24145588 | 24145588 |
| SMARCB1 | 1057 | c.1148delC | Deletion - Frameshift | 22 | 24176357 | 24176357 |

TABLE 1B

Exemplary Copy Number Variants (CNV)

| Gene Name | Chromosome | Start | End |
|---|---|---|---|
| ERBB2 | chr17 | 37845134 | 37845207 |
| ERBB2 | chr17 | 37852282 | 37852381 |
| ERBB2 | chr17 | 37860184 | 37860303 |
| ERBB2 | chr17 | 37871503 | 37871582 |
| ERBB2 | chr17 | 37876682 | 37876784 |
| ERBB2 | chr17 | 37884464 | 37884584 |
| ERBB2 | chr17 | 37854903 | 37855025 |
| ERBB2 | chr17 | 37884065 | 37884183 |
| ERBB2 | chr17 | 37866483 | 37866606 |
| ERBB2 | chr17 | 37880963 | 37881086 |
| KRAS | chr12 | 25378600 | 25378682 |
| PDGFRA | chr4 | 55140973 | 55141093 |

TABLE 2

| | Control Reagent* | | | | | | | |
|---|---|---|---|---|---|---|---|---|
| Sequence | A | B | C | D | E | F | G | H |
| 1 | CSF1R | APC | APC | APC | APC | CSF1R | APC | APC |
| 2 | EGFR | EGFR | CSF1R | CSF1R | CSF1R | EGFR | EGFR | CSF1R |
| 3 | FBXW7 | FBXW7 | EGFR | FGFR3 | EGFR | FGFR1 | FGFR3 | EGFR |
| 4 | FGFR3 | FGFR3 | ERBB4 | FLT3 | FBXW7 | FGFR3 | FLT3 | FGFR3 |
| 5 | FLT3 | FLT3 | FGFR3 | KDR | FGFR3 | FLT3 | HRAS | FLT3 |
| 6 | GNA11 | KDR | FLT3 | KRAS | FLT3 | HRAS | IDH1 | HRAS |
| 7 | HNF1A | KRAS | HRAS | PDGFRA | HRAS | KDR | KDR | IDH1 |
| 8 | HRAS | PDGFRA | KDR | RET | KRAS | KIT | KRAS | KRAS |
| 9 | PDGFRA | PIK3CA | KIT | STK11 | PDGFRA | KRAS | PDGFRA | PDGFRA |
| 10 | PIK3CA | RET | KRAS | TP53 | RET | MET | RET | PIK3CA |
| 11 | RET | TP53 | PDGFRA | — | SMAD4 | NOTCH1 | TP53 | RET |
| 12 | STK11 | — | RET | — | TP53 | PDGFRA | — | STK11 |
| 13 | TP53 | — | SMAD4 | — | — | PIK3CA | — | TP53 |
| 14 | VHL | — | TP53 | — | — | SMARCB1 | — | — |

TABLE 2-continued

| | Control Reagent* | | | | | | | |
|---|---|---|---|---|---|---|---|---|
| Sequence | A | B | C | D | E | F | G | H |
| 15 | — | — | — | — | — | SMO | — | — |
| 16 | — | — | — | — | — | TP53 | — | — |

*APC (Adenomatous polyposis coli, deleted in polyposis 2.5 (DP2.5); Chr. 5: 112.04-112.18 Mb; Ref. Seq. NM_000038 and NP_000029), CSF1R (Colony stimulating factor 1 receptor, macrophage colony-stimulating factor receptor (M-CSFR), CD115; Chr. 5, 149.43-149.49 Mb; Ref. Seq. NM_005211 and NM_005202), EGFR (epidermal growth factor receptor; Chr. 7: 55.09-55.32 Mb; RefSeq Nos. NM_005228 and NP_0052219), FBXW7 (F-box/WD repeat-containing protein 7; Chr. 4: 153.24-153.46 Mb; RefSeq. Nos. NM_001013415 and NP_001013433), FGFR1 (Fibroblast growth factor receptor 1, basic fibroblast growth factor receptor 1, fms-related tyrosine kinase-2/Pfeiffer syndrome, CD331; Chr. 8: 38.27-38.33 Mb; RefSeq. Nos. NM_001174063 and NP_001167534), FGFR3 (Fibroblast growth factor receptor 3, CD333; chr. 4: 1.8-1.81 Mb; RefSeq Nos. NM_000142 and NP_000133), FLT3 (Fms-like tyrosine kinase 3, CD135, fetal liver kinase-2 (Flk2); Chr. 13: 28.58-28.67 Mb; RefSeq Nos. NM_004119 and NP_004110), GNA11 (Guanine nucleotide-binding protein subunit alpha-11; Chr. 19: 3.09-3.12 Mb; RefSeq Nos. NM_002067 and NP_002058), HNF1A (hepatocyte nuclear factor 1 homeobox A; Chr. 12: 121.42-121.44 Mb; RefSeq Nos. NM_000545 and NP_000536), HRAS (GTPase HRas, transforming protein p21; Chr. 11: 0.53-0.54 Mb; RefSeq Nos. NM_001130442 and NP_001123914), IDH1 (Isocitrate dehydrogenase 1 (NADP+), soluble; Chr. 2: 209.1-209.13 Mb; RefSeq Nos. NM_005896 and NP_005887), KDR (Kinase insert domain receptor, vascular endothelial growth factor receptor 2, CD309; Chr. 4: 55.94-55.99 Mb; RefSeq Nos. NM_002253 and NP_002244), KIT (Mast/stem cell growth factor receptor (SCFR), proto-oncogene c-Kit, tyrosine-protein kinase Kit, CD117; Chr. 4: 55.52-55.61 Mb; RefSeq Nos. NM_000222 and NP_000213), KRAS (GTPase KRas, V-Ki-ras2 Kirsten rat sarcoma viral oncogene homolog; Chr. 12: 25.36-25.4 Mb; RefSeq Nos. NM_004985-NP_004976), MET (c-Met, MNNG HOS Transforming gene, hepatocyte growth factor receptor; Chr. 7: 116.31-116.44 Mb; RefSeq Nos. NM_000245 and NP_000236), NOTCH1 (Notch homolog 1, translocation-associated (Drosophila); Chr. 9: 139.39-139.44; RefSeq Nos. NM_017617 and NP_060087), PDGFRA (Alpha-type platelet-derived growth factor receptor; Chr. 4: 55.1-55.16 Mb; RefSeq Nos. NM_006206 and NP_006197), PIK3CA (p110α protein; Chr. 3: 178.87-178.96 Mb; RefSeq Nos. NM_006218 and NP_006209), RET (receptor tyrosine kinase; Chr. 10: 43.57-43.64; RefSeq Nos. NM_000323 and NP_065681), SMAD4 (Chr. 18: 48.49-48.61 Mb; RefSeq Nos. NM_005359 and NP_005350), SMARCB1 (SWI/SNF-related matrix-associated actin-dependent regulator of chromatin subfamily B member 1; Chr. 22: 24.13-24.18 Mb; RefSeq Nos. NM_001007468 and NP_001007469), SMO (Smoothened; Chr. 7: 128.83-128.85 Mb; RefSeq Nos. NM_005631 and NP_005622), STK11 (Serine/threonine kinase 11, liver kinase B1 (LKB1), renal carcinoma antigen NY-REN-19; Chr. 19: 1.19-1.23 Mb; RefSeq Nos. NM_000455 and NP_000446), TP53 (protein 53, tumor protein 53; Chr. 17: 7.57-7.59 Mb; RefSeq Nos. NM_000546 and NP_000537), VHL (Von Hippel-Lindau tumor suppressor; Chr. 3: 10.18-10.19 Mb; RefSeq Nos. NM_000551 and NP_000542).

One or more variants of each of these reference sequences may also be represented in each control sequence and/or control reagent. In some embodiments, for instance, multiple variants may be included for each reference sequence. Panels of reference sequences may also be designed to represent particular metabolic, genetic information processing, environmental information processing, cellular process, organismal system, disease, drug development, or other pathways (e.g., KEGG pathways (http://www.genome.jp/kegg/pathway.html, Nov. 8, 2013)). Control reagents such as these may be assayed separately or combined into a single assay. The control reagents may also be designed to include various amounts of each reference sequences and/or variants thereof.

TABLE 3

| Run ID | Number of Variants Detected | Number of Variants Expected | Detection Rate |
|---|---|---|---|
| Bad Run | 8 | 15 | 53% |
| Bad Run | 12 | 15 | 80% |
| Good Run | 15 | 15 | 100% |

TABLE 3-continued

| Run ID | Number of Variants Detected | Number of Variants Expected | Detection Rate |
|---|---|---|---|
| Good Run | 15 | 15 | 100% |
| Good Run | 15 | 15 | 100% |
| Good Run | 15 | 15 | 100% |
| Good Run | 15 | 15 | 100% |
| Good Run | 15 | 15 | 100% |

TABLE 4

| Fragment ID | # of Variants | Included in Plasmid V1 | Included in Plasmid V2 |
|---|---|---|---|
| EGFR_1 | 1 | Yes | No |
| EGFR_2 | 2 | Yes | No |
| EGFR_3 | 2 | Yes | No |
| EGFR_4 | 13 | Yes | Yes |
| EGFR_5 | 7 | Yes | Yes |
| EGFR_6/7 | 10 | Yes | Yes |
| EGFR_8 | 8 | Yes | Yes |

TABLE 5

| Included variants for each EGFR fragment | | | | | | |
|---|---|---|---|---|---|---|
| EGFR_1 | EGFR_2 | EGFR_3 | EGFR_4 | EGFR_5 | EGFR_6_7 | EGFR_8 |
| COSM21683 | COSM21686 | COSM21689 | COSM41905 | COSM13180 | COSM28603 | COSM6224 |
| | COSM21687 | COSM21690 | COSM28508 | COSM53194 | COSM26445 | COSM12675 |
| | | | COSM28511 | COSM18419 | COSM6241 | COSM6213 |
| | | | COSM12988 | COSM13182 | COSM12376 | COSM14070 |
| | | | COSM13427 | COSM17570 | COSM12381 | COSM28607 |
| | | | COSM41603 | COSM6223 | COSM13007 | COSM33725 |
| | | | COSM28601 | COSM21984 | COSM6240 | COSM13008 |
| | | | COSM6252 | | COSM13192 | COSM26438 |
| | | | COSM6239 | | COSM28610 | |
| | | | COSM12373 | | COSM41663 | |
| | | | COSM22992 | | | |
| | | | COSM28510 | | | |
| | | | COSM13979 | | | |

TABLE 6

Mutation Detail

| Mutation ID | Gene name | Mutation ID | Mutation CDS | Mutation AA | Mutation Description | Chr | Start | End | GRCh37 strand |
|---|---|---|---|---|---|---|---|---|---|
| 21683 | EGFR | 21683 | c.323G > A | p.R108K | Substitution - Missense | 7 | 55211080 | 55211080 | + |
| 21686 | EGFR | 21686 | c.865G > A | p.A289T | Substitution - Missense | 7 | 55221821 | 55221821 | + |
| 21687 | EGFR | 21687 | c.866C > T | p.A289V | Substitution - Missense | 7 | 55221822 | 55221822 | + |
| 21689 | EGFR | 21689 | c.1787C > T | p.P596L | Substitution - Missense | 7 | 55233037 | 55233037 | + |
| 21690 | EGFR | 21690 | c.1793G > T | p.G598V | Substitution - Missense | 7 | 55233043 | 55233043 | + |
| 41905 | EGFR | 41905 | c.2092G > A | p.A698T | Substitution - Missense | 7 | 55241644 | 55241644 | + |
| 28508 | EGFR | 28508 | c.2104G > T | p.A702S | Substitution - Missense | 7 | 55241656 | 55241656 | + |
| 28511 | EGFR | 28511 | c.2108T > C | p.L703P | Substitution - Missense | 7 | 55241660 | 55241660 | + |
| 12988 | EGFR | 12988 | c.2125G > A | p.E709K | Substitution - Missense | 7 | 55241677 | 55241677 | + |
| 13427 | EGFR | 13427 | c.2126A > C | p.E709A | Substitution - Missense | 7 | 55241678 | 55241678 | + |
| 41603 | EGFR | 41603 | c.2134T > C | p.F712L | Substitution - Missense | 7 | 55241686 | 55241686 | + |
| 28601 | EGFR | 28601 | c.2135T > C | p.F712S | Substitution - Missense | 7 | 55241687 | 55241687 | + |
| 6252 | EGFR | 6252 | c.2155G > A | p.G719S | Substitution - Missense | 7 | 55241707 | 55241707 | + |
| 6239 | EGFR | 6239 | c.2156G > C | p.G719A | Substitution - Missense | 7 | 55241708 | 55241708 | + |
| 12373 | EGFR | 12373 | c.2159C > T | p.S720F | Substitution - Missense | 7 | 55241711 | 55241711 | + |
| 22992 | EGFR | 22992 | c.2161G > A | p.G721S | Substitution - Missense | 7 | 55241713 | 55241713 | + |
| 28510 | EGFR | 28510 | c.2162G > C | p.G721A | Substitution - Missense | 7 | 55241714 | 55241714 | + |
| 13979 | EGFR | 13979 | c.2170G > A | p.G724S | Substitution - Missense | 7 | 55241722 | 55241722 | + |
| 13180 | EGFR | 13180 | c.2188C > T | p.L730F | Substitution - Missense | 7 | 55242418 | 55242418 | + |
| 53194 | EGFR | 53194 | c.2197C > T | p.P733S | Substitution - Missense | 7 | 55242427 | 55242427 | + |
| 18419 | EGFR | 18419 | c.2200G > A | p.E734K | Substitution - Missense | 7 | 55242430 | 55242430 | + |
| 13182 | EGFR | 13182 | c.2203G > A | p.G735S | Substitution - Missense | 7 | 55242433 | 55242433 | + |
| 17570 | EGFR | 17570 | c.2222C > T | p.P741L | Substitution - Missense | 7 | 55242452 | 55242452 | + |
| 6223 | EGFR | 6223 | c.2235_2249del15 | p.E746_A750delELREA | Deletion - In frame | 7 | 55242465 | 55242479 | + |
| 21984 | EGFR | 21984 | c.2281G > T | p.D761Y | Substitution - Missense | 7 | 55242511 | 55242511 | + |
| 28603 | EGFR | 28603 | c.2293G > A | p.V765M | Substitution - Missense | 7 | 55248995 | 55248995 | + |
| 26445 | EGFR | 26445 | c.2300C > T | p.A767V | Substitution - Missense | 7 | 55249002 | 55249002 | + |
| 6241 | EGFR | 6241 | c.2303G > T | p.S768I | Substitution - Missense | 7 | 55249005 | 55249005 | + |
| 12376 | EGFR | 12376 | c.2307_2308insGCCAGCGTG | p.V769_D770insASV | Insertion - In frame | 7 | 55249009 | 55249010 | + |
| 12381 | EGFR | 12381 | c.2319_2320insAACCCCCAC | p.H773_V774insNPH | Insertion - In frame | 7 | 55249021 | 55249022 | + |
| 13007 | EGFR | 13007 | c.2335_2336GG > TT | p.G779F | Substitution - Missense | 7 | 55249037 | 55249038 | + |
| 6240 | EGFR | 6240 | c.2369C > T | p.T790M | Substitution - Missense | 7 | 55249071 | 55249071 | + |
| 13192 | EGFR | 13192 | c.2428G > A | p.G810S | Substitution - Missense | 7 | 55249130 | 55249130 | + |
| 28610 | EGFR | 28610 | c.2441T > C | p.L814P | Substitution - Missense | 7 | 55249143 | 55249143 | + |
| 41663 | EGFR | 41663 | c.2462T > C | p.I821T | Substitution - Missense | 7 | 55249164 | 55249164 | + |
| 6224 | EGFR | 6224 | c.2573T > G | p.L858R | Substitution - Missense | 7 | 55259515 | 55259515 | + |
| 12675 | EGFR | 12675 | c.2575G > A | p.A859T | Substitution - Missense | 7 | 55259517 | 55259517 | + |

TABLE 6-continued

Mutation Detail

| Mutation ID | Gene name | Mutation ID | Mutation CDS | Mutation AA | Mutation Description | Chr | Start | End | GRCh37 strand |
|---|---|---|---|---|---|---|---|---|---|
| 6213 | EGFR | 6213 | c.2582T > A | p.L861Q | Substitution - Missense | 7 | 55259524 | 55259524 | + |
| 14070 | EGFR | 14070 | c.2588G > A | p.G863D | Substitution - Missense | 7 | 55259530 | 55259530 | + |
| 28607 | EGFR | 28607 | c.2603A > G | p.E868G | Substitution - Missense | 7 | 55259545 | 55259545 | + |
| 33725 | EGFR | 33725 | c.2609A > G | p.H870R | Substitution - Missense | 7 | 55259551 | 55259551 | + |
| 13008 | EGFR | 13008 | c.2612C > G | p.A871G | Substitution - Missense | 7 | 55259554 | 55259554 | + |
| 26438 | EGFR | 26438 | c.2620G > A | p.G874S | Substitution - Missense | 7 | 55259562 | 55259562 | + |

TABLE 7

Results of EGFR plasmid

| Mutation ID | EGFR Plasmid V1 | | EGFR Plasmid V2 | |
|---|---|---|---|---|
| | Ion AmpliSeq CHP2 | Illumina TruSeq | Ion AmpliSeq CHP2 | Illumina TruSeq |
| 21683 | Called | Called | Not Included | Not Included |
| 21686 | Called | Called | Not Included | Not Included |
| 21687 | Called | Called | Not Included | Not Included |
| 21689 | Called | Not Targeted | Not Included | Not Included |
| 21690 | Called | Called | Not Included | Not Included |
| 41905 | Called | Not Called** | Called | Not Called** |
| 28508 | Called | Not Called** | Called | Not Called** |
| 28511 | Called | Not Called** | Called | Not Called** |
| 12988 | Not Called | Not Called** | Not Called | Not Called** |
| 13427 | Called | Not Called** | Called | Not Called** |
| 41603 | Called | Not Called** | Called | Not Called** |
| 28601 | Called | Not Called** | Called | Not Called** |
| 6252 | Called | Not Called** | Called | Not Called** |
| 6239 | Called | Not Called** | Called | Not Called** |
| 12373 | Not Called | Not Called** | Not Called | Not Called** |
| 22992 | Called | Not Called** | Called | Not Called** |
| 28510 | Called | Not Called** | Called | Not Called** |
| 13979 | Called | Not Called** | Called | Not Called** |
| 13180 | Called | Called | Called | Called |
| 53194 | Called | Called | Called | Called |
| 18419 | Called | Called | Called | Called |
| 13182 | Called | Called | Called | Called |
| 17570 | Called | Called | Called | Called |
| 6223 | Not Called* | Called | Not Called* | Called |
| 21984 | Called | Called | Called | Called |
| 28603 | Called | Called | Called | Called |
| 26445 | Called | Not Called | Called | Not Called |
| 6241 | Called | Not Called | Called | Not Called |
| 12376 | Called | Not Called | Called | Not Called |
| 12381 | Called | Not Called | Called | Not Called |
| 13007 | Called | Called | Called | Called |
| 6240 | Called | Called | Called | Called |
| 13192 | Called | Called | Called | Called |
| 28610 | Called | Called | Called | Called |
| 41663 | Called | Not Called | Called | Not Called |
| 6224 | Called | Not Called | Called | Not Called |
| 12675 | Called | Not Called | Called | Not Called |
| 6213 | Called | Not Called | Called | Not Called |
| 14070 | Called | Not Called | Called | Not Called |
| 28607 | Called | Not Called | Called | Not Called |
| 33725 | Called | Not Called | Called | Not Called |
| 13008 | Called | Not Called | Called | Not Called |
| 26438 | Called | Not Called | Called | Not Called |

*Mutation not called by software, but manual inspection revealed that the sequence corresponded to the correct mutation
**Variant introduced in primer region of test method
Called: sequence variant noted by analysis software
Not Targeted: sequence variant not included in sequence analyzed by the test method

TABLE 8

| Gene | Mutation CDS | Mutation AA | Mutation | 2.8 | 2.8 | 5.4 | 5.4 | 11.0 | 11.0 | 18.4 | 18.4 | 29.5 | 29.5 | 47.9 | 47.9 |
|---|---|---|---|---|---|---|---|---|---|---|---|---|---|---|---|
| BRAF | c. 1359T > C | p. P453P | SNP | | 4.7 | 8.8 | 7 | 14.3 | 15.5 | 24.3 | 27.4 | 39.4 | 39.3 | 59.8 | 58.3 |
| EGFR | c.340G > A | p.E114K | SNP | | 4.7 | 7.5 | 7.8 | 14.5 | 15.4 | 25.3 | 23.9 | 38.6 | 39.3 | 59 | 58.8 |
| EGFR | c.323G > A | p.R108K | SNP | | 5.1 | 7.8 | 7.9 | 15 | 14.8 | 26.7 | 25.3 | 40.4 | 39.3 | 59 | 59.2 |
| BRAF | c. 1380A > G | p.G460G | SNP | | 4.8 | 8.7 | 7 | 14.9 | 15.5 | 24.2 | 27.4 | 39.3 | 39.2 | 59.5 | 57.8 |
| EGFR | c.874G > T | p.V292L | SNP | | 4.1 | 8.7 | 5.5 | 12.9 | 14.4 | 27.9 | 27.1 | 41.5 | 41.4 | 62.9 | 58.9 |
| EGFR | c.2235_2249del15 | p.E746_A750delELREA | DEL | | | | | 18.3 | 16.8 | 26.2 | 27.7 | 41.4 | 43.6 | 61.2 | 59.5 |
| KRAS | c.111 + 1C > T | p.? | SNP | 4.5 | | 8 | 6.3 | 15.4 | 13.4 | 24.3 | 24.7 | 38.2 | 37.4 | 58.5 | 59.7 |
| EGFR | c.2429G > A | p.G810D | SNP | 3.1 | 5.6 | 8.3 | 6.7 | 12.1 | 14.4 | 25.3 | 25.4 | 36.8 | 40 | 55.1 | 55.7 |
| EGFR | c.2612C > G | p.A871G | SNP | 3.1 | 5.8 | 8 | 7.2 | 13.7 | 17.4 | 24.9 | 27.5 | 39.6 | 40.4 | 61.2 | 60.8 |
| EGFR | c.2208G > A | p.G735S | SNP | 3.4 | 4.7 | 7.8 | 8.5 | 15.9 | 16.2 | 24.8 | 29.6 | 39.8 | 43.5 | 57.9 | 60.7 |
| EGRF | c.2375T > C | p.L792P | SNP | 3.9 | 4.2 | 8.6 | 5.7 | 14.6 | 14.5 | 22.1 | 27.2 | 39.2 | 41.1 | 59 | 59.5 |
| EGFR | c.2170G > A | p.G724S | SNP | 3.8 | 5 | 8.8 | 8.6 | 16.7 | 16.9 | 27.9 | 28.6 | 43.1 | 39.1 | 62 | 57.6 |
| EGFR | c.2588G > A | p.G863D | SNP | 3.3 | 5.2 | 8 | 7.1 | 13.9 | 17.4 | 23.8 | 26.9 | 40.4 | 40.3 | 61.6 | 60.5 |
| KRAS | c.104C > T | p.T35I | SNP | 3.9 | 3.7 | 7.8 | 6.9 | 15.4 | 13.6 | 24.4 | 25.8 | 38.5 | 37.4 | 57.7 | 59.8 |
| EGFR | c.2222G > T | p.P741L | SNP | 3.2 | 4.6 | 7.8 | 7.9 | 16.2 | 16.5 | 25.8 | 28.1 | 41.4 | 43.5 | 59.1 | 60.2 |
| KRAS | c.351A > C | p.K117N | SNP | 5.2 | 4.2 | 7.6 | 7.1 | 14.7 | 15.3 | 23 | 24.4 | 38.3 | 46.5 | 55.4 | 61.2 |
| EGFR | c.866C > T | p.A289V | SNP | 3 | 4.2 | 9.3 | 5.6 | 12.8 | 14.6 | 27.9 | 27 | 44.2 | 41.4 | 62.9 | 57.6 |
| EGFR | c.1793G > T | p.G598V | SNP | 4.2 | 5.5 | 7 | 6.6 | 14.3 | 16.1 | 23.6 | 24.7 | 38 | 41.8 | 54.8 | 58.3 |
| EGFR | c.2293G > A | p.V765M | SNP | 3.9 | 4.3 | 8.8 | 5.5 | 14.6 | 14.3 | 223 | 27.6 | 39.3 | 40.8 | 58.9 | 59.9 |

TABLE 8-continued

| Gene | Mutation CDS | Mutation AA | Mutation | 2.8 | 2.8 | 5.4 | 5.4 | 11.0 | 11.0 | 18.4 | 18.4 | 29.5 | 29.5 | 47.9 | 47.9 |
|---|---|---|---|---|---|---|---|---|---|---|---|---|---|---|---|
| EGFR | c.2441T > C | p.L814P | SNP | 3.1 | 6.6 | 9.3 | 6.8 | 12 | 16.2 | 26.1 | 25.8 | 37.5 | 41.5 | 55.6 | 58.7 |
| EGFR | c.2092G > A | p.A698T | SNP | 3.7 | 5.2 | 9.1 | 8.9 | 16.6 | 17.1 | 28.2 | 28.8 | 41 | 38.5 | 62.5 | 58.5 |
| BRAF | c.1391G > T | p.G464V | SNP | 2.7 | 4.6 | 8.7 | 7 | 14.5 | 15.4 | 24.1 | 27 | 39.4 | 39.2 | 59.4 | 57.8 |
| BRAF | c.1742A > G | p.N581S | SNP | 3.7 | 4.9 | 8.9 | 8.2 | 12.4 |  | 25.1 | 28.6 | 39.3 | 43.9 | 59.4 | 57.2 |
| BRAF | c.1781A < G | p.D594G | SNP | 4 | 4.8 | 8.3 | 8.4 | 12.3 |  | 25.7 | 28.4 | 39.7 | 43.8 | 58.2 | 57.2 |
| BRAF | c.1790T > G | p.L597T | SNP | 3.6 | 4.7 | 8.1 | 8.3 | 12.3 |  | 25.9 | 28.6 | 38.6 | 44 | 57.1 | 57.4 |
| BRAF | c.1799T > A | p.V600E | SNP | 4 | 4.7 | 8.6 | 8.3 | 12.2 |  | 26.4 | 28.6 | 39 | 43.9 | 58 | 57.4 |
| KRAS | c.24A > G | p.V8V | SNP | 4.7 | 3 | 8.3 | 6.7 | 14.8 | 13.2 | 25 | 24.3 | 37 | 36.7 | 56.2 | 59.1 |
| KRAS | c.35G > A | p.G12D | SNP | 4.6 | 3.4 | 8.1 | 6.8 | 15.2 | 12.8 | 24.5 | 24.5 | 36 | 36.7 | 57.4 | 60 |
| EGFR | c.2197C > T | p.P733S | SNP | 3.5 | 5.2 | 8 | 7.5 | 16 | 16.8 | 24.8 | 28.1 | 40.9 | 43.6 | 59 | 60.1 |
| KRAS | c.175G > A | p.A59T | SNP | 4.5 | 4.4 | 8.3 | 6.5 | 15.6 | 14.2 | 24 | 26.4 | 38.1 | 40.9 | 58.6 | 60.7 |
| KRAS | c.183A > C | p.Q61H | SNP | 4.5 | 4.5 | 7.5 | 7 | 15.5 | 14.3 | 23.2 | 26.9 | 40.3 | 40.8 | 60.5 | 61 |
| EGFR | c.2582T > A | p.L861Q | SNP | 2.7 | 5.7 | 8.2 | 6.7 | 13.8 | 17.2 | 23.8 | 27.1 | 39.9 | 40.2 | 60.6 | 60.4 |
| EGFR | c.2573T > G | p.L858R | SNP | 2.7 | 5.3 | 8.4 | 7.1 | 13.8 | 17.1 | 22.9 | 26 | 39.8 | 40.1 | 60.7 | 60.6 |
| EGFR | c.2156G > C | p.G719A | SNP | 3.6 | 5.4 | 9.3 | 8.4 | 16.6 | 16.5 | 27.9 | 29.3 | 42.5 | 38.7 | 62.4 | 57.8 |
| BRAF | c.1330C > T | p.R444W | SNP | 2.9 | 4.5 | 8.6 | 6.7 | 14.5 | 15.6 | 24.4 | 27.9 | 38 | 39.2 | 60.2 | 59.3 |

TABLE 9

| Chromosome | Position | Reference |
|---|---|---|
| 1 | 43814979 | G |
| 1 | 43815009 | G |
| 1 | 43815020 | G |
| 1 | 115256529 | T |
| 1 | 115256537 | T |
| 1 | 115256669 | G |
| 1 | 115258730 | C |
| 1 | 115258747 | C |
| 1 | 115258753 | C |
| 2 | 29432664 | C |
| 2 | 29443695 | G |
| 2 | 48030632 | G |
| 2 | 48030639 | AC |
| 2 | 48030686 | G |
| 2 | 48030838 | A |
| 2 | 209113112 | C |
| 2 | 209113119 | T |
| 2 | 209113140 | C |
| 2 | 212288955 | C |
| 2 | 212288964 | C |
| 2 | 212530084 | C |
| 2 | 212530091 | G |
| 2 | 212530135 | T |
| 2 | 212576810 | A |
| 2 | 212576877 | G |
| 2 | 212576896 | C |
| 2 | 212578348 | A |

TABLE 9-continued

| Chromosome | Position | Alternate |
|---|---|---|
| 2 | 212578372 | A |
| 2 | 212587172 | G |
| 2 | 212587197 | G |
| 2 | 212589812 | T |
| 2 | 212589838 | G |
| 2 | 212589909 | C |

| Chromosome | Position | Alternate |
|---|---|---|
| 1 | 43814979 | A |
| 1 | 43815009 | T |
| 1 | 43815020 | A |
| 1 | 115256529 | C |
| 1 | 115256537 | C |
| 1 | 115256669 | A |
| 1 | 115258730 | T |
| 1 | 115258747 | T |
| 1 | 115258753 | T |
| 2 | 29432664 | T |
| 2 | 29443695 | T |
| 2 | 48030632 | T |
| 2 | 48030639 | A |
| 2 | 48030686 | A |
| 2 | 48030838 | T |
| 2 | 209113112 | T |
| 2 | 209113119 | C |
| 2 | 209113140 | T |
| 2 | 212288955 | A |
| 2 | 212288964 | A |
| 2 | 212530084 | T |
| 2 | 212530091 | T |
| 2 | 212530135 | C |
| 2 | 212576810 | G |
| 2 | 212576877 | A |
| 2 | 212576896 | A |
| 2 | 212578348 | G |
| 2 | 212578372 | C |
| 2 | 212587172 | T |
| 2 | 212587197 | T |
| 2 | 212589812 | C |
| 2 | 212589838 | A |
| 2 | 212589909 | T |

TABLE 9-continued

| Chromosome | Position | Length | Mutation ID | Gene |
|---|---|---|---|---|
| 1 | 43814979 | 1 | COSM27286 | MPL |
| 1 | 43815009 | 1 | COSM18918 | MPL |
| 1 | 43815020 | 1 | COSM27290 | MPL |
| 1 | 115256529 | 1 | COSM584 | NRAS |
| 1 | 115256537 | 1 | COSM1332933 | NRAS |
| 1 | 115256669 | 1 | gDNA31 | NRAS |
| 1 | 115258730 | 1 | COSM577 | NRAS |
| 1 | 115258747 | 1 | COSM564 | NRAS |
| 1 | 115258753 | 1 | COSM24850 | NRAS |
| 2 | 29432664 | 1 | COSM28056 | ALK |
| 2 | 29443695 | 1 | COSM28055 | ALK |
| 2 | 48030632 | 1 | COSM13399 | MSH6 |
| 2 | 48030639 | 1 | COSM13395 | MSH6 |
| 2 | 48030686 | 1 | COSM1021299 | MSH6 |
| 2 | 48030838 | 1 | gDNA32 | MSH6 |
| 2 | 209113112 | 1 | COSM28746 | IDH1 |
| 2 | 209113119 | 1 | COSM1404902 | IDH1 |
| 2 | 209113140 | 1 | COSM96922 | IDH1 |
| 2 | 212288955 | 1 | COSM48362 | ERBB4 |
| 2 | 212288964 | 1 | COSM169572 | ERBB4 |
| 2 | 212530084 | 1 | COSM232263 | ERBB4 |
| 2 | 212530091 | 1 | COSM573362 | ERBB4 |
| 2 | 212530135 | 1 | COSM1405173 | ERBB4 |
| 2 | 212576810 | 1 | COSM1614287 | ERBB4 |
| 2 | 212576877 | 1 | COSM110095 | ERBB4 |
| 2 | 212576896 | 1 | COSM573356 | ERBB4 |
| 2 | 212578348 | 1 | COSM1405181 | ERBB4 |
| 2 | 212578372 | 1 | COSM160825 | ERBB4 |
| 2 | 212587172 | 1 | COSM1015994 | ERBB4 |
| 2 | 212587197 | 1 | COSM1251447 | ERBB4 |
| 2 | 212589812 | 1 | COSM1405184 | ERBB4 |
| 2 | 212589838 | 1 | COSM573353 | ERBB4 |
| 2 | 212589909 | 1 | COSM1015997 | ERBB4 |

| Chromosome | Position | Mutation CDS |
|---|---|---|
| 1 | 43814979 | c.1514G > A |
| 1 | 43815009 | c.1544G > T |
| 1 | 43815020 | c.1555G > A |
| 1 | 115256529 | c.182A > G |
| 1 | 115256537 | c.174A > G |

TABLE 9-continued

| | | | |
|---|---|---|---|
| 1 | 115256669 | | c.112 − 70C > T |
| 1 | 115258730 | | c.52G > A |
| 1 | 115258747 | | c.35G > A |
| 1 | 115258753 | | c.29G > A |
| 2 | 29432664 | | c.3824G > A |
| 2 | 29443695 | | c.3522C > A |
| 2 | 48030632 | | c.3246G > T |
| 2 | 48030639 | | c.3261delC |
| 2 | 48030686 | | c.3300G > A |
| 2 | 48030838 | | c.3438 + 14A > T |
| 2 | 209113112 | | c.395G > A |
| 2 | 209113119 | | c.388A > G |
| 2 | 209113140 | | c.367G > A |
| 2 | 212288955 | | c.2791G > T |
| 2 | 212288964 | | c.2782G > T |
| 2 | 212530084 | | c.1835G > A |
| 2 | 212530091 | | c.1828C > A |
| 2 | 212530135 | | c.1784A > G |
| 2 | 212576810 | | c.1089T > C |
| 2 | 212576877 | | c.1022C > T |
| 2 | 212576896 | | c.1003G > T |
| 2 | 212578348 | | c.909T > C |
| 2 | 212578372 | | c.885T > G |
| 2 | 212587172 | | c.829C > A |
| 2 | 212587197 | | c.804C > A |
| 2 | 212589812 | | c.730A > G |
| 2 | 212589838 | | c.704C > T |
| 2 | 212589909 | | c.633G > A |

| Chromosome | Position | Mutation AA | Mutation Type | Strand | Target Frequency | Sanger Detection* | CHPv2 Detection |
|---|---|---|---|---|---|---|---|
| 1 | 43814979 | p.S505N | SNV | + | 5-15% | Detected | Detected |
| 1 | 43815009 | p.W515L | SNV | + | 5-15% | Detected | Detected |
| 1 | 43815020 | p.A519T | SNV | + | 5-15% | Detected | Detected |
| 1 | 115256529 | p.Q61R | SNV | − | 5-15% | Detected | Detected |
| 1 | 115256537 | p.T58T | SNV | − | 5-15% | Detected | Detected |
| 1 | 115256669 | p.(=) | SNV | − | genomic | Not Covered | Not Covered |
| 1 | 115258730 | p.A18T | SNV | − | 5-15% | Detected | Detected |
| 1 | 115258747 | p.G12D | SNV | − | 5-15% | Detected | Detected |
| 1 | 115258753 | p.G10E | SNV | − | 5-15% | Detected | Detected |
| 2 | 29432664 | p.R1275Q | SNV | − | 5-15% | Detected | Detected |

TABLE 9-continued

| | | | | | | | |
|---|---|---|---|---|---|---|---|
| 2 | 29443695 | p.F1174L | SNV | − | 5-15% | Detected | Detected |
| 2 | 48030632 | p.P1082P | SNV | + | 5-15% | Detected | Not Covered |
| 2 | 48030639 | p.F1088fs*2 | DEL | + | 5-15% | Detected | Not Covered |
| 2 | 48030686 | p.T1100T | SNV | + | 5-15% | Detected | Not Covered |
| 2 | 48030838 | p.(=) | SNV | + | genomic | Not Covered | Not Covered |
| 2 | 209113112 | p.R132H | SNV | − | 5-15% | Detected | Detected |
| 2 | 209113119 | p.I130V | SNV | − | 5-15% | Detected | Detected |
| 2 | 209113140 | p.G123R | SNV | − | 5-15% | Detected | Detected |
| 2 | 212288955 | p.D931Y | SNV | − | 5-15% | Detected | Detected |
| 2 | 212288964 | p.E928* | SNV | − | 5-15% | Detected | Detected |
| 2 | 212530084 | p.R612Q | SNV | − | 5-15% | Detected | Detected |
| 2 | 212530091 | p.P610T | SNV | − | 5-15% | Detected | Detected |
| 2 | 212530135 | p.D595G | SNV | − | 5-15% | Detected | Detected |
| 2 | 212576810 | p.N363N | SNV | − | 5-15% | Detected | Detected |
| 2 | 212576877 | p.S341L | SNV | − | 5-15% | Detected | Detected |
| 2 | 212576896 | p.D335Y | SNV | − | 5-15% | Detected | Detected |
| 2 | 212578348 | p.S303S | SNV | − | 5-15% | Detected | Detected |
| 2 | 212578372 | p.H295Q | SNV | − | 5-15% | Detected | Detected |
| 2 | 212587172 | p.H277N | SNV | − | 5-15% | Detected | Detected |
| 2 | 212587197 | p.Y268* | SNV | − | 5-15% | Detected | Detected |
| 2 | 212589812 | p.T244A | SNV | − | 5-15% | Detected | Detected |
| 2 | 212589838 | p.A235V | SNV | − | 5-15% | Detected | Detected |
| 2 | 212589909 | p.T211T | SNV | − | 5-15% | Detected | Not Covered |

| Chromosome | Position | TSACP Detection | TSTP Detection |
|---|---|---|---|
| 1 | 43814979 | Not Covered | Not Covered |
| 1 | 43815009 | Detected | Not Covered |
| 1 | 43815020 | Detected | Not Covered |
| 1 | 115256529 | Detected | Detected |
| 1 | 115256537 | Detected | Detected |
| 1 | 115256669 | Not Covered | Detected |
| 1 | 115258730 | Detected | Detected |
| 1 | 115258747 | Detected | Detected |
| 1 | 115258753 | Detected | Detected |
| 2 | 29432664 | Detected | Not Covered |
| 2 | 29443695 | Detected | Detected |
| 2 | 48030632 | Not Covered | Detected |
| 2 | 48030639 | Not Covered | Detected |

TABLE 9-continued

| | | | |
|---|---|---|---|
| 2 | 48030686 | Not Covered | Detected |
| 2 | 48030838 | Not Covered | Detected |
| 2 | 209113112 | Detected | Not Covered |
| 2 | 209113119 | Detected | Not Covered |
| 2 | 209113140 | Detected | Not Covered |
| 2 | 212288955 | Detected | Not Covered |
| 2 | 212288964 | Detected | Not Covered |
| 2 | 212530084 | Detected | Not Covered |
| 2 | 212530091 | Detected | Not Covered |
| 2 | 212530135 | Detected | Not Covered |
| 2 | 212576810 | Not Covered | Not Covered |
| 2 | 212576877 | Detected | Not Covered |
| 2 | 212576896 | Detected | Not Covered |
| 2 | 212578348 | Detected | Not Covered |
| 2 | 212578372 | Detected | Not Covered |
| 2 | 212587172 | Detected | Not Covered |
| 2 | 212587197 | Detected | Not Covered |
| 2 | 212589812 | Detected | Not Covered |
| 2 | 212589838 | Detected | Not Covered |
| 2 | 212589909 | Detected | Not Covered |

| Chromosome | Position | Reference |
|---|---|---|
| 2 | 212652764 | T |
| 2 | 212652791 | G |
| 3 | 10183797 | T |
| 3 | 10183808 | G |
| 3 | 10183817 | C |
| 3 | 10183824 | AC |
| 3 | 10188200 | C |
| 3 | 10188210 | T |
| 3 | 10188245 | G |
| 3 | 10188286 | CG |
| 3 | 10191479 | C |
| 3 | 10191488 | C |
| 3 | 10191506 | C |
| 3 | 10191513 | T |
| 3 | 37067240 | T |
| 3 | 41266101 | C |
| 3 | 41266113 | C |
| 3 | 41266124 | A |
| 3 | 41266137 | C |

TABLE 9-continued

| Chromosome | Position | Alternate |
|---|---|---|
| 3 | 138665163 | G |
| 3 | 178916648 | G |
| 3 | 178916706 | A |
| 3 | 178916793 | A |
| 3 | 178916823 | C |
| 3 | 178916936 | G |
| 3 | 178916944 | A |
| 3 | 178916957 | G |
| 3 | 178917661 | A |
| 3 | 178921489 | C |
| 3 | 178921520 | C |
| 3 | 178921553 | T |
| 3 | 178927450 | T |
| 3 | 178927980 | T |

| Chromosome | Position | Alternate |
|---|---|---|
| 2 | 212652764 | C |
| 2 | 212652791 | C |
| 3 | 10183797 | A |
| 3 | 10183808 | C |
| 3 | 10183817 | T |
| 3 | 10183824 | A |
| 3 | 10188200 | A |
| 3 | 10188210 | C |
| 3 | 10188245 | C |
| 3 | 10188286 | C |
| 3 | 10191479 | G |
| 3 | 10191488 | T |
| 3 | 10191506 | T |
| 3 | 10191513 | C |
| 3 | 37067240 | A |
| 3 | 41266101 | G |
| 3 | 41266113 | T |
| 3 | 41266124 | G |
| 3 | 41266137 | T |
| 3 | 138665163 | C |
| 3 | 178916648 | A |
| 3 | 178916706 | G |
| 3 | 178916793 | G |
| 3 | 178916823 | T |
| 3 | 178916936 | A |

TABLE 9-continued

| | | | | |
|---|---|---|---|---|
| | 3 | | 178916944 | G |
| | 3 | | 178916957 | T |
| | 3 | | 178917661 | G |
| | 3 | | 178921489 | T |
| | 3 | | 178921520 | T |
| | 3 | | 178921553 | A |
| | 3 | | 178927450 | C |
| | 3 | | 178927980 | C |

| Chromosome | Position | Length | Mutation ID | Gene |
|---|---|---|---|---|
| 2 | 212652764 | 1 | COSM48369 | ERBB4 |
| 2 | 212652791 | 1 | COSM442267 | ERBB4 |
| 3 | 10183797 | 1 | COSM14305 | VHL |
| 3 | 10183808 | 1 | COSM18080 | VHL |
| 3 | 10183817 | 1 | COSM17658 | VHL |
| 3 | 10183824 | 1 | COSM17886 | VHL |
| 3 | 10188200 | 1 | COSM17752 | VHL |
| 3 | 10188210 | 1 | COSM14312 | VHL |
| 3 | 10188245 | 1 | COSM14407 | VHL |
| 3 | 10188286 | 1 | COSM14412 | VHL |
| 3 | 10191479 | 1 | COSM17657 | VHL |
| 3 | 10191488 | 1 | COSM17612 | VHL |
| 3 | 10191506 | 1 | COSM14311 | VHL |
| 3 | 10191513 | 1 | COSM17837 | VHL |
| 3 | 37067240 | 1 | COSM26085 | MLH1 |
| 3 | 41266101 | 1 | COSM5677 | CTNNB1 |
| 3 | 41266113 | 1 | COSM5662 | CTNNB1 |
| 3 | 41266124 | 1 | COSM5664 | CTNNB1 |
| 3 | 41266137 | 1 | COSM5667 | CTNNB1 |
| 3 | 138665163 | 1 | COSM33661 | FOXL2 |
| 3 | 178916648 | 1 | COSM27495 | PIK3CA |
| 3 | 178916706 | 1 | COSM27376 | PIK3CA |
| 3 | 178916793 | 1 | COSM1420738 | PIK3CA |
| 3 | 178916823 | 1 | COSM1041454 | PIK3CA |
| 3 | 178916936 | 1 | COSM27497 | PIK3CA |
| 3 | 178916944 | 1 | COSM13570 | PIK3CA |
| 3 | 178916957 | 1 | COSM125368 | PIK3CA |
| 3 | 178917661 | 1 | COSM1420774 | PIK3CA |
| 3 | 178921489 | 1 | COSM21462 | PIK3CA |
| 3 | 178921520 | 1 | COSM353193 | PIK3CA |
| 3 | 178921553 | 1 | COSM754 | PIK3CA |

TABLE 9-continued

| | | | | |
|---|---|---|---|---|
| 3 | 178927450 | 1 | COSM1420804 | PIK3CA |
| 3 | 178927980 | 1 | COSM757 | PIK3CA |

| Chromosome | Position | Mutation CDS |
|---|---|---|
| 2 | 212652764 | c.542A > G |
| 2 | 212652791 | c.515C > G |
| 3 | 10183797 | c.266T > A |
| 3 | 10183808 | c.277G > C |
| 3 | 10183817 | c.286C > T |
| 3 | 10183824 | c.296delC |
| 3 | 10188200 | c.343C > A |
| 3 | 10188210 | c.353T > C |
| 3 | 10188245 | c.388G > C |
| 3 | 10188286 | c.431delG |
| 3 | 10191479 | c.472C > G |
| 3 | 10191488 | c.481C > T |
| 3 | 10191506 | c.499C > T |
| 3 | 10191513 | c.506T > C |
| 3 | 37067240 | c.1151T > A |
| 3 | 41266101 | c.98C > G |
| 3 | 41266113 | c.110C > T |
| 3 | 41266124 | c.121A > G |
| 3 | 41266137 | c.134C > T |
| 3 | 138665163 | c.402C > G |
| 3 | 178916648 | c.35G > A |
| 3 | 178916706 | c.93A > G |
| 3 | 178916793 | c.180A > G |
| 3 | 178916823 | c.210C > T |
| 3 | 178916936 | c.323G > A |
| 3 | 178916944 | c.331A > G |
| 3 | 178916957 | c.344G > T |
| 3 | 178917661 | c.536A > G |
| 3 | 178921489 | c.971C > T |
| 3 | 178921520 | c.1002C > T |
| 3 | 178921553 | c.1035T > A |
| 3 | 178927450 | c.1213T > C |
| 3 | 178927980 | c.1258T > C |

| Chromosome | Position | Mutation AA | Mutation Type | Strand | Target Frequency | Sanger Detection* | CHPv2 Detection |
|---|---|---|---|---|---|---|---|
| 2 | 212652764 | p.N181S | SNV | − | 5-15% | Detected | Detected |
| 2 | 212652791 | p.P172R | SNV | − | 5-15% | Detected | Detected |
| 3 | 10183797 | p.L89H | SNV | + | 5-15% | Detected | Detected |

TABLE 9-continued

| | | | | | | | |
|---|---|---|---|---|---|---|---|
| 3 | 10183808 | p.G93R | SNV | + | 5-15% | Detected | Detected |
| 3 | 10183817 | p.Q96* | SNV | + | 5-15% | Detected | Detected |
| 3 | 10183824 | p.P99fs*60 | DEL | + | 5-15% | Detected | Detected |
| 3 | 10188200 | p.H115N | SNV | + | 5-15% | Detected | Detected |
| 3 | 10188210 | p.L118P | SNV | + | 5-15% | Detected | Detected |
| 3 | 10188245 | p.V130L | SNV | + | 5-15% | Detected | Detected |
| 3 | 10188286 | p.G144fs*15 | DEL | + | 5-15% | Detected | Detected |
| 3 | 10191479 | p.L158V | SNV | + | 5-15% | Detected | Detected |
| 3 | 10191488 | p.R161* | SNV | + | 5-15% | Detected | Detected |
| 3 | 10191506 | p.R167W | SNV | + | 5-15% | Detected | Detected |
| 3 | 10191513 | p.L169P | SNV | + | 5-15% | Detected | Detected |
| 3 | 37067240 | p.V384D | SNV | + | 5-15% | Detected | Detected |
| 3 | 41266101 | p.S33C | SNV | + | 5-15% | Detected | Detected |
| 3 | 41266113 | p.S37F | SNV | + | 5-15% | Detected | Detected |
| 3 | 41266124 | p.T41A | SNV | + | 5-15% | Detected | Detected |
| 3 | 41266137 | p.S45F | SNV | + | 5-15% | Detected | Detected |
| 3 | 138665163 | p.C134W | SNV | − | 5-15% | Detected | Not Covered |
| 3 | 178916648 | p.G12D | SNV | + | 5-15% | Detected | Not Covered |
| 3 | 178916706 | p.I31M | SNV | + | 5-15% | Detected | Not Covered |
| 3 | 178916793 | p.Q60Q | SNV | + | 5-15% | Detected | Detected |
| 3 | 178916823 | p.F70F | SNV | + | 5-15% | Detected | Detected |
| 3 | 178916936 | p.R108H | SNV | + | 5-15% | Detected | Detected |
| 3 | 178916944 | p.K111E | SNV | + | 5-15% | Detected | Detected |
| 3 | 178916957 | p.R115L | SNV | + | 5-15% | Detected | Detected |
| 3 | 178917661 | p.K179R | SNV | + | 5-15% | Detected | Not Covered |
| 3 | 178921489 | p.T324I | SNV | + | 5-15% | Detected | Detected |
| 3 | 178921520 | p.L334L | SNV | + | 5-15% | Detected | Detected |
| 3 | 178921553 | p.N345K | SNV | + | 5-15% | Detected | Detected |
| 3 | 178927450 | p.S405P | SNV | + | 5-15% | Detected | Detected |
| 3 | 178927980 | p.C420R | SNV | + | 5-15% | Detected | Detected |

| Chromosome | Position | TSACP Detection | TSTP Detection |
|---|---|---|---|
| 2 | 212652764 | Detected | Not Covered |
| 2 | 212652791 | Detected | Not Covered |
| 3 | 10183797 | Detected | Not Covered |
| 3 | 10183808 | Detected | Not Covered |
| 3 | 10183817 | Detected | Not Covered |
| 3 | 10183824 | Detected | Not Covered |

TABLE 9-continued

| | | | |
|---|---|---|---|
| 3 | 10188200 | Not Covered | Not Covered |
| 3 | 10188210 | Not Covered | Not Covered |
| 3 | 10188245 | Detected | Not Covered |
| 3 | 10188286 | Detected | Not Covered |
| 3 | 10191479 | Not Detected | Not Covered |
| 3 | 10191488 | Detected | Not Covered |
| 3 | 10191506 | Detected | Not Covered |
| 3 | 10191513 | Not Detected | Not Covered |
| 3 | 37067240 | Detected | Not Covered |
| 3 | 41266101 | Detected | Detected |
| 3 | 41266113 | Detected | Detected |
| 3 | 41266124 | Detected | Detected |
| 3 | 41266137 | Detected | Detected |
| 3 | 138665163 | Not Covered | Detected |
| 3 | 178916648 | Not Covered | Detected |
| 3 | 178916706 | Not Covered | Detected |
| 3 | 178916793 | Not Covered | Detected |
| 3 | 178916823 | Not Covered | Detected |
| 3 | 178916936 | Detected | Detected |
| 3 | 178916944 | Detected | Detected |
| 3 | 178916957 | Detected | Detected |
| 3 | 178917661 | Not Covered | Detected |
| 3 | 178921489 | Not Covered | Not Covered |
| 3 | 178921520 | Not Covered | Not Covered |
| 3 | 178921553 | Detected | Not Covered |
| 3 | 178927450 | Not Covered | Not Covered |
| 3 | 178927980 | Detected | Detected |

| Chromosome | Position | Reference |
|---|---|---|
| 3 | 178928092 | A |
| 3 | 178936074 | C |
| 3 | 178936082 | G |
| 3 | 178936091 | G |
| 3 | 178936098 | A |
| 3 | 178938860 | A |
| 3 | 178947827 | G |
| 3 | 178947850 | T |
| 3 | 178952055 | A |
| 3 | 178952085 | A |
| 3 | 178952149 | C |
| 4 | 1803568 | C |

TABLE 9-continued

| | | |
|---|---|---|
| 4 | 1803575 | C |
| 4 | 1803668 | GC |
| 4 | 1806089 | G |
| 4 | 1806119 | G |
| 4 | 1806131 | T |
| 4 | 1806153 | C |
| 4 | 1807869 | A |
| 4 | 1807889 | A |
| 4 | 1807894 | G |
| 4 | 1808331 | G |
| 4 | 1808962 | A |
| 4 | 55141051 | GCCCAGATGGACATGA (SEQ ID NO: 19) |
| 4 | 55141055 | A |
| 4 | 55141097 | T |
| 4 | 55144148 | C |
| 4 | 55144172 | A |
| 4 | 55144547 | C |
| 4 | 55151958 | T |
| 4 | 55152085 | G |
| 4 | 55152093 | A |
| 4 | 55152112 | C |

| Chromosome | Position | Alternate |
|---|---|---|
| 3 | 178928092 | G |
| 3 | 178936074 | G |
| 3 | 178936082 | A |
| 3 | 178936091 | A |
| 3 | 178936098 | G |
| 3 | 178938860 | C |
| 3 | 178947827 | T |
| 3 | 178947850 | C |
| 3 | 178952055 | G |
| 3 | 178952085 | G |
| 3 | 178952149 | CA |
| 4 | 1803568 | G |
| 4 | 1803575 | T |
| 4 | 1803668 | G |
| 4 | 1806089 | T |
| 4 | 1806119 | A |
| 4 | 1806131 | C |
| 4 | 1806153 | A |

TABLE 9-continued

| | | | | |
|---|---|---|---|---|
| | 4 | 1807869 | | G |
| | 4 | 1807889 | | G |
| | 4 | 1807894 | | A |
| | 4 | 1808331 | | T |
| | 4 | 1808962 | | C |
| | 4 | 55141051 | | G |
| | 4 | 55141055 | | G |
| | 4 | 55141097 | | C |
| | 4 | 55144148 | | A |
| | 4 | 55144172 | | G |
| | 4 | 55144547 | | T |
| | 4 | 55151958 | | TA |
| | 4 | 55152085 | | T |
| | 4 | 55152093 | | T |
| | 4 | 55152112 | | A |

| Chromosome | Position | Length | Mutation ID | Gene |
|---|---|---|---|---|
| 3 | 178928092 | 1 | COSM1420828 | PIK3CA |
| 3 | 178936074 | 1 | COSM759 | PIK3CA |
| 3 | 178936082 | 1 | COSM760 | PIK3CA |
| 3 | 178936091 | 1 | COSM763 | PIK3CA |
| 3 | 178936098 | 1 | COSM1420865 | PIK3CA |
| 3 | 178938860 | 1 | COSM778 | PIK3CA |
| 3 | 178947827 | 1 | COSM769 | PIK3CA |
| 3 | 178947850 | 1 | COSM770 | PIK3CA |
| 3 | 178952055 | 1 | COSM328026 | PIK3CA |
| 3 | 178952085 | 1 | COSM775 | PIK3CA |
| 3 | 178952149 | 1 | COSM12464 | PIK3CA |
| 4 | 1803568 | 1 | COSM715 | FGFR3 |
| 4 | 1803575 | 1 | COSM29446 | FGFR3 |
| 4 | 1803668 | 1 | COSM723 | FGFR3 |
| 4 | 1806089 | 1 | COSM716 | FGFR3 |
| 4 | 1806119 | 1 | COSM24842 | FGFR3 |
| 4 | 1806131 | 1 | COSM724 | FGFR3 |
| 4 | 1806153 | 1 | COSM721 | FGFR3 |
| 4 | 1807869 | 1 | COSM1428724 | FGFR3 |
| 4 | 1807889 | 1 | COSM719 | FGFR3 |
| 4 | 1807894 | 1 | gDNA1 | FGFR3 |
| 4 | 1808331 | 1 | COSM24802 | FGFR3 |
| 4 | 1808962 | 1 | AMXsynt1 | FGFR3 |
| 4 | 55141051 | 15 | COSM12418 | PDGFRA |

TABLE 9-continued

| | | | | |
|---|---|---|---|---|
| 4 | 55141055 | 1 | gDNA2, COSM1430082 | PDGFRA |
| 4 | 55141097 | 1 | COSM1430085 | PDGFRA |
| 4 | 55144148 | 1 | COSM22415 | PDGFRA |
| 4 | 55144172 | 1 | COSM1430086 | PDGFRA |
| 4 | 55144547 | 1 | COSM743 | PDGFRA |
| 4 | 55151958 | 1 | gDNA33 | PDGFRA |
| 4 | 55152085 | 1 | COSM587613 | PDGFRA |
| 4 | 55152093 | 1 | COSM736 | PDGFRA |
| 4 | 55152112 | 1 | COSM28052 | PDGFRA |

| Chromosome | Position | Mutation CDS |
|---|---|---|
| 3 | 178928092 | c.1370A > G |
| 3 | 178936074 | c.1616C > G |
| 3 | 178936082 | c.1624G > A |
| 3 | 178936091 | c.1633G > A |
| 3 | 178936098 | c.1640A > G |
| 3 | 178938860 | c.2102A > C |
| 3 | 178947827 | c.2702G > T |
| 3 | 178947850 | c.2725T > C |
| 3 | 178952055 | c.3110A > G |
| 3 | 178952085 | c.3140A > G |
| 3 | 178952149 | c.3204_3205insA |
| 4 | 1803568 | c.746C > G |
| 4 | 1803575 | c.753C > T |
| 4 | 1803668 | c.850delC |
| 4 | 1806089 | c.1108G > T |
| 4 | 1806119 | c.1138G > A |
| 4 | 1806131 | c.1150T > C |
| 4 | 1806153 | c.1172C > A |
| 4 | 1807869 | c.1928A > G |
| 4 | 1807889 | c.1948A > G |
| 4 | 1807894 | c.1959A > G |
| 4 | 1808331 | c.2089G > T |
| 4 | 1808962 | c.2401A > C |
| 4 | 55141051 | c.1698_1712del15 |
| 4 | 55141055 | c.1701A > G |
| 4 | 55141097 | c.1743T > C |
| 4 | 55144148 | c.1977C > A |
| 4 | 55144172 | c.2001A > G |
| 4 | 55144547 | c.2021C > T |
| 4 | 55151958 | c.2440 − 50 c.2440 − 49insA |

TABLE 9-continued

| | | | | | |
|---|---|---|---|---|---|
| 4 | 55152085 | c.2517G > T | | | |
| 4 | 55152093 | c.2525A > T | | | |
| 4 | 55152112 | c.2544C > A | | | |

| Chromosome | Position Mutation AA | Mutation Type | Strand | Target Frequency | Sanger Detection* |
|---|---|---|---|---|---|
| 3 | 178928092 p.N457S | SNV | + | 5-15% | Detected |
| 3 | 178936074 p.P539R | SNV | + | 5-15% | Detected |
| 3 | 178936082 p.E542K | SNV | + | 5-15% | Detected |
| 3 | 178936091 p.E545K | SNV | + | 5-15% | Detected |
| 3 | 178936098 p.E547G | SNV | + | 5-15% | Detected |
| 3 | 178938860 p.H701P | SNV | + | 5-15% | Detected |
| 3 | 178947827 p.C901F | SNV | + | 5-15% | Detected |
| 3 | 178947850 p.F909L | SNV | + | 5-15% | Detected |
| 3 | 178952055 p.E1037G | SNV | + | 5-15% | Detected |
| 3 | 178952085 p.H1047R | SNV | + | 5-15% | Detected |
| 3 | 178952149 p.N1068fs*4 | INS | + | 5-15% | Detected |
| 4 | 1803568 p.S249C | SNV | + | 5-15% | Detected |
| 4 | 1803575 p.H251H | SNV | + | 5-15% | Detected |
| 4 | 1803668 p.H284fs*10 | DEL | + | 5-15% | Detected |
| 4 | 1806089 p.G370C | SNV | + | 5-15% | Detected |
| 4 | 1806119 p.G380R | SNV | + | 5-15% | Detected |
| 4 | 1806131 p.F384L | SNV | + | 5-15% | Detected |
| 4 | 1806153 p.A391E | SNV | + | 5-15% | Detected |
| 4 | 1807869 p.H643R | SNV | + | 5-15% | Detected |
| 4 | 1807889 p.K650E | SNV | + | 5-15% | Detected |
| 4 | 1807894 p.T651T | SNV | + | genomic | Not Covered |
| 4 | 1808331 p.G697C | SNV | + | 5-15% | Detected |
| 4 | 1808962 p.P800P | SNV | + | 5-15% | Detected |
| 4 | 55141051 p.S566_E571 > R | DEL | + | 5-15% | Detected |
| 4 | 55141055 p.P567P | SNV | + | genomic | Not Covered |
| 4 | 55141097 p.P581P | SNV | + | 5-15% | Detected |
| 4 | 55144148 p.N659K | SNV | + | 5-15% | Detected |
| 4 | 55144172 p.S667S | SNV | + | 5-15% | Detected |
| 4 | 55144547 p.T674I | SNV | + | 5-15% | Detected |
| 4 | 55151958 p.(=) | INS | + | genomic | Not Covered |
| 4 | 55152085 p.L839L | SNV | + | 5-15% | Detected |
| 4 | 55152093 p.D842V | SNV | + | 5-15% | Detected |
| 4 | 55152112 p.N848K | SNV | + | 5-15% | Detected |

TABLE 9-continued

| Chromosome | Position | CHPv2 Detection | TSACP Detection | TSTP Detection |
|---|---|---|---|---|
| 3 | 178928092 | Detected | Not Covered | Detected |
| 3 | 178936074 | Detected | Detected | Detected |
| 3 | 178936082 | Detected | Detected | Detected |
| 3 | 178936091 | Detected | Detected | Detected |
| 3 | 178936098 | Detected | Detected | Detected |
| 3 | 178938860 | Detected | Detected | Not Covered |
| 3 | 178947827 | Detected | Not Covered | Not Covered |
| 3 | 178947850 | Detected | Not Covered | Not Covered |
| 3 | 178952055 | Detected | Not Detected | Detected |
| 3 | 178952085 | Detected | Not Detected | Detected |
| 3 | 178952149 | Detected | Detected | Not Detected |
| 4 | 1803568 | Detected | Detected | Not Covered |
| 4 | 1803575 | Detected | Detected | Not Covered |
| 4 | 1803668 | Not Covered | Detected | Not Covered |
| 4 | 1806089 | Detected | Not Covered | Not Covered |
| 4 | 1806119 | Detected | Detected | Not Covered |
| 4 | 1806131 | Detected | Detected | Not Covered |
| 4 | 1806153 | Detected | Detected | Not Covered |
| 4 | 1807869 | Detected | Detected | Not Covered |
| 4 | 1807889 | Detected | Detected | Not Covered |
| 4 | 1807894 | Detected | Detected | Not Covered |
| 4 | 1808331 | Detected | Not Detected | Not Covered |
| 4 | 1808962 | Detected | Detected | Not Covered |
| 4 | 55141051 | Detected | Detected | Detected |
| 4 | 55141055 | Detected | Detected | Detected |
| 4 | 55141097 | Detected | Detected | Detected |
| 4 | 55144148 | Detected | Detected | Detected |
| 4 | 55144172 | Detected | Detected | Detected |
| 4 | 55144547 | Detected | Detected | Not Covered |
| 4 | 55151958 | Not Covered | Not Covered | Detected |
| 4 | 55152085 | Detected | Detected | Detected |
| 4 | 55152093 | Detected | Detected | Detected |
| 4 | 55152112 | Detected | Detected | Detected |

| Chromosome | Position | Reference |
|---|---|---|
| 4 | 55561702 | C |
| 4 | 55561764 | G |
| 4 | 55561828 | A |
| 4 | 55592081 | T |
| 4 | 55592092 | A |

TABLE 9-continued

| | | |
|---|---|---|
| 4 | 55592178 | C |
| 4 | 55592192 | T |
| 4 | 55592202 | A |
| 4 | 55592211 | A |
| 4 | 55593431 | G |
| 4 | 55593464 | A |
| 4 | 55593632 | C |
| 4 | 55593661 | T |
| 4 | 55593689 | C |
| 4 | 55594221 | A |
| 4 | 55594258 | T |
| 4 | 55595599 | C |
| 4 | 55597500 | T |
| 4 | 55597561 | G |
| 4 | 55599284 | C |
| 4 | 55599401 | T |
| 4 | 55599436 | T |
| 4 | 55602737 | G |
| 4 | 55602765 | G |
| 4 | 55946081 | A |
| 4 | 55946171 | G |
| 4 | 55953816 | ACTTCCTCCTCCTCCATACAGGAAAC (SEQ ID NO: 20) |
| 4 | 55955112 | C |
| 4 | 55961023 | C |
| 4 | 55962505 | T |
| 4 | 55962545 | T |
| 4 | 55972974 | T |
| 4 | 55972978 | CTATAAGAAAGAGATAACAGCGCATATTATGATTTAATTTTT (SEQ ID NO: 21) |

| Chromosome | Position | Alternate |
|---|---|---|
| 4 | 55561702 | T |
| 4 | 55561764 | A |
| 4 | 55561828 | G |
| 4 | 55592081 | C |
| 4 | 55592092 | G |
| 4 | 55592178 | CTGCCTA |
| 4 | 55592192 | C |
| 4 | 55592202 | T |
| 4 | 55592211 | G |
| 4 | 55593431 | A |

TABLE 9-continued

| | | | | |
|---|---|---|---|---|
| 4 | 55593464 | | C | |
| 4 | 55593632 | | T | |
| 4 | 55593661 | | C | |
| 4 | 55593689 | | T | |
| 4 | 55594221 | | G | |
| 4 | 55594258 | | C | |
| 4 | 55595599 | | T | |
| 4 | 55597500 | | C | |
| 4 | 55597561 | | A | |
| 4 | 55599284 | | T | |
| 4 | 55599401 | | A | |
| 4 | 55599436 | | C | |
| 4 | 55602737 | | A | |
| 4 | 55602765 | | C | |
| 4 | 55946081 | | G | |
| 4 | 55946171 | | A | |
| 4 | 55953816 | | A | |
| 4 | 55955112 | | T | |
| 4 | 55961023 | | A | |
| 4 | 55962505 | | C | |
| 4 | 55962545 | | TG | |
| 4 | 55972974 | | A | |
| 4 | 55972978 | | C | |

| Chromosome | Position | Length | Mutation ID | Gene |
|---|---|---|---|---|
| 4 | 55561702 | 1 | COSM77973 | KIT |
| 4 | 55561764 | 1 | COSM1146 | KIT |
| 4 | 55561828 | 1 | COSM1430106 | KIT |
| 4 | 55592081 | 1 | COSM24637 | KIT |
| 4 | 55592092 | 1 | COSM41602 | KIT |
| 4 | 55592178 | 6 | COSM1326 | KIT |
| 4 | 55592192 | 1 | COSM96867 | KIT |
| 4 | 55592202 | 1 | COSM96885 | KIT |
| 4 | 55592211 | 1 | COSM1430136 | KIT |
| 4 | 55593431 | 1 | COSM1155 | KIT |
| 4 | 55593464 | 1 | gDNA3, COSM28026 | KIT |
| 4 | 55593632 | 1 | COSM1275 | KIT |
| 4 | 55593661 | 1 | COSM1290 | KIT |
| 4 | 55593689 | 1 | COSM1299 | KIT |
| 4 | 55594221 | 1 | COSM1304 | KIT |
| 4 | 55594258 | 1 | COSM12706 | KIT |

TABLE 9-continued

| | | | | |
|---|---|---|---|---|
| 4 | 55595599 | 1 | COSM36053 | KIT |
| 4 | 55597500 | 1 | COSM1430171 | KIT |
| 4 | 55597561 | 1 | COSM21303 | KIT |
| 4 | 55599284 | 1 | COSM20402 | KIT |
| 4 | 55599401 | 1 | COSM19194 | KIT |
| 4 | 55599436 | 1 | gDNA4 | KIT |
| 4 | 55602737 | 1 | COSM133767 | KIT |
| 4 | 55602765 | 1 | gDNA5, COSM1325 | KIT |
| 4 | 55946081 | 1 | gDNA6 | KDR |
| 4 | 55946171 | 1 | COSM35855 | KDR |
| 4 | 55953816 | 25 | AMXsynt2 | KDR |
| 4 | 55955112 | 1 | COSM1430203 | KDR |
| 4 | 55961023 | 1 | COSM48464 | KDR |
| 4 | 55962505 | 1 | COSM1430212 | KDR |
| 4 | 55962545 | 1 | gDNA7 | KDR |
| 4 | 55972974 | 1 | gDNA8, COSM149673 | KDR |
| 4 | 55972978 | 41 | AMXsynt3 | KDR |

| Chromosome | Position | Mutation CDS |
|---|---|---|
| 4 | 55561702 | c.92C > T |
| 4 | 55561764 | c.154G > A |
| 4 | 55561828 | c.218A > G |
| 4 | 55592081 | c.1405T > C |
| 4 | 55592092 | c.1416A > G |
| 4 | 55592178 | c.1509_1510insGCCTAT |
| 4 | 55592192 | c.1516T > C |
| 4 | 55592202 | c.1526A > T |
| 4 | 55592211 | c.1535A > G |
| 4 | 55593431 | c.1588G > A |
| 4 | 55593464 | c.1621A > C |
| 4 | 55593632 | c.1698C > T |
| 4 | 55593661 | c.1727T > C |
| 4 | 55593689 | c.1755C > T |
| 4 | 55594221 | c.1924A > G |
| 4 | 55594258 | c.1961T > C |
| 4 | 55595599 | c.2089C > T |
| 4 | 55597500 | c.2148T > C |
| 4 | 55597561 | c.2209G > A |
| 4 | 55599284 | c.2410C > T |
| 4 | 55599401 | c.2484 + 43T > A |
| 4 | 55599436 | c.2484 + 78T > C |

TABLE 9-continued

| | | | |
|---|---|---|---|
| 4 | 55602737 | c.2558G > A | |
| 4 | 55602765 | c.2586G > C | |
| 4 | 55946081 | c.*27T > C | |
| 4 | 55946171 | c.4008C > T | |
| 4 | 55953816 | c.3594del25 | |
| 4 | 55955112 | c.3433G > A | |
| 4 | 55961023 | c.2917G > T | |
| 4 | 55962505 | c.2619A > G | |
| 4 | 55962545 | c.2615 − 37_2615 − 36insC | |
| 4 | 55972974 | c.1416A > T | |
| 4 | 55972978 | c.1413 − 42del41 | |

| Chromosome | Position | Mutation AA | Mutation Type | Strand | Target Frequency | Sanger Detection* |
|---|---|---|---|---|---|---|
| 4 | 55561702 | p.P31L | SNV | + | 5-15% | Detected |
| 4 | 55561764 | p.D52N | SNV | + | 5-15% | Detected |
| 4 | 55561828 | p.E73G | SNV | + | 5-15% | Detected |
| 4 | 55592081 | p.F469L | SNV | + | 5-15% | Detected |
| 4 | 55592092 | p.L472L | SNV | + | 5-15% | Detected |
| 4 | 55592178 | p.Y503_F504insAY | INS | + | 5-15% | Detected |
| 4 | 55592192 | p.F506L | SNV | + | 5-15% | Detected |
| 4 | 55592202 | p.K509I | SNV | + | 5-15% | Detected |
| 4 | 55592211 | p.N512S | SNV | + | 5-15% | Detected |
| 4 | 55593431 | p.V530I | SNV | + | 5-15% | Detected |
| 4 | 55593464 | p.M541L | SNV | + | genomic | Not Covered |
| 4 | 55593632 | p.N566N | SNV | + | 5-15% | Detected |
| 4 | 55593661 | p.L576P | SNV | + | 5-15% | Detected |
| 4 | 55593689 | p.P585P | SNV | + | 5-15% | Detected |
| 4 | 55594221 | p.K642E | SNV | + | 5-15% | Detected |
| 4 | 55594258 | p.V654A | SNV | + | 5-15% | Detected |
| 4 | 55595599 | p.H697Y | SNV | + | 5-15% | Detected |
| 4 | 55597500 | p.D716D | SNV | + | 5-15% | Detected |
| 4 | 55597561 | p.D737N | SNV | + | 5-15% | Detected |
| 4 | 55599284 | p.R804W | SNV | + | 5-15% | Detected |
| 4 | 55599401 | p.? | SNV | + | 5-15% | Detected |
| 4 | 55599436 | p.(=) | SNV | + | genomic | Not Covered |
| 4 | 55602737 | p.W853* | SNV | + | 5-15% | Detected |
| 4 | 55602765 | p.L862L | SNV | + | genomic | Not Covered |
| 4 | 55946081 | p.(=) | SNV | − | genomic | Not Covered |
| 4 | 55946171 | p.T1336T | SNV | − | 5-15% | Detected |
| 4 | 55953816 | p.V1199fs*27 | DEL | − | 5-15% | Detected |
| 4 | 55955112 | p.G1145R | SNV | − | 5-15% | Detected |

TABLE 9-continued

| | | | | | |
|---|---|---|---|---|---|
| 4 | 55961023 | p.A973S | SNV | – | 5-15% | Detected |
| 4 | 55962505 | p.G873G | SNV | – | 5-15% | Detected |
| 4 | 55962545 | p.(=) | INS | – | genomic | Not Covered |
| 4 | 55972974 | p.Q472H | SNV | – | genomic | Not Covered |
| 4 | 55972978 | p.? | DEL | – | 5-15% | Detected |

| Chromosome | Position | CHPv2 Detection | TSACP Detection | TSTP Detection |
|---|---|---|---|---|
| 4 | 55561702 | Detected | Not Covered | Not Covered |
| 4 | 55561764 | Detected | Detected | Not Covered |
| 4 | 55561828 | Not Covered | Detected | Not Covered |
| 4 | 55592081 | Not Covered | Not Covered | Detected |
| 4 | 55592092 | Not Covered | Not Covered | Detected |
| 4 | 55592178 | Detected | Not Covered | Detected |
| 4 | 55592192 | Detected | Detected | Detected |
| 4 | 55592202 | Detected | Detected | Detected |
| 4 | 55592211 | Detected | Detected | Detected |
| 4 | 55593431 | Detected | Detected | Not Covered |
| 4 | 55593464 | Detected | Detected | Not Covered |
| 4 | 55593632 | Detected | Detected | Detected |
| 4 | 55593661 | Detected | Detected | Detected |
| 4 | 55593689 | Detected | Detected | Detected |
| 4 | 55594221 | Detected | Detected | Detected |
| 4 | 55594258 | Detected | Detected | Detected |
| 4 | 55595599 | Not Covered | Detected | Not Covered |
| 4 | 55597500 | Detected | Detected | Not Covered |
| 4 | 55597561 | Not Covered | Detected | Not Covered |
| 4 | 55599284 | Detected | Not Covered | Detected |
| 4 | 55599401 | Not Covered | Detected | Detected |
| 4 | 55599436 | Not Covered | Detected | Not Detected |
| 4 | 55602737 | Detected | Detected | Detected |
| 4 | 55602765 | Not Covered | Detected | Detected |
| 4 | 55946081 | Not Covered | Detected | Not Covered |
| 4 | 55946171 | Detected | Detected | Not Covered |
| 4 | 55953816 | Detected | Detected | Not Covered |
| 4 | 55955112 | Detected | Detected | Not Covered |
| 4 | 55961023 | Detected | Detected | Not Covered |
| 4 | 55962505 | Detected | Detected | Not Covered |
| 4 | 55962545 | Detected | Detected | Not Covered |
| 4 | 55972974 | Detected | Detected | Not Covered |
| 4 | 55972978 | Detected | Not Detected | Not Covered |

TABLE 9-continued

| Chromosome | Position | Reference |
|---|---|---|
| 4 | 55979623 | C |
| 4 | 55980239 | C |
| 4 | 153244078 | T |
| 4 | 153244092 | G |
| 4 | 153244124 | G |
| 4 | 153244155 | TC |
| 4 | 153245477 | T |
| 4 | 153247222 | T |
| 4 | 153247226 | A |
| 4 | 153247244 | C |
| 4 | 153247351 | C |
| 4 | 153247366 | C |
| 4 | 153249384 | C |
| 4 | 153249440 | C |
| 4 | 153249456 | C |
| 4 | 153250883 | G |
| 4 | 153258983 | G |
| 4 | 153259071 | C |
| 5 | 112173830 | G |
| 5 | 112173917 | C |
| 5 | 112173930 | T |
| 5 | 112173947 | C |
| 5 | 112174043 | G |
| 5 | 112174577 | C |
| 5 | 112174596 | A |
| 5 | 112174726 | A |
| 5 | 112174989 | CA |
| 5 | 112175086 | A |
| 5 | 112175162 | C |
| 5 | 112175171 | C |
| 5 | 112175211 | T |
| 5 | 112175255 | G |
| 5 | 112175348 | G |

| Chromosome | Position | Alternate |
|---|---|---|
| 4 | 55979623 | A |
| 4 | 55980239 | T |
| 4 | 153244078 | C |
| 4 | 153244092 | A |
| 4 | 153244124 | C |

TABLE 9-continued

| | | |
|---|---|---|
| 4 | 153244155 | T |
| 4 | 153245477 | TGATCATATTCATATTCTCTGAAATCAACGAG (SEQ ID NO: 22) |
| 4 | 153247222 | C |
| 4 | 153247226 | G |
| 4 | 153247244 | T |
| 4 | 153247351 | A |
| 4 | 153247366 | T |
| 4 | 153249384 | T |
| 4 | 153249440 | T |
| 4 | 153249456 | A |
| 4 | 153250883 | A |
| 4 | 153258983 | A |
| 4 | 153259071 | A |
| 5 | 112173830 | GA |
| 5 | 112173917 | T |
| 5 | 112173930 | C |
| 5 | 112173947 | T |
| 5 | 112174043 | T |
| 5 | 112174577 | T |
| 5 | 112174596 | G |
| 5 | 112174726 | G |
| 5 | 112174989 | C |
| 5 | 112175086 | G |
| 5 | 112175162 | T |
| 5 | 112175171 | T |
| 5 | 112175211 | TA |
| 5 | 112175255 | T |
| 5 | 112175348 | T |

| Chromosome | Position | Length | Mutation ID | Gene |
|---|---|---|---|---|
| 4 | 55979623 | 1 | COSM32339 | KDR |
| 4 | 55980239 | 1 | gDNA9 | KDR |
| 4 | 153244078 | 1 | COSM1427592 | FBXW7 |
| 4 | 153244092 | 1 | COSM27083 | FBXW7 |
| 4 | 153244124 | 1 | COSM732399 | FBXW7 |
| 4 | 153244155 | 1 | COSM34018 | FBXW7 |
| 4 | 153245477 | 31 | AMXsynt4 | FBXW7 |
| 4 | 153247222 | 1 | COSM27913 | FBXW7 |
| 4 | 153247226 | 1 | COSM30599 | FBXW7 |
| 4 | 153247244 | 1 | COSM30598 | FBXW7 |
| 4 | 153247351 | 1 | COSM34016 | FBXW7 |

TABLE 9-continued

| Chromosome | Position | | | |
|---|---|---|---|---|
| 4 | 153247366 | 1 | COSM22974 | FBXW7 |
| 4 | 153249384 | 1 | COSM22965 | FBXW7 |
| 4 | 153249440 | 1 | COSM22986 | FBXW7 |
| 4 | 153249456 | 1 | COSM161024 | FBXW7 |
| 4 | 153250883 | 1 | COSM22973 | FBXW7 |
| 4 | 153258983 | 1 | COSM22971 | FBXW7 |
| 4 | 153259071 | 1 | COSM1052125 | FBXW7 |
| 5 | 112173830 | 1 | COSM18979 | APC |
| 5 | 112173917 | 1 | COSM18852 | APC |
| 5 | 112173930 | 1 | COSM19230 | APC |
| 5 | 112173947 | 1 | COSM19330 | APC |
| 5 | 112174043 | 1 | COSM19065 | APC |
| 5 | 112174577 | 1 | COSM13872 | APC |
| 5 | 112174596 | 1 | COSM1432250 | APC |
| 5 | 112174726 | 1 | COSM1432260 | APC |
| 5 | 112174989 | 1 | COSM41617 | APC |
| 5 | 112175086 | 1 | COSM1432280 | APC |
| 5 | 112175162 | 1 | COSM19072 | APC |
| 5 | 112175171 | 1 | COSM18960 | APC |
| 5 | 112175211 | 1 | COSM18719 | APC |
| 5 | 112175255 | 1 | COSM18702 | APC |
| 5 | 112175348 | 1 | COSM19048 | APC |

| Chromosome | Position | Mutation CDS |
|---|---|---|
| 4 | 55979623 | c.824G > T |
| 4 | 55980239 | c.798 + 54G > A |
| 4 | 153244078 | c.2079A > G |
| 4 | 153244092 | c.2065C > T |
| 4 | 153244124 | c.2033C > G |
| 4 | 153244155 | c.2001delG |
| 4 | 153245477 | c.1473_1474insCTCGTTGATTTCAGAGAATATGAATATGATC (SEQ ID NO: 23) |
| 4 | 153247222 | c.1580A > G |
| 4 | 153247226 | c.1576T > C |
| 4 | 153247244 | c.1558G > A |
| 4 | 153247351 | c.1451G > T |
| 4 | 153247366 | c.1436G > A |
| 4 | 153249384 | c.1394G > A |
| 4 | 153249440 | c.1338G > A |
| 4 | 153249456 | c.1322G > T |
| 4 | 153250883 | c.1177C > T |

TABLE 9-continued

| | | |
|---|---|---|
| 4 | 153258983 | c.832C > T |
| 4 | 153259071 | c.744G > T |
| 5 | 112173830 | c.2543_2544insA |
| 5 | 112173917 | c.2626C > T |
| 5 | 112173930 | c.2639T > C |
| 5 | 112173947 | c.2656C > T |
| 5 | 112174043 | c.2752G > T |
| 5 | 112174577 | c.3286C > T |
| 5 | 112174596 | c.3305A > G |
| 5 | 112174726 | c.3435A > G |
| 5 | 112174989 | c.3700delA |
| 5 | 112175086 | c.3795A > G |
| 5 | 112175162 | c.3871C > T |
| 5 | 112175171 | c.3880C > T |
| 5 | 112175211 | c.3923_3924insA |
| 5 | 112175255 | c.3964G > T |
| 5 | 112175348 | c.4057G > T |

| Chromosome | Position | Mutation AA | Mutation Type | Strand | Target Frequency | Sanger Detection* |
|---|---|---|---|---|---|---|
| 4 | 55979623 | p.R275L | SNV | − | 5-15% | Detected |
| 4 | 55980239 | p.(=) | SNV | − | genomic | Not Covered |
| 4 | 153244078 | p.E693E | SNV | − | 5-15% | Detected |
| 4 | 153244092 | p.R689W | SNV | − | 5-15% | Detected |
| 4 | 153244124 | p.S678* | SNV | − | 5-15% | Detected |
| 4 | 153244155 | p.S668fs*39 | DEL | − | 5-15% | Detected |
| 4 | 153245477 | p.N492fs*42 | INS | − | 5-15% | Detected |
| 4 | 153247222 | p.D527G | SNV | − | 5-15% | Detected |
| 4 | 153247226 | p.W526R | SNV | − | 5-15% | Detected |
| 4 | 153247244 | p.D520N | SNV | − | 5-15% | Detected |
| 4 | 153247351 | p.R484M | SNV | − | 5-15% | Detected |
| 4 | 153247366 | p.R479Q | SNV | − | 5-15% | Detected |
| 4 | 153249384 | p.R465H | SNV | − | 5-15% | Detected |
| 4 | 153249440 | p.W446* | SNV | − | 5-15% | Detected |
| 4 | 153249456 | p.R441L | SNV | − | 5-15% | Detected |
| 4 | 153250883 | p.R393* | SNV | − | 5-15% | Detected |
| 4 | 153258983 | p.R278* | SNV | − | 5-15% | Detected |
| 4 | 153259071 | p.E248D | SNV | − | 5-15% | Detected |
| 5 | 112173830 | p.D849fs*2 | INS | + | 15-35% | Detected |
| 5 | 112173917 | p.R876* | SNV | + | 15-35% | Detected |
| 5 | 112173930 | p.I880T | SNV | + | 15-35% | Detected |
| 5 | 112173947 | p.Q886* | SNV | + | 15-35% | Detected |

TABLE 9-continued

| 5 | 112174043 | p.E918* | SNV | + | 15-35% | Detected |
| 5 | 112174577 | p.Q1096* | SNV | + | 15-35% | Detected |
| 5 | 112174596 | p.Y1102C | SNV | + | 15-35% | Detected |
| 5 | 112174726 | p.E1145E | SNV | + | 15-35% | Detected |
| 5 | 112174989 | p.S1234fs*31 | DEL | + | 15-35% | Detected |
| 5 | 112175086 | p.E1265E | SNV | + | 15-35% | Detected |
| 5 | 112175162 | p.Q1291* | SNV | + | 15-35% | Detected |
| 5 | 112175171 | p.Q1294* | SNV | + | 15-35% | Detected |
| 5 | 112175211 | p.E1309fs*6 | INS | + | 15-35% | Detected |
| 5 | 112175255 | p.E1322* | SNV | + | 15-35% | Detected |
| 5 | 112175348 | p.E1353* | SNV | + | 15-35% | Detected |

| Chromosome | Position | CHPv2 Detection | TSACP Detection | TSTP Detection |
|---|---|---|---|---|
| 4 | 55979623 | Detected | Detected | Not Covered |
| 4 | 55980239 | Detected | Not Covered | Not Covered |
| 4 | 153244078 | Not Covered | Not Covered | Detected |
| 4 | 153244092 | Not Covered | Not Covered | Detected |
| 4 | 153244124 | Not Covered | Not Covered | Detected |
| 4 | 153244155 | Not Covered | Not Covered | Detected |
| 4 | 153245477 | Not Detected | Detected | Detected |
| 4 | 153247222 | Not Covered | Not Covered | Detected |
| 4 | 153247226 | Not Covered | Not Covered | Detected |
| 4 | 153247244 | Not Covered | Not Covered | Detected |
| 4 | 153247351 | Detected | Detected | Detected |
| 4 | 153247366 | Detected | Detected | Detected |
| 4 | 153249384 | Detected | Detected | Detected |
| 4 | 153249440 | Detected | Detected | Detected |
| 4 | 153249456 | Detected | Detected | Detected |
| 4 | 153250883 | Detected | Detected | Detected |
| 4 | 153258983 | Detected | Detected | Not Covered |
| 4 | 153259071 | Not Covered | Detected | Not Covered |
| 5 | 112173830 | Not Covered | Not Covered | Detected |
| 5 | 112173917 | Detected | Detected | Detected |
| 5 | 112173930 | Detected | Detected | Detected |
| 5 | 112173947 | Detected | Detected | Detected |
| 5 | 112174043 | Not Covered | Detected | Not Covered |
| 5 | 112174577 | Detected | Not Covered | Detected |
| 5 | 112174596 | Detected | Not Covered | Detected |
| 5 | 112174726 | Not Covered | Detected | Detected |
| 5 | 112174989 | Not Covered | Not Covered | Detected |

TABLE 9-continued

| | | | | |
|---|---|---|---|---|
| 5 | 112175086 | Not Covered | Detected | Detected |
| 5 | 112175162 | Detected | Detected | Detected |
| 5 | 112175171 | Detected | Detected | Detected |
| 5 | 112175211 | Detected | Detected | Detected |
| 5 | 112175255 | Detected | Detected | Detected |
| 5 | 112175348 | Detected | Detected | Detected |

| Chromosome | Position | Reference |
|---|---|---|
| 5 | 112175354 | T |
| 5 | 112175423 | C |
| 5 | 112175432 | C |
| 5 | 112175479 | TGA |
| 5 | 112175507 | C |
| 5 | 112175576 | C |
| 5 | 112175675 | AAG |
| 5 | 112175830 | GC |
| 5 | 112175852 | G |
| 5 | 112175930 | G |
| 5 | 112175945 | G |
| 5 | 112175951 | G |
| 5 | 112176063 | C |
| 5 | 112176117 | C |
| 5 | 149433596 | T |
| 5 | 149433597 | G |
| 5 | 149433645 | T |
| 5 | 149433673 | C |
| 5 | 149453057 | C |
| 5 | 170837543 | C |
| 7 | 55211080 | G |
| 7 | 55211097 | G |
| 7 | 55211165 | C |
| 7 | 55221822 | C |
| 7 | 55221830 | G |
| 7 | 55233043 | G |
| 7 | 55233109 | G |
| 7 | 55241615 | T |
| 7 | 55241644 | G |
| 7 | 55241708 | G |
| 7 | 55241722 | G |
| 7 | 55241755 | G |
| 7 | 55242427 | C |

TABLE 9-continued

| Chromosome | Position | Alternate |
|---|---|---|
| 5 | 112175354 | C |
| 5 | 112175423 | T |
| 5 | 112175432 | T |
| 5 | 112175479 | T |
| 5 | 112175507 | T |
| 5 | 112175576 | T |
| 5 | 112175675 | A |
| 5 | 112175830 | G |
| 5 | 112175852 | T |
| 5 | 112175930 | T |
| 5 | 112175945 | T |
| 5 | 112175951 | GA |
| 5 | 112176063 | CA |
| 5 | 112176117 | T |
| 5 | 149433596 | G |
| 5 | 149433597 | A |
| 5 | 149433645 | C |
| 5 | 149433673 | T |
| 5 | 149453057 | CACTGCTTGA (SEQ ID NO: 24) |
| 5 | 170837543 | CTCTG |
| 7 | 55211080 | A |
| 7 | 55211097 | A |
| 7 | 55211165 | T |
| 7 | 55221822 | T |
| 7 | 55221830 | T |
| 7 | 55233043 | T |
| 7 | 55233109 | A |
| 7 | 55241615 | C |
| 7 | 55241644 | A |
| 7 | 55241708 | C |
| 7 | 55241722 | A |
| 7 | 55241755 | A |
| 7 | 55242427 | T |

| Chromosome | Position | Length | Mutation ID | Gene |
|---|---|---|---|---|
| 5 | 112175354 | 1 | COSM19652 | APC |
| 5 | 112175423 | 1 | COSM18862 | APC |
| 5 | 112175432 | 1 | COSM143913 | APC |
| 5 | 112175479 | 2 | COSM18993 | APC |
| 5 | 112175507 | 1 | COSM19087 | APC |

TABLE 9-continued

| | | | | |
|---|---|---|---|---|
| 5 | 112175576 | 1 | COSM18836 | APC |
| 5 | 112175675 | 2 | COSM13864 | APC |
| 5 | 112175830 | 1 | COSM1173082 | APC |
| 5 | 112175852 | 1 | COSM1183180 | APC |
| 5 | 112175930 | 1 | COSM13879 | APC |
| 5 | 112175945 | 1 | COSM41616 | APC |
| 5 | 112175951 | 1 | COSM18561 | APC |
| 5 | 112176063 | 1 | COSM18875 | APC |
| 5 | 112176117 | 1 | COSM42906 | APC |
| 5 | 149433596 | 1 | gDNA10 | CSF1R |
| 5 | 149433597 | 1 | gDNA11 | CSF1R |
| 5 | 149433645 | 1 | COSM947 | CSF1R |
| 5 | 149433673 | 1 | COSM310349 | CSF1R |
| 5 | 149453057 | 9 | AMXsynt5 | CSF1R |
| 5 | 170837543 | 4 | COSM17559 | NPM1 |
| 7 | 55211080 | 1 | COSM21683 | EGFR |
| 7 | 55211097 | 1 | COSM174732 | EGFR |
| 7 | 55211165 | 1 | COSM1451540 | EGFR |
| 7 | 55221822 | 1 | COSM21687 | EGFR |
| 7 | 55221830 | 1 | COSM43067 | EGFR |
| 7 | 55233043 | 1 | COSM21690 | EGFR |
| 7 | 55233109 | 1 | COSM35825 | EGFR |
| 7 | 55241615 | 1 | COSM13177 | EGFR |
| 7 | 55241644 | 1 | COSM41905 | EGFR |
| 7 | 55241708 | 1 | COSM6239 | EGFR |
| 7 | 55241722 | 1 | COSM13979 | EGFR |
| 7 | 55241755 | 1 | gDNA15 | EGFR |
| 7 | 55242427 | 1 | COSM53194 | EGFR |

| Chromosome | Position | Mutation CDS |
|---|---|---|
| 5 | 112175354 | c.4063T > C |
| 5 | 112175423 | c.4132C > T |
| 5 | 112175432 | c.4141C > T |
| 5 | 112175479 | c.4189_4190delGA |
| 5 | 112175507 | c.4216C > T |
| 5 | 112175576 | c.4285C > T |
| 5 | 112175675 | c.4393_4394delAG |
| 5 | 112175830 | c.4540delC |
| 5 | 112175852 | c.4561G > T |
| 5 | 112175930 | c.4639G > T |
| 5 | 112175945 | c.4654G > T |

TABLE 9-continued

| Chromosome | Position | | | c. notation |
|---|---|---|---|---|
| 5 | 112175951 | | | c.4666_4667insA |
| 5 | 112176063 | | | c.4773_4774insA |
| 5 | 112176117 | | | c.4826C > T |
| 5 | 149433596 | | | c.*36A > C |
| 5 | 149433597 | | | c.*35C > T |
| 5 | 149433645 | | | c.2906A > G |
| 5 | 149433673 | | | c.2878G > A |
| 5 | 149453057 | | | c.890 − 2_c.890 − 1insTCAAGCAGT |
| 5 | 170837543 | | | c.863_864insTCTG |
| 7 | 55211080 | | | c.323G > A |
| 7 | 55211097 | | | c.340G > A |
| 7 | 55211165 | | | c.408C > T |
| 7 | 55221822 | | | c.866C > T |
| 7 | 55221830 | | | c.874G > T |
| 7 | 55233043 | | | c.1793G > T |
| 7 | 55233109 | | | c.1859G > A |
| 7 | 55241615 | | | c.2063T > C |
| 7 | 55241644 | | | c.2092G > A |
| 7 | 55241708 | | | c.2156G > C |
| 7 | 55241722 | | | c.2170G > A |
| 7 | 55241755 | | | c.2184 + 19G > A |
| 7 | 55242427 | | | c.2197C > T |

| Chromosome | Position | Mutation AA | Mutation Type | Strand | Target Frequency | Sanger Detection* |
|---|---|---|---|---|---|---|
| 5 | 112175354 | p.S1355P | SNV | + | 15-35% | Detected |
| 5 | 112175423 | p.Q1378* | SNV | + | 15-35% | Detected |
| 5 | 112175432 | p.P1381S | SNV | + | 15-35% | Detected |
| 5 | 112175479 | p.R1399fs*9 | DEL | + | 15-35% | Detected |
| 5 | 112175507 | p.Q1406* | SNV | + | 15-35% | Detected |
| 5 | 112175576 | p.Q1429* | SNV | + | 15-35% | Detected |
| 5 | 112175675 | p.S1465fs*3 | DEL | + | 15-35% | Detected |
| 5 | 112175830 | p.P1514fs*9 | DEL | + | 15-35% | Detected |
| 5 | 112175852 | p.E1521* | SNV | + | 15-35% | Detected |
| 5 | 112175930 | p.E1547* | SNV | + | 15-35% | Detected |
| 5 | 112175945 | p.E1552* | SNV | + | 15-35% | Detected |
| 5 | 112175951 | p.T1556fs*3 | INS | + | 15-35% | Detected |
| 5 | 112176063 | p.P1594fs*38 | INS | + | 15-35% | Detected |
| 5 | 112176117 | p.P1609L | SNV | + | 15-35% | Detected |
| 5 | 149433596 | p.(=) | SNV | − | genomic | Not Covered |
| 5 | 149433597 | p.(=) | SNV | − | genomic | Not Covered |
| 5 | 149433645 | p.Y969C | SNV | − | 15-35% | Detected |

TABLE 9-continued

| | | | | | | |
|---|---|---|---|---|---|---|
| 5 | 149433673 | p.A960T | SNV | - | 15-35% | Detected |
| 5 | 149453057 | p.? | INS | - | 15-35% | Detected |
| 5 | 170837543 | p.W288fs*12 | INS | + | 15-35% | Detected |
| 7 | 55211080 | p.R108K | SNV | + | 15-35% | Detected |
| 7 | 55211097 | p.E114K | SNV | + | 15-35% | Detected |
| 7 | 55211165 | p.P136P | SNV | + | 15-35% | Detected |
| 7 | 55221822 | p.A289V | SNV | + | 15-35% | Detected |
| 7 | 55221830 | p.V292L | SNV | + | 15-35% | Detected |
| 7 | 55233043 | p.G598V | SNV | + | 15-35% | Detected |
| 7 | 55233109 | p.C620Y | SNV | + | 15-35% | Detected |
| 7 | 55241615 | p.L688P | SNV | + | 15-35% | Detected |
| 7 | 55241644 | p.A698T | SNV | + | 15-35% | Detected |
| 7 | 55241708 | p.G719A | SNV | + | 15-35% | Detected |
| 7 | 55241722 | p.G724S | SNV | + | 15-35% | Detected |
| 7 | 55241755 | p.(=) | SNV | + | genomic | Not Covered |
| 7 | 55242427 | p.P733S | SNV | + | 15-35% | Detected |

| Chromosome | Position | CHPv2 Detection | TSACP Detection | TSTP Detection |
|---|---|---|---|---|
| 5 | 112175354 | Detected | Detected | Detected |
| 5 | 112175423 | Detected | Detected | Detected |
| 5 | 112175432 | Detected | Detected | Detected |
| 5 | 112175479 | Not Covered | Detected | Detected |
| 5 | 112175507 | Not Covered | Detected | Detected |
| 5 | 112175576 | Detected | Detected | Detected |
| 5 | 112175675 | Detected | Detected | Detected |
| 5 | 112175830 | Detected | Detected | Detected |
| 5 | 112175852 | Detected | Detected | Detected |
| 5 | 112175930 | Detected | Detected | Detected |
| 5 | 112175945 | Detected | Detected | Detected |
| 5 | 112175951 | Detected | Detected | Detected |
| 5 | 112176063 | Not Covered | Not Covered | Detected |
| 5 | 112176117 | Not Covered | Not Covered | Detected |
| 5 | 149433596 | Detected | Not Covered | Not Covered |
| 5 | 149433597 | Detected | Detected | Not Covered |
| 5 | 149433645 | Detected | Detected | Not Covered |
| 5 | 149433673 | Detected | Detected | Not Covered |
| 5 | 149453057 | Detected | Detected | Not Covered |
| 5 | 170837543 | Detected | Detected | Not Covered |
| 7 | 55211080 | Detected | Detected | Not Covered |
| 7 | 55211097 | Detected | Detected | Not Covered |

TABLE 9-continued

| | | | | |
|---|---|---|---|---|
| 7 | 55211165 | Not Covered | Detected | Not Covered |
| 7 | 55221822 | Detected | Detected | Not Covered |
| 7 | 55221830 | Detected | Detected | Not Covered |
| 7 | 55233043 | Detected | Detected | Not Covered |
| 7 | 55233109 | Not Covered | Detected | Not Covered |
| 7 | 55241615 | Not Covered | Not Covered | Detected |
| 7 | 55241644 | Detected | Not Covered | Detected |
| 7 | 55241708 | Detected | Detected | Detected |
| 7 | 55241722 | Detected | Detected | Detected |
| 7 | 55241755 | Not Covered | Detected | Not Detected |
| 7 | 55242427 | Detected | Detected | Detected |

| Chromosome | Position | Reference |
|---|---|---|
| 7 | 55242433 | G |
| 7 | 55242452 | C |
| 7 | 55242464 | AGGAATTAAGAGAAGC (SEQ ID NO: 25) |
| 7 | 55248995 | G |
| 7 | 55249063 | G |
| 7 | 55249077 | T |
| 7 | 55249131 | G |
| 7 | 55249143 | T |
| 7 | 55259427 | G |
| 7 | 55259439 | T |
| 7 | 55259446 | A |
| 7 | 55259457 | G |
| 7 | 55259515 | T |
| 7 | 55259524 | T |
| 7 | 55259530 | G |
| 7 | 55259554 | C |
| 7 | 116339642 | G |
| 7 | 116340262 | A |
| 7 | 116412044 | G |
| 7 | 116417465 | T |
| 7 | 116417499 | C |
| 7 | 116418969 | G |
| 7 | 116418997 | C |
| 7 | 116419008 | T |
| 7 | 116422133 | T |
| 7 | 116423428 | T |
| 7 | 116423449 | G |
| 7 | 116423456 | A |

TABLE 9-continued

| | | |
|---|---|---|
| 7 | 116423474 | T |
| 7 | 116436022 | G |
| 7 | 116436097 | G |
| 7 | 128845101 | C |
| 7 | 128846040 | G |

| Chromosome | Position | Alternate |
|---|---|---|
| 7 | 55242433 | A |
| 7 | 55242452 | T |
| 7 | 55242464 | A |
| 7 | 55248995 | A |
| 7 | 55249063 | A |
| 7 | 55249077 | C |
| 7 | 55249131 | A |
| 7 | 55249143 | C |
| 7 | 55259427 | A |
| 7 | 55259439 | G |
| 7 | 55259446 | T |
| 7 | 55259457 | A |
| 7 | 55259515 | G |
| 7 | 55259524 | A |
| 7 | 55259530 | A |
| 7 | 55259554 | G |
| 7 | 116339642 | T |
| 7 | 116340262 | G |
| 7 | 116412044 | A |
| 7 | 116417465 | C |
| 7 | 116417499 | G |
| 7 | 116418969 | C |
| 7 | 116418997 | T |
| 7 | 116419008 | C |
| 7 | 116422133 | G |
| 7 | 116423428 | G |
| 7 | 116423449 | T |
| 7 | 116423456 | G |
| 7 | 116423474 | C |
| 7 | 116436022 | A |
| 7 | 116436097 | A |
| 7 | 128845101 | T |
| 7 | 128846040 | A |

TABLE 9-continued

| Chromosome | Position | Length | Mutation ID | Gene |
|---|---|---|---|---|
| 7 | 55242433 | 1 | COSM13182 | EGFR |
| 7 | 55242452 | 1 | COSM17570 | EGFR |
| 7 | 55242464 | 15 | COSM6223 | EGFR |
| 7 | 55248995 | 1 | COSM28603 | EGFR |
| 7 | 55249063 | 1 | gDNA16, COSM1451600 | EGFR |
| 7 | 55249077 | 1 | COSM13190 | EGFR |
| 7 | 55249131 | 1 | COSM12986 | EGFR |
| 7 | 55249143 | 1 | COSM28610 | EGFR |
| 7 | 55259427 | 1 | COSM53291 | EGFR |
| 7 | 55259439 | 1 | COSM13424 | EGFR |
| 7 | 55259446 | 1 | COSM6227 | EGFR |
| 7 | 55259457 | 1 | COSM13430 | EGFR |
| 7 | 55259515 | 1 | COSM6224 | EGFR |
| 7 | 55259524 | 1 | COSM6213 | EGFR |
| 7 | 55259530 | 1 | COSM14070 | EGFR |
| 7 | 55259554 | 1 | COSM13008 | EGFR |
| 7 | 116339642 | 1 | COSM706 | MET |
| 7 | 116340262 | 1 | COSM710 | MET |
| 7 | 116412044 | 1 | COSM29633 | MET |
| 7 | 116417465 | 1 | COSM1447462 | MET |
| 7 | 116417499 | 1 | COSM697 | MET |
| 7 | 116418969 | 1 | COSM43064 | MET |
| 7 | 116418997 | 1 | COSM1214928 | MET |
| 7 | 116419008 | 1 | COSM1447471 | MET |
| 7 | 116422133 | 1 | COSM1330154 | MET |
| 7 | 116423428 | 1 | COSM700 | MET |
| 7 | 116423449 | 1 | COSM48565 | MET |
| 7 | 116423456 | 1 | COSM695 | MET |
| 7 | 116423474 | 1 | COSM691 | MET |
| 7 | 116436022 | 1 | gDNA12, COSM150378 | MET |
| 7 | 116436097 | 1 | gDNA13, COSM150379 | MET |
| 7 | 128845101 | 1 | COSM13145 | SMO |
| 7 | 128846040 | 1 | COSM13147 | SMO |

| Chromosome | Position | Mutation CDS |
|---|---|---|
| 7 | 55242433 | c.2203G > A |
| 7 | 55242452 | c.2222C > T |
| 7 | 55242464 | c.2235_2249del15 |
| 7 | 55248995 | c.2293G > A |
| 7 | 55249063 | c.2361G > A |

TABLE 9-continued

| Chromosome | Position | Mutation AA | Mutation Type | Strand | Target Frequency | Sanger Detection* |
|---|---|---|---|---|---|---|
| 7 | 55249077 | c.2375T > C | | | | |
| 7 | 55249131 | c.2429G > A | | | | |
| 7 | 55249143 | c.2441T > C | | | | |
| 7 | 55259427 | c.2485G > A | | | | |
| 7 | 55259439 | c.2497T > G | | | | |
| 7 | 55259446 | c.2504A > T | | | | |
| 7 | 55259457 | c.2515G > A | | | | |
| 7 | 55259515 | c.2573T > G | | | | |
| 7 | 55259524 | c.2582T > A | | | | |
| 7 | 55259530 | c.2588G > A | | | | |
| 7 | 55259554 | c.2612C > G | | | | |
| 7 | 116339642 | c.504G > T | | | | |
| 7 | 116340262 | c.1124A > G | | | | |
| 7 | 116412044 | c.3082 + 1G > A | | | | |
| 7 | 116417465 | c.3336T > C | | | | |
| 7 | 116417499 | c.3370C > G | | | | |
| 7 | 116418969 | c.3534G > C | | | | |
| 7 | 116418997 | c.3562C > T | | | | |
| 7 | 116419008 | c.3573T > C | | | | |
| 7 | 116422133 | c.3668T > G | | | | |
| 7 | 116423428 | c.3757T > G | | | | |
| 7 | 116423449 | c.3778G > T | | | | |
| 7 | 116423456 | c.3785A > G | | | | |
| 7 | 116423474 | c.3803T > C | | | | |
| 7 | 116436022 | c.4071G > A | | | | |
| 7 | 116436097 | c.4146G > A | | | | |
| 7 | 128845101 | c.595C > T | | | | |
| 7 | 128846040 | c.970G > A | | | | |
| 7 | 55242433 | p.G735S | SNV | + | 15-35% | Detected |
| 7 | 55242452 | p.P741L | SNV | + | 15-35% | Detected |
| 7 | 55242464 | p.E746_A750delELREA | DEL | + | 15-35% | Detected |
| 7 | 55248995 | p.V765M | SNV | + | 15-35% | Detected |
| 7 | 55249063 | p.Q787Q | SNV | + | genomic | Not Covered |
| 7 | 55249077 | p.L792P | SNV | + | 15-35% | Detected |
| 7 | 55249131 | p.G810D | SNV | + | 15-35% | Detected |
| 7 | 55249143 | p.L814P | SNV | + | 15-35% | Detected |
| 7 | 55259427 | p.E829K | SNV | + | 15-35% | Detected |
| 7 | 55259439 | p.L833V | SNV | + | 15-35% | Detected |
| 7 | 55259446 | p.H835L | SNV | + | 15-35% | Detected |

TABLE 9-continued

| | | | | | | |
|---|---|---|---|---|---|---|
| 7 | 55259457 | p.A839T | SNV | + | 15-35% | Detected |
| 7 | 55259515 | p.L858R | SNV | + | 15-35% | Detected |
| 7 | 55259524 | p.L861Q | SNV | + | 15-35% | Detected |
| 7 | 55259530 | p.G863D | SNV | + | 15-35% | Detected |
| 7 | 55259554 | p.A871G | SNV | + | 15-35% | Detected |
| 7 | 116339642 | p.E168D | SNV | + | 15-35% | Detected |
| 7 | 116340262 | p.N375S | SNV | + | 15-35% | Detected |
| 7 | 116412044 | p.? | SNV | + | 15-35% | Detected |
| 7 | 116417465 | p.H1112H | SNV | + | 15-35% | Detected |
| 7 | 116417499 | p.H1124D | SNV | + | 15-35% | Detected |
| 7 | 116418969 | p.M1178I | SNV | + | 15-35% | Detected |
| 7 | 116418997 | p.R1188* | SNV | + | 15-35% | Detected |
| 7 | 116419008 | p.T1191T | SNV | + | 15-35% | Detected |
| 7 | 116422133 | p.L1223W | SNV | + | 15-35% | Detected |
| 7 | 116423428 | p.Y1253D | SNV | + | 15-35% | Detected |
| 7 | 116423449 | p.G1260C | SNV | + | 15-35% | Detected |
| 7 | 116423456 | p.K1262R | SNV | + | 15-35% | Detected |
| 7 | 116423474 | p.M1268T | SNV | + | 15-35% | Detected |
| 7 | 116436022 | p.A1357A | SNV | + | genomic | Not Covered |
| 7 | 116436097 | p.P1382P | SNV | + | genomic | Not Covered |
| 7 | 128845101 | p.R199W | SNV | + | 15-35% | Detected |
| 7 | 128846040 | p.A324T | SNV | + | 15-35% | Detected |

| Chromosome | Position | CHPv2 Detection | TSACP Detection | TSTP Detection |
|---|---|---|---|---|
| 7 | 55242433 | Detected | Detected | Detected |
| 7 | 55242452 | Detected | Detected | Detected |
| 7 | 55242464 | Detected | Detected | Detected |
| 7 | 55248995 | Detected | Detected | Detected |
| 7 | 55249063 | Detected | Detected | Detected |
| 7 | 55249077 | Detected | Detected | Detected |
| 7 | 55249131 | Detected | Detected | Detected |
| 7 | 55249143 | Detected | Detected | Detected |
| 7 | 55259427 | Not Covered | Not Covered | Detected |
| 7 | 55259439 | Not Covered | Not Covered | Detected |
| 7 | 55259446 | Not Covered | Not Covered | Detected |
| 7 | 55259457 | Not Covered | Not Covered | Detected |
| 7 | 55259515 | Detected | Detected | Detected |
| 7 | 55259524 | Detected | Detected | Detected |
| 7 | 55259530 | Detected | Detected | Detected |
| 7 | 55259554 | Detected | Detected | Detected |

TABLE 9-continued

| Chromosome | Position | | | |
|---|---|---|---|---|
| 7 | 116339642 | Detected | Detected | Detected |
| 7 | 116340262 | Detected | Detected | Detected |
| 7 | 116412044 | Not Covered | Detected | Detected |
| 7 | 116417465 | Detected | Detected | Detected |
| 7 | 116417499 | Detected | Detected | Detected |
| 7 | 116418969 | Not Covered | Not Covered | Detected |
| 7 | 116418997 | Not Covered | Not Covered | Detected |
| 7 | 116419008 | Not Covered | Not Covered | Detected |
| 7 | 116422133 | Not Covered | Not Covered | Detected |
| 7 | 116423428 | Detected | Detected | Detected |
| 7 | 116423449 | Detected | Detected | Detected |
| 7 | 116423456 | Detected | Detected | Detected |
| 7 | 116423474 | Detected | Detected | Detected |
| 7 | 116436022 | Not Covered | Not Covered | Detected |
| 7 | 116436097 | Not Covered | Not Covered | Detected |
| 7 | 128845101 | Detected | Detected | Not Covered |
| 7 | 128846040 | Detected | Detected | Not Covered |

| Chromosome | Position | Reference |
|---|---|---|
| 7 | 128846398 | C |
| 7 | 128846469 | A |
| 7 | 128850341 | G |
| 7 | 128851593 | A |
| 7 | 140453136 | A |
| 7 | 140453145 | A |
| 7 | 140453154 | T |
| 7 | 140453193 | T |
| 7 | 140481417 | C |
| 7 | 140481428 | T |
| 7 | 140481449 | A |
| 7 | 140481478 | G |
| 7 | 148508727 | T |
| 8 | 38282147 | G |
| 8 | 38285864 | G |
| 8 | 38285891 | T |
| 8 | 38285938 | G |
| 9 | 5073770 | G |
| 9 | 5073781 | C |
| 9 | 21971000 | C |
| 9 | 21971017 | G |
| 9 | 21971028 | C |

TABLE 9-continued

| | | |
|---|---|---|
| 9 | 21971036 | C |
| 9 | 21971111 | G |
| 9 | 21971120 | G |
| 9 | 21971153 | C |
| 9 | 21971186 | G |
| 9 | 80336317 | G |
| 9 | 80343489 | T |
| 9 | 80343605 | GAAAAAACAAGGA (SEQ ID NO: 26) |
| 9 | 80409345 | A |
| 9 | 80409432 | ACA |
| 9 | 80409533 | TAATAACATATAAAGTAAAACTAAAAAGTCAACATAAATATA (SEQ ID NO: 27) |

| Chromosome | Position | Alternate |
|---|---|---|
| 7 | 128846398 | T |
| 7 | 128846469 | G |
| 7 | 128850341 | T |
| 7 | 128851593 | G |
| 7 | 140453136 | T |
| 7 | 140453145 | C |
| 7 | 140453154 | C |
| 7 | 140453193 | C |
| 7 | 140481417 | A |
| 7 | 140481428 | C |
| 7 | 140481449 | G |
| 7 | 140481478 | A |
| 7 | 148508727 | A |
| 8 | 38282147 | A |
| 8 | 38285864 | A |
| 8 | 38285891 | C |
| 8 | 38285938 | A |
| 9 | 5073770 | T |
| 9 | 5073781 | A |
| 9 | 21971000 | A |
| 9 | 21971017 | A |
| 9 | 21971028 | T |
| 9 | 21971036 | A |
| 9 | 21971111 | A |
| 9 | 21971120 | A |
| 9 | 21971153 | A |
| 9 | 21971186 | A |
| 9 | 80336317 | A |

TABLE 9-continued

| Chromosome | Position | Length | Mutation ID | Gene |
|---|---|---|---|---|
| 9 | 80343489 | | TGTAC | |
| 9 | 80343605 | | G | |
| 9 | 80409345 | | G | |
| 9 | 80409432 | | TGC | |
| 9 | 80409533 | | T | |
| 7 | 128846398 | 1 | COSM216037 | SMO |
| 7 | 128846469 | 1 | gDNA14 | SMO |
| 7 | 128850341 | 1 | COSM13146 | SMO |
| 7 | 128851593 | 1 | COSM13150 | SMO |
| 7 | 140453136 | 1 | COSM476 | BRAF |
| 7 | 140453145 | 1 | COSM471 | BRAF |
| 7 | 140453154 | 1 | COSM467 | BRAF |
| 7 | 140453193 | 1 | COSM462 | BRAF |
| 7 | 140481417 | 1 | COSM450 | BRAF |
| 7 | 140481428 | 1 | COSM27986 | BRAF |
| 7 | 140481449 | 1 | COSM1448625 | BRAF |
| 7 | 140481478 | 1 | COSM6262 | BRAF |
| 7 | 148508727 | 1 | COSM37028 | EZH2 |
| 8 | 38282147 | 1 | COSM1292693 | FGFR1 |
| 8 | 38285864 | 1 | COSM187237 | FGFR1 |
| 8 | 38285891 | 1 | COSM1456955 | FGFR1 |
| 8 | 38285938 | 1 | COSM601 | FGFR1 |
| 9 | 5073770 | 1 | COSM12600 | JAK2 |
| 9 | 5073781 | 1 | COSM27063 | JAK2 |
| 9 | 21971000 | 1 | COSM12479 | CDKN2A |
| 9 | 21971017 | 1 | COSM12476 | CDKN2A |
| 9 | 21971028 | 1 | COSM12547 | CDKN2A |
| 9 | 21971036 | 1 | COSM13489 | CDKN2A |
| 9 | 21971111 | 1 | COSM12504 | CDKN2A |
| 9 | 21971120 | 1 | COSM12475 | CDKN2A |
| 9 | 21971153 | 1 | COSM13281 | CDKN2A |
| 9 | 21971186 | 1 | COSM12473 | CDKN2A |
| 9 | 80336317 | 1 | COSM1110323 | GNAQ |
| 9 | 80343489 | 4 | AMXsynt6 | GNAQ |
| 9 | 80343605 | 12 | AMXsynt7 | GNAQ |
| 9 | 80409345 | 1 | gDNA17 | GNAQ |
| 9 | 80409432 | 3 | AMXsynt8 | GNAQ |
| 9 | 80409533 | 41 | AMXsynt9 | GNAQ |

TABLE 9-continued

| Chromosome | Position | Mutation CDS |
|---|---|---|
| 7 | 128846398 | c.1234C > T |
| 7 | 128846469 | c.1264 + 41A > G |
| 7 | 128850341 | c.1604G > T |
| 7 | 128851593 | c.1918A > G |
| 7 | 140453136 | c.1799T > A |
| 7 | 140453145 | c.1790T > G |
| 7 | 140453154 | c.1781A > G |
| 7 | 140453193 | c.1742A > G |
| 7 | 140481417 | c.1391G > T |
| 7 | 140481428 | c.1380A > G |
| 7 | 140481449 | c.1359T > C |
| 7 | 140481478 | c.1330C > T |
| 7 | 148508727 | c.1937A > T |
| 8 | 38282147 | c.816C > T |
| 8 | 38285864 | c.448C > T |
| 8 | 38285891 | c.421A > G |
| 8 | 38285938 | c.374C > T |
| 9 | 5073770 | c.1849G > T |
| 9 | 5073781 | c.1860C > A |
| 9 | 21971000 | c.358G > T |
| 9 | 21971017 | c.341C > T |
| 9 | 21971028 | c.330G > A |
| 9 | 21971036 | c.322G > T |
| 9 | 21971111 | c.247C > T |
| 9 | 21971120 | c.238C > T |
| 9 | 21971153 | c.205G > T |
| 9 | 21971186 | c.172C > T |
| 9 | 80336317 | c.1002C > T |
| 9 | 80343489 | c.829_830insGTAC |
| 9 | 80343605 | c.736 − 34del12 |
| 9 | 80409345 | c.735 + 34T > C |
| 9 | 80409432 | c.679_681TGT > GCA |
| 9 | 80409533 | c.606 − 66del41 |

| Chromosome | Position | Mutation AA | Mutation Type | Strand | Target Frequency |
|---|---|---|---|---|---|
| 7 | 128846398 | p.L412F | SNV | + | 15-35% |
| 7 | 128846469 | p.(=) | SNV | + | genomic |
| 7 | 128850341 | p.W535L | SNV | + | 15-35% |
| 7 | 128851593 | p.T640A | SNV | + | 15-35% |
| 7 | 140453136 | p.V600E | SNV | − | 15-35% |

TABLE 9-continued

| | | | | | |
|---|---|---|---|---|---|
| 7 | 140453145 | p.L597R | SNV | − | 15-35% |
| 7 | 140453154 | p.D594G | SNV | − | 15-35% |
| 7 | 140453193 | p.N581S | SNV | − | 15-35% |
| 7 | 140481417 | p.G464V | SNV | − | 15-35% |
| 7 | 140481428 | p.G460G | SNV | − | 15-35% |
| 7 | 140481449 | p.P453P | SNV | − | 15-35% |
| 7 | 140481478 | p.R444W | SNV | − | 15-35% |
| 7 | 148508727 | p.Y646F | SNV | − | 15-35% |
| 8 | 38282147 | p.N272N | SNV | − | 15-35% |
| 8 | 38285864 | p.P150S | SNV | − | 15-35% |
| 8 | 38285891 | p.T141A | SNV | − | 15-35% |
| 8 | 38285938 | p.S125L | SNV | − | 15-35% |
| 9 | 5073770 | p.V617F | SNV | + | 15-35% |
| 9 | 5073781 | p.D620E | SNV | + | 15-35% |
| 9 | 21971000 | p.E120* | SNV | − | 15-35% |
| 9 | 21971017 | p.P114L | SNV | − | 15-35% |
| 9 | 21971028 | p.W110* | SNV | − | 15-35% |
| 9 | 21971036 | p.D108Y | SNV | − | 15-35% |
| 9 | 21971111 | p.H83Y | SNV | − | 15-35% |
| 9 | 21971120 | p.R80* | SNV | − | 15-35% |
| 9 | 21971153 | p.E69* | SNV | − | 15-35% |
| 9 | 21971186 | p.R58* | SNV | − | 15-35% |
| 9 | 80336317 | p.T334T | SNV | − | 15-35% |
| 9 | 80343489 | p.D277fs*20 | INS | − | 15-35% |
| 9 | 80343605 | p.? | DEL | − | 15-35% |
| 9 | 80409345 | p.(=) | SNV | − | genomic |
| 9 | 80409432 | p.M227_F228 > SI | MNV | − | 15-35% |
| 9 | 80409533 | p.? | DEL | − | 15-35% |

| Chromosome | Position | Sanger Detection* | CHPv2 Detection | TSACP Detection | TSTP Detection |
|---|---|---|---|---|---|
| 7 | 128846398 | Detected | Detected | Detected | Not Covered |
| 7 | 128846469 | Not Covered | Not Covered | Detected | Not Covered |
| 7 | 128850341 | Detected | Detected | Detected | Not Covered |
| 7 | 128851593 | Detected | Detected | Detected | Not Covered |
| 7 | 140453136 | Detected | Detected | Detected | Detected |
| 7 | 140453145 | Detected | Detected | Detected | Detected |
| 7 | 140453154 | Detected | Detected | Detected | Detected |
| 7 | 140453193 | Detected | Detected | Detected | Detected |
| 7 | 140481417 | Detected | Detected | Detected | Detected |
| 7 | 140481428 | Detected | Detected | Detected | Detected |
| 7 | 140481449 | Detected | Detected | Detected | Detected |

TABLE 9-continued

| | | | | | |
|---|---|---|---|---|---|
| 7 | 140481478 | Detected | Detected | Detected | Detected |
| 7 | 148508727 | Detected | Detected | Not Covered | Not Covered |
| 8 | 38282147 | Detected | Detected | Not Covered | Not Covered |
| 8 | 38285864 | Detected | Detected | Not Covered | Not Covered |
| 8 | 38285891 | Detected | Detected | Not Covered | Not Covered |
| 8 | 38285938 | Detected | Detected | Detected | Not Covered |
| 9 | 5073770 | Detected | Detected | Detected | Not Covered |
| 9 | 5073781 | Detected | Detected | Detected | Not Covered |
| 9 | 21971000 | Detected | Detected | Not Covered | Not Covered |
| 9 | 21971017 | Detected | Detected | Not Covered | Not Covered |
| 9 | 21971028 | Detected | Detected | Not Covered | Not Covered |
| 9 | 21971036 | Detected | Detected | Not Covered | Not Covered |
| 9 | 21971111 | Detected | Detected | Not Covered | Not Covered |
| 9 | 21971120 | Detected | Detected | Not Covered | Not Covered |
| 9 | 21971153 | Detected | Detected | Not Detected | Not Covered |
| 9 | 21971186 | Detected | Detected | Detected | Not Covered |
| 9 | 80336317 | Detected | Not Covered | Detected | Not Covered |
| 9 | 80343489 | Detected | Not Covered | Detected | Detected |
| 9 | 80343605 | Detected | Not Covered | Detected | Not Detected |
| 9 | 80409345 | Not Covered | Not Covered | Detected | Not Covered |
| 9 | 80409432 | Detected | Detected | Detected | Detected |
| 9 | 80409533 | Detected | Not Covered | Not Detected | Not Detected |

| Chromosome | Position | Reference |
|---|---|---|
| 9 | 80412493 | C |
| 9 | 80412518 | T |
| 9 | 133738342 | C |
| 9 | 133738349 | G |
| 9 | 133738357 | T |
| 9 | 133738363 | G |
| 9 | 133747520 | A |
| 9 | 133747571 | T |
| 9 | 133748391 | T |
| 9 | 133748403 | A |
| 9 | 133748414 | T |
| 9 | 133750319 | C |
| 9 | 133750356 | A |
| 9 | 139390779 | G |
| 9 | 139390804 | CG |
| 9 | 139390816 | G |
| 9 | 139390873 | G |

TABLE 9-continued

| | | |
|---|---|---|
| 9 | 139397768 | A |
| 9 | 139397776 | G |
| 9 | 139399344 | A |
| 9 | 139399350 | C |
| 9 | 139399365 | A |
| 9 | 139399422 | A |
| 10 | 43609096 | T |
| 10 | 43609102 | T |
| 10 | 43609942 | GAGCTGTGCCGCA (SEQ ID NO: 28) |
| 10 | 43609990 | G |
| 10 | 43610039 | C |
| 10 | 43613840 | G |
| 10 | 43613843 | G |
| 10 | 43615568 | GC |
| 10 | 43615622 | G |
| 10 | 43617416 | T |

| Chromosome | Position | Alternate |
|---|---|---|
| 9 | 80412493 | T |
| 9 | 80412518 | A |
| 9 | 133738342 | G |
| 9 | 133738349 | A |
| 9 | 133738357 | C |
| 9 | 133738363 | A |
| 9 | 133747520 | G |
| 9 | 133747571 | TGCC |
| 9 | 133748391 | C |
| 9 | 133748403 | G |
| 9 | 133748414 | G |
| 9 | 133750319 | A |
| 9 | 133750356 | G |
| 9 | 139390779 | T |
| 9 | 139390804 | C |
| 9 | 139390816 | A |
| 9 | 139390873 | A |
| 9 | 139397768 | G |
| 9 | 139397776 | A |
| 9 | 139399344 | G |
| 9 | 139399350 | G |
| 9 | 139399365 | G |

TABLE 9-continued

| | | | |
|---|---|---|---|
| 9 | 139399422 | | G |
| 10 | 43609096 | | C |
| 10 | 43609102 | | C |
| 10 | 43609942 | | AGCT |
| 10 | 43609990 | | A |
| 10 | 43610039 | | A |
| 10 | 43613840 | | C |
| 10 | 43613843 | | T |
| 10 | 43615568 | | TT |
| 10 | 43615622 | | A |
| 10 | 43617416 | | C |

| Chromosome | Position | Length | Mutation ID | Gene |
|---|---|---|---|---|
| 9 | 80412493 | 1 | COSM52975 | GNAQ |
| 9 | 80412518 | 1 | COSM1463119 | GNAQ |
| 9 | 133738342 | 1 | COSM12631 | ABL1 |
| 9 | 133738349 | 1 | COSM12577 | ABL1 |
| 9 | 133738357 | 1 | COSM12576 | ABL1 |
| 9 | 133738363 | 1 | COSM12573 | ABL1 |
| 9 | 133747520 | 1 | COSM12602 | ABL1 |
| 9 | 133747571 | 3 | COSM235737 | ABL1 |
| 9 | 133748391 | 1 | COSM12578 | ABL1 |
| 9 | 133748403 | 1 | COSM12611 | ABL1 |
| 9 | 133748414 | 1 | COSM12605 | ABL1 |
| 9 | 133750319 | 1 | COSM49071 | ABL1 |
| 9 | 133750356 | 1 | COSM12604 | ABL1 |
| 9 | 139390779 | 1 | COSM87862 | NOTCH1 |
| 9 | 139390804 | 1 | COSM13070 | NOTCH1 |
| 9 | 139390816 | 1 | COSM12776 | NOTCH1 |
| 9 | 139390873 | 1 | COSM13061 | NOTCH1 |
| 9 | 139397768 | 1 | COSM13048 | NOTCH1 |
| 9 | 139397776 | 1 | COSM308587 | NOTCH1 |
| 9 | 139399344 | 1 | COSM12771 | NOTCH1 |
| 9 | 139399350 | 1 | COSM13053 | NOTCH1 |
| 9 | 139399365 | 1 | COSM13042 | NOTCH1 |
| 9 | 139399422 | 1 | COSM12772 | NOTCH1 |
| 10 | 43609096 | 1 | COSM29803 | RET |
| 10 | 43609102 | 1 | COSM29804 | RET |
| 10 | 43609942 | 13 | COSM1048 | RET |
| 10 | 43609990 | 1 | COSM1223553 | RET |
| 10 | 43610039 | 1 | COSM976 | RET |

TABLE 9-continued

| | | | | |
|---|---|---|---|---|
| 10 | 43613840 | 1 | COSM21338 | RET |
| 10 | 43613843 | 1 | gDNA18 | RET |
| 10 | 43615568 | 3 | COSM977 | RET |
| 10 | 43615622 | 1 | COSM963 | RET |
| 10 | 43617416 | 1 | COSM965 | RET |

| Chromosome | Position | Mutation CDS |
|---|---|---|
| 9 | 80412493 | c.548G > A |
| 9 | 80412518 | c.523A > T |
| 9 | 133738342 | c.742C > G |
| 9 | 133738349 | c.749G > A |
| 9 | 133738357 | c.757T > C |
| 9 | 133738363 | c.763G > A |
| 9 | 133747520 | c.827A > G |
| 9 | 133747571 | c.878_879insGCC |
| 9 | 133748391 | c.1052T > C |
| 9 | 133748403 | c.1064A > G |
| 9 | 133748414 | c.1075T > G |
| 9 | 133750319 | c.1150C > A |
| 9 | 133750356 | c.1187A > G |
| 9 | 139390779 | c.7412C > A |
| 9 | 139390804 | c.7386delC |
| 9 | 139390816 | c.7375C > T |
| 9 | 139390873 | c.7318C > T |
| 9 | 139397768 | c.5033T > C |
| 9 | 139397776 | c.5025C > T |
| 9 | 139399344 | c.4799T > C |
| 9 | 139399350 | c.4793G > C |
| 9 | 139399365 | c.4778T > C |
| 9 | 139399422 | c.4721T > C |
| 10 | 43609096 | c.1852T > C |
| 10 | 43609102 | c.1858T > C |
| 10 | 43609942 | c.1894_1906 > AGCT |
| 10 | 43609990 | c.1942G > A |
| 10 | 43610039 | c.1991C > A |
| 10 | 43613840 | c.2304G > C |
| 10 | 43613843 | c.2307T > A |
| 10 | 43615568 | c.2647_2648GC > TT |
| 10 | 43615622 | c.2701G > A |
| 10 | 43617416 | c.2753T > C |

TABLE 9-continued

| Chromosome | Position | Mutation AA | Mutation Type | Strand | Target Frequency |
|---|---|---|---|---|---|
| 9 | 80412493 | p.R183Q | SNV | − | 15-35% |
| 9 | 80412518 | p.T175S | SNV | − | 15-35% |
| 9 | 133738342 | p.L248V | SNV | + | 15-35% |
| 9 | 133738349 | p.G250E | SNV | + | 15-35% |
| 9 | 133738357 | p.Y253H | SNV | + | 15-35% |
| 9 | 133738363 | p.E255K | SNV | + | 15-35% |
| 9 | 133747520 | p.D276G | SNV | + | 15-35% |
| 9 | 133747571 | p.I293 > MP | INS | + | 15-35% |
| 9 | 133748391 | p.M351T | SNV | + | 15-35% |
| 9 | 133748403 | p.E355G | SNV | + | 15-35% |
| 9 | 133748414 | p.F359V | SNV | + | 15-35% |
| 9 | 133750319 | p.L384M | SNV | + | 15-35% |
| 9 | 133750356 | p.H396R | SNV | + | 15-35% |
| 9 | 139390779 | p.S2471* | SNV | − | 15-35% |
| 9 | 139390804 | p.A2463fs*14 | DEL | − | 15-35% |
| 9 | 139390816 | p.Q2459* | SNV | − | 15-35% |
| 9 | 139390873 | p.Q2440* | SNV | − | 15-35% |
| 9 | 139397768 | p.L1678P | SNV | − | 15-35% |
| 9 | 139397776 | p.I1675I | SNV | − | 15-35% |
| 9 | 139399344 | p.L1600P | SNV | − | 15-35% |
| 9 | 139399350 | p.R1598P | SNV | − | 15-35% |
| 9 | 139399365 | p.L1593P | SNV | − | 15-35% |
| 9 | 139399422 | p.L1574P | SNV | − | 15-35% |
| 10 | 43609096 | p.C618R | SNV | + | 15-35% |
| 10 | 43609102 | p.C620R | SNV | + | 15-35% |
| 10 | 43609942 | p.E632_T636 > SS | Complex | + | 15-35% |
| 10 | 43609990 | p.V648I | SNV | + | 15-35% |
| 10 | 43610039 | p.A664D | SNV | + | 15-35% |
| 10 | 43613840 | p.E768D | SNV | + | 15-35% |
| 10 | 43613843 | p.L769L | SNV | + | genomic |
| 10 | 43615568 | p.A883F | MNV | + | 15-35% |
| 10 | 43615622 | p.E901K | SNV | + | 15-35% |
| 10 | 43617416 | p.M918T | SNV | + | 15-35% |

| Chromosome | Position | Sanger Detection* | CHPv2 Detection | TSACP Detection | TSTP Detection |
|---|---|---|---|---|---|
| 9 | 80412493 | Detected | Not Covered | Detected | Detected |
| 9 | 80412518 | Detected | Not Covered | Detected | Detected |
| 9 | 133738342 | Detected | Detected | Detected | Not Covered |
| 9 | 133738349 | Detected | Detected | Detected | Not Covered |
| 9 | 133738357 | Detected | Detected | Detected | Not Covered |

TABLE 9-continued

| | | | | |
|---|---|---|---|---|
| 9 | 133738363 | Detected | Detected | Detected | Not Covered |
| 9 | 133747520 | Detected | Detected | Detected | Not Covered |
| 9 | 133747571 | Detected | Not Covered | Detected | Not Covered |
| 9 | 133748391 | Detected | Detected | Detected | Not Covered |
| 9 | 133748403 | Detected | Detected | Detected | Not Covered |
| 9 | 133748414 | Detected | Detected | Detected | Not Covered |
| 9 | 133750319 | Detected | Detected | Not Covered | Not Covered |
| 9 | 133750356 | Detected | Detected | Detected | Not Covered |
| 9 | 139390779 | Detected | Detected | Not Covered | Not Covered |
| 9 | 139390804 | Detected | Not Detected | Not Covered | Not Covered |
| 9 | 139390816 | Detected | Detected | Not Covered | Not Covered |
| 9 | 139390873 | Detected | Detected | Not Covered | Not Covered |
| 9 | 139397768 | Detected | Detected | Detected | Not Covered |
| 9 | 139397776 | Detected | Detected | Detected | Not Covered |
| 9 | 139399344 | Detected | Detected | Detected | Not Covered |
| 9 | 139399350 | Detected | Detected | Detected | Not Covered |
| 9 | 139399365 | Detected | Detected | Detected | Not Covered |
| 9 | 139399422 | Detected | Detected | Detected | Not Covered |
| 10 | 43609096 | Detected | Detected | Detected | Not Covered |
| 10 | 43609102 | Detected | Detected | Detected | Not Covered |
| 10 | 43609942 | Detected | Detected | Detected | Not Covered |
| 10 | 43609990 | Detected | Detected | Detected | Not Covered |
| 10 | 43610039 | Detected | Not Covered | Detected | Not Covered |
| 10 | 43613840 | Detected | Detected | Detected | Not Covered |
| 10 | 43613843 | Not Covered | Detected | Detected | Not Covered |
| 10 | 43615568 | Detected | Detected | Detected | Not Covered |
| 10 | 43615622 | Detected | Detected | Detected | Not Covered |
| 10 | 43617416 | Detected | Detected | Detected | Not Covered |

| Chromosome | Position | Reference |
|---|---|---|
| 10 | 89624245 | G |
| 10 | 89624266 | A |
| 10 | 89624275 | C |
| 10 | 89624297 | A |
| 10 | 89653686 | A |
| 10 | 89653782 | A |
| 10 | 89653814 | C |
| 10 | 89653844 | A |
| 10 | 89653858 | T |
| 10 | 89653865 | A |
| 10 | 89685271 | T |

TABLE 9-continued

| Chromosome | Position | Alternate |
|---|---|---|
| 10 | 89685307 | T |
| 10 | 89685319 | G |
| 10 | 89690805 | G |
| 10 | 89690818 | TTA |
| 10 | 89690838 | A |
| 10 | 89690847 | G |
| 10 | 89692779 | A |
| 10 | 89692818 | T |
| 10 | 89692830 | G |
| 10 | 89692850 | C |
| 10 | 89692911 | G |
| 10 | 89692965 | A |
| 10 | 89692980 | A |
| 10 | 89692993 | G |
| 10 | 89711855 | CT |
| 10 | 89711960 | T |
| 10 | 89711972 | AGAT |
| 10 | 89711992 | C |
| 10 | 89711997 | G |
| 10 | 89717672 | C |
| 10 | 89717678 | G |
| 10 | 89717696 | T |

| Chromosome | Position | Alternate |
|---|---|---|
| 10 | 89624245 | T |
| 10 | 89624266 | G |
| 10 | 89624275 | T |
| 10 | 89624297 | G |
| 10 | 89653686 | G |
| 10 | 89653782 | G |
| 10 | 89653814 | T |
| 10 | 89653844 | G |
| 10 | 89653858 | C |
| 10 | 89653865 | G |
| 10 | 89685271 | G |
| 10 | 89685307 | C |
| 10 | 89685319 | A |
| 10 | 89690805 | A |
| 10 | 89690818 | T |
| 10 | 89690838 | C |
| 10 | 89690847 | A |

TABLE 9-continued

| | | | | |
|---|---|---|---|---|
| | 10 | 89692779 | | G |
| | 10 | 89692818 | | C |
| | 10 | 89692830 | | T |
| | 10 | 89692850 | | G |
| | 10 | 89692911 | | A |
| | 10 | 89692965 | | G |
| | 10 | 89692980 | | G |
| | 10 | 89692993 | | T |
| | 10 | 89711855 | | C |
| | 10 | 89711960 | | C |
| | 10 | 89711972 | | A |
| | 10 | 89711992 | | A |
| | 10 | 89711997 | | A |
| | 10 | 89717672 | | T |
| | 10 | 89717678 | | T |
| | 10 | 89717696 | | C |

| Chromosome | Position | Length | Mutation ID | Gene |
|---|---|---|---|---|
| 10 | 89624245 | 1 | COSM5298 | PTEN |
| 10 | 89624266 | 1 | COSM5101 | PTEN |
| 10 | 89624275 | 1 | COSM5153 | PTEN |
| 10 | 89624297 | 1 | COSM5107 | PTEN |
| 10 | 89653686 | 1 | gDNA34 | PTEN |
| 10 | 89653782 | 1 | COSM5134 | PTEN |
| 10 | 89653814 | 1 | COSM5142 | PTEN |
| 10 | 89653844 | 1 | COSM5050 | PTEN |
| 10 | 89653858 | 1 | COSM1349479 | PTEN |
| 10 | 89653865 | 1 | COSM5129 | PTEN |
| 10 | 89685271 | 1 | COSM5257 | PTEN |
| 10 | 89685307 | 1 | COSM5036 | PTEN |
| 10 | 89685319 | 1 | COSM5916 | PTEN |
| 10 | 89690805 | 1 | COSM5102 | PTEN |
| 10 | 89690818 | 2 | COSM4956 | PTEN |
| 10 | 89690838 | 1 | COSM5205 | PTEN |
| 10 | 89690847 | 1 | COSM5983 | PTEN |
| 10 | 89692779 | 1 | COSM5139 | PTEN |
| 10 | 89692818 | 1 | COSM5109 | PTEN |
| 10 | 89692830 | 1 | COSM5266 | PTEN |
| 10 | 89692850 | 1 | COSM5199 | PTEN |
| 10 | 89692911 | 1 | COSM5123 | PTEN |
| 10 | 89692965 | 1 | COSM5130 | PTEN |

TABLE 9-continued

| | | | | |
|---|---|---|---|---|
| 10 | 89692980 | 1 | COSM5144 | PTEN |
| 10 | 89692993 | 1 | COSM5287 | PTEN |
| 10 | 89711855 | 1 | COSM5907 | PTEN |
| 10 | 89711960 | 1 | COSM35406 | PTEN |
| 10 | 89711972 | 3 | COSM4978 | PTEN |
| 10 | 89711992 | 1 | COSM5279 | PTEN |
| 10 | 89711997 | 1 | COSM5072 | PTEN |
| 10 | 89717672 | 1 | COSM5154 | PTEN |
| 10 | 89717678 | 1 | COSM5292 | PTEN |
| 10 | 89717696 | 1 | COSM35849 | PTEN |

| Chromosome | Position | Mutation CDS |
|---|---|---|
| 10 | 89624245 | c.19G > T |
| 10 | 89624266 | c.40A > G |
| 10 | 89624275 | c.49C > T |
| 10 | 89624297 | c.71A > G |
| 10 | 89653686 | c.80 − 96A > G |
| 10 | 89653782 | c.80A > G |
| 10 | 89653814 | c.112C > T |
| 10 | 89653844 | c.142A > G |
| 10 | 89653858 | c.156T > C |
| 10 | 89653865 | c.163A > G |
| 10 | 89685271 | c.166T > G |
| 10 | 89685307 | c.202T > C |
| 10 | 89685319 | c.209 + 5G > A |
| 10 | 89690805 | c.212G > A |
| 10 | 89690818 | c.227_228delAT |
| 10 | 89690838 | c.245A > C |
| 10 | 89690847 | c.253 + 1G > A |
| 10 | 89692779 | c.263A > G |
| 10 | 89692818 | c.302T > C |
| 10 | 89692830 | c.314G > T |
| 10 | 89692850 | c.334C > G |
| 10 | 89692911 | c.395G > A |
| 10 | 89692965 | c.449A > G |
| 10 | 89692980 | c.464A > G |
| 10 | 89692993 | c.477G > T |
| 10 | 89711855 | c.493 − 12delT |
| 10 | 89711960 | c.578T > C |
| 10 | 89711972 | c.595_597delATG |
| 10 | 89711992 | c.610C > A |

TABLE 9-continued

| | | | |
|---|---|---|---|
| 10 | 89711997 | c.615G > A | |
| 10 | 89717672 | c.697C > T | |
| 10 | 89717678 | c.703G > T | |
| 10 | 89717696 | c.721T > C | |

| Chromosome | Position | Mutation AA | Mutation Type | Strand | Target Frequency |
|---|---|---|---|---|---|
| 10 | 89624245 | p.E7* | SNV | + | 15-35% |
| 10 | 89624266 | p.R14G | SNV | + | 15-35% |
| 10 | 89624275 | p.Q17* | SNV | + | 15-35% |
| 10 | 89624297 | p.D24G | SNV | + | 15-35% |
| 10 | 89653686 | p.(=) | SNV | + | genomic |
| 10 | 89653782 | p.Y27C | SNV | + | 15-35% |
| 10 | 89653814 | p.P38S | SNV | + | 15-35% |
| 10 | 89653844 | p.N48D | SNV | + | 15-35% |
| 10 | 89653858 | p.D52D | SNV | + | 15-35% |
| 10 | 89653865 | p.R55G | SNV | + | 15-35% |
| 10 | 89685271 | p.F56V | SNV | + | 15-35% |
| 10 | 89685307 | p.Y68H | SNV | + | 15-35% |
| 10 | 89685319 | p.? | SNV | + | 15-35% |
| 10 | 89690805 | p.C71Y | SNV | + | 15-35% |
| 10 | 89690818 | p.Y76fs*1 | DEL | + | 15-35% |
| 10 | 89690838 | p.N82T | SNV | + | 15-35% |
| 10 | 89690847 | p.? | SNV | + | 15-35% |
| 10 | 89692779 | p.Y88C | SNV | + | 15-35% |
| 10 | 89692818 | p.I101T | SNV | + | 15-35% |
| 10 | 89692830 | p.C105F | SNV | + | 15-35% |
| 10 | 89692850 | p.L112V | SNV | + | 15-35% |
| 10 | 89692911 | p.G132D | SNV | + | 15-35% |
| 10 | 89692965 | p.E150G | SNV | + | 15-35% |
| 10 | 89692980 | p.Y155C | SNV | + | 15-35% |
| 10 | 89692993 | p.R159S | SNV | + | 15-35% |
| 10 | 89711855 | p.? | DEL | + | 15-35% |
| 10 | 89711960 | p.L193P | SNV | + | 15-35% |
| 10 | 89711972 | p.M199del | DEL | + | 15-35% |
| 10 | 89711992 | p.P204T | SNV | + | 15-35% |
| 10 | 89711997 | p.M205I | SNV | + | 15-35% |
| 10 | 89717672 | p.R233* | SNV | + | 15-35% |
| 10 | 89717678 | p.E235* | SNV | + | 15-35% |
| 10 | 89717696 | p.F241L | SNV | + | 15-35% |

TABLE 9-continued

| Chromosome | Position | Sanger Detection* | CHPv2 Detection | TSACP Detection | TSTP Detection |
|---|---|---|---|---|---|
| 10 | 89624245 | Detected | Detected | Detected | Detected |
| 10 | 89624266 | Detected | Detected | Detected | Detected |
| 10 | 89624275 | Detected | Detected | Detected | Detected |
| 10 | 89624297 | Detected | Detected | Detected | Detected |
| 10 | 89653686 | Not Covered | Not Covered | Not Covered | Detected |
| 10 | 89653782 | Detected | Not Covered | Not Covered | Detected |
| 10 | 89653814 | Detected | Not Covered | Not Covered | Detected |
| 10 | 89653844 | Detected | Not Covered | Not Covered | Detected |
| 10 | 89653858 | Detected | Not Covered | Not Covered | Detected |
| 10 | 89653865 | Detected | Not Covered | Not Covered | Detected |
| 10 | 89685271 | Detected | Detected | Not Covered | Detected |
| 10 | 89685307 | Detected | Detected | Detected | Detected |
| 10 | 89685319 | Detected | Detected | Detected | Detected |
| 10 | 89690805 | Detected | Not Covered | Not Covered | Detected |
| 10 | 89690818 | Detected | Not Covered | Not Covered | Detected |
| 10 | 89690838 | Detected | Not Covered | Not Covered | Detected |
| 10 | 89690847 | Detected | Not Covered | Not Covered | Detected |
| 10 | 89692779 | Detected | Not Covered | Not Covered | Detected |
| 10 | 89692818 | Detected | Detected | Not Covered | Detected |
| 10 | 89692830 | Detected | Detected | Not Covered | Detected |
| 10 | 89692850 | Detected | Detected | Not Covered | Detected |
| 10 | 89692911 | Detected | Detected | Not Covered | Detected |
| 10 | 89692965 | Detected | Not Covered | Not Covered | Detected |
| 10 | 89692980 | Detected | Not Covered | Not Covered | Detected |
| 10 | 89692993 | Detected | Not Covered | Not Covered | Detected |
| 10 | 89711855 | Detected | Detected | Not Covered | Not Detected |
| 10 | 89711960 | Detected | Not Covered | Detected | Detected |
| 10 | 89711972 | Detected | Not Covered | Detected | Detected |
| 10 | 89711992 | Detected | Not Covered | Detected | Detected |
| 10 | 89711997 | Detected | Not Covered | Detected | Detected |
| 10 | 89717672 | Detected | Detected | Detected | Detected |
| 10 | 89717678 | Detected | Detected | Detected | Detected |
| 10 | 89717696 | Detected | Detected | Detected | Detected |

| Chromosome | Position | Reference |
|---|---|---|
| 10 | 89717762 | A |
| 10 | 89717769 | TA |
| 10 | 89720728 | A |
| 10 | 89720744 | G |
| 10 | 89720798 | GTACT |

TABLE 9-continued

| Chromosome | Position | |
|---|---|---|
| 10 | 89720874 | A |
| 10 | 89720907 | T |
| 10 | 89725042 | A |
| 10 | 89725056 | TTC |
| 10 | 89725072 | A |
| 10 | 89725108 | C |
| 10 | 123258034 | A |
| 10 | 123274774 | A |
| 10 | 123274794 | T |
| 10 | 123274810 | T |
| 10 | 123279503 | T |
| 10 | 123279519 | C |
| 10 | 123279677 | G |
| 11 | 533874 | T |
| 11 | 533881 | C |
| 11 | 534242 | A |
| 11 | 534288 | C |
| 11 | 108117798 | C |
| 11 | 108119823 | T |
| 11 | 108123551 | C |
| 11 | 108123641 | T |
| 11 | 108138003 | T |
| 11 | 108155132 | G |
| 11 | 108170479 | G |
| 11 | 108170587 | C |
| 11 | 108172374 | G |
| 11 | 108172385 | C |
| 11 | 108172421 | G |

| Chromosome | Position | Alternate |
|---|---|---|
| 10 | 89717762 | T |
| 10 | 89717769 | T |
| 10 | 89720728 | G |
| 10 | 89720744 | T |
| 10 | 89720798 | G |
| 10 | 89720874 | G |
| 10 | 89720907 | G |
| 10 | 89725042 | G |
| 10 | 89725056 | T |
| 10 | 89725072 | G |
| 10 | 89725108 | G |

TABLE 9-continued

| | | | |
|---|---|---|---|
| 10 | 123258034 | | T |
| 10 | 123274774 | | G |
| 10 | 123274794 | | C |
| 10 | 123274810 | | C |
| 10 | 123279503 | | C |
| 10 | 123279519 | | T |
| 10 | 123279677 | | C |
| 11 | 533874 | | C |
| 11 | 533881 | | T |
| 11 | 534242 | | G |
| 11 | 534288 | | A |
| 11 | 108117798 | | T |
| 11 | 108119823 | | C |
| 11 | 108123551 | | T |
| 11 | 108123641 | | A |
| 11 | 108138003 | | C |
| 11 | 108155132 | | A |
| 11 | 108170479 | | T |
| 11 | 108170587 | | G |
| 11 | 108172374 | | T |
| 11 | 108172385 | | T |
| 11 | 108172421 | | C |

| Chromosome | Position | Length | Mutation ID | Gene |
|---|---|---|---|---|
| 10 | 89717762 | 1 | COSM43075 | PTEN |
| 10 | 89717769 | 1 | COSM5809 | PTEN |
| 10 | 89720728 | 1 | COSM1349606 | PTEN |
| 10 | 89720744 | 1 | COSM5312 | PTEN |
| 10 | 89720798 | 4 | COSM4958 | PTEN |
| 10 | 89720874 | 1 | COSM1349625 | PTEN |
| 10 | 89720907 | 1 | gDNA19 | PTEN |
| 10 | 89725042 | 1 | COSM5966 | PTEN |
| 10 | 89725056 | 2 | COSM4936 | PTEN |
| 10 | 89725072 | 1 | COSM1349633 | PTEN |
| 10 | 89725108 | 1 | COSM23645 | PTEN |
| 10 | 123258034 | 1 | COSM36912 | FGFR2 |
| 10 | 123274774 | 1 | COSM36906 | FGFR2 |
| 10 | 123274794 | 1 | COSM36904 | FGFR2 |
| 10 | 123274810 | 1 | COSM1346272 | FGFR2 |
| 10 | 123279503 | 1 | COSM36901 | FGFR2 |
| 10 | 123279519 | 1 | COSM29824 | FGFR2 |

TABLE 9-continued

| | | | | |
|---|---|---|---|---|
| 10 | 123279677 | 1 | COSM36903 | FGFR2 |
| 11 | 533874 | 1 | COSM499 | HRAS |
| 11 | 533881 | 1 | COSM495 | HRAS |
| 11 | 534242 | 1 | gDNA20, COSM249860 | HRAS |
| 11 | 534288 | 1 | COSM483 | HRAS |
| 11 | 108117798 | 1 | COSM21323 | ATM |
| 11 | 108119823 | 1 | COSM21825 | ATM |
| 11 | 108123551 | 1 | COSM22499 | ATM |
| 11 | 108123641 | 1 | COSM1158828 | ATM |
| 11 | 108138003 | 1 | COSM21826 | ATM |
| 11 | 108155132 | 1 | COSM22507 | ATM |
| 11 | 108170479 | 1 | COSM21920 | ATM |
| 11 | 108170587 | 1 | COSM218294 | ATM |
| 11 | 108172374 | 1 | COSM49005 | ATM |
| 11 | 108172385 | 1 | COSM172204 | ATM |
| 11 | 108172421 | 1 | COSM21918 | ATM |

| Chromosome | Position | Mutation CDS |
|---|---|---|
| 10 | 89717762 | c.787A > T |
| 10 | 89717769 | c.800delA |
| 10 | 89720728 | c.879A > G |
| 10 | 89720744 | c.895G > T |
| 10 | 89720798 | c.955_958delACTT |
| 10 | 89720874 | c.1025A > G |
| 10 | 89720907 | c.1026 + 32T > G |
| 10 | 89725042 | c.1027 − 2A > G |
| 10 | 89725056 | c.1040_1041delTC |
| 10 | 89725072 | c.1055A > G |
| 10 | 89725108 | c.1091C > G |
| 10 | 123258034 | c.1647T > A |
| 10 | 123274774 | c.1144T > C |
| 10 | 123274794 | c.1124A > G |
| 10 | 123274810 | c.1108A > G |
| 10 | 123279503 | c.929A > G |
| 10 | 123279519 | c.913G > A |
| 10 | 123279677 | c.755C > G |
| 11 | 533874 | c.182A > G |
| 11 | 533881 | c.175G > A |
| 11 | 534242 | c.81T > C |
| 11 | 534288 | c.35G > T |
| 11 | 108117798 | c.1009C > T |

TABLE 9-continued

| | 11 | 108119823 | c.1229T > C | | |
| | 11 | 108123551 | c.1810C > T | | |
| | 11 | 108123641 | c.1898 + 2T > A | | |
| | 11 | 108138003 | c.2572T > C | | |
| | 11 | 108155132 | c.3925G > A | | |
| | 11 | 108170479 | c.5044G > T | | |
| | 11 | 108170587 | c.5152C > G | | |
| | 11 | 108172374 | c.5178 - 1G > T | | |
| | 11 | 108172385 | c.5188C > T | | |
| | 11 | 108172421 | c.5224G > C | | |

| Chromosome | Position | Mutation AA | Mutation Type | Strand | Target Frequency |
|---|---|---|---|---|---|
| 10 | 89717762 | p.K263* | SNV | + | 15-35% |
| 10 | 89717769 | p.K267fs*9 | DEL | + | 15-35% |
| 10 | 89720728 | p.G293G | SNV | + | 15-35% |
| 10 | 89720744 | p.E299* | SNV | + | 15-35% |
| 10 | 89720798 | p.T319fs*1 | DEL | + | 15-35% |
| 10 | 89720874 | p.K342R | SNV | + | 15-35% |
| 10 | 89720907 | p.(=) | SNV | + | genomic |
| 10 | 89725042 | p.? | SNV | + | 15-35% |
| 10 | 89725056 | p.F347fs*13 | DEL | + | 15-35% |
| 10 | 89725072 | p.E352G | SNV | + | 15-35% |
| 10 | 89725108 | p.S364C | SNV | + | 15-35% |
| 10 | 123258034 | p.N549K | SNV | - | 5-15% |
| 10 | 123274774 | p.C382R | SNV | - | 5-15% |
| 10 | 123274794 | p.Y375C | SNV | - | 5-15% |
| 10 | 123274810 | p.T370A | SNV | - | 5-15% |
| 10 | 123279503 | p.K310R | SNV | - | 5-15% |
| 10 | 123279519 | p.G305R | SNV | - | 5-15% |
| 10 | 123279677 | p.S252W | SNV | - | 5-15% |
| 11 | 533874 | p.Q61R | SNV | - | 5-15% |
| 11 | 533881 | p.A59T | SNV | - | 5-15% |
| 11 | 534242 | p.H27H | SNV | - | genomic |
| 11 | 534288 | p.G12V | SNV | - | 5-15% |
| 11 | 108117798 | p.R337C | SNV | + | 5-15% |
| 11 | 108119823 | p.V410A | SNV | + | 5-15% |
| 11 | 108123551 | p.P604S | SNV | + | 5-15% |
| 11 | 108123641 | p.? | SNV | + | 5-15% |
| 11 | 108138003 | p.F858L | SNV | + | 5-15% |
| 11 | 108155132 | p.A1309T | SNV | + | 5-15% |

TABLE 9-continued

| | | | | | |
|---|---|---|---|---|---|
| 11 | 108170479 | p.D1682Y | SNV | + | 5-15% |
| 11 | 108170587 | p.L1718V | SNV | + | 5-15% |
| 11 | 108172374 | p.? | SNV | + | 5-15% |
| 11 | 108172385 | p.R1730* | SNV | + | 5-15% |
| 11 | 108172421 | p.A1742P | SNV | + | 5-15% |

| Chromosome | Position | Sanger Detection* | CHPv2 Detection | TSACP Detection | TSTP Detection |
|---|---|---|---|---|---|
| 10 | 89717762 | Detected | Detected | Detected | Detected |
| 10 | 89717769 | Detected | Detected | Detected | Detected |
| 10 | 89720728 | Detected | Detected | Detected | Not Covered |
| 10 | 89720744 | Detected | Detected | Detected | Not Covered |
| 10 | 89720798 | Detected | Detected | Detected | Not Covered |
| 10 | 89720874 | Detected | Detected | Detected | Not Covered |
| 10 | 89720907 | Not Covered | Not Covered | Detected | Not Covered |
| 10 | 89725042 | Detected | Not Covered | Not Covered | Detected |
| 10 | 89725056 | Detected | Not Covered | Not Covered | Detected |
| 10 | 89725072 | Detected | Not Covered | Not Covered | Detected |
| 10 | 89725108 | Detected | Not Covered | Not Covered | Detected |
| 10 | 123258034 | Detected | Detected | Detected | Not Covered |
| 10 | 123274774 | Detected | Detected | Detected | Not Covered |
| 10 | 123274794 | Detected | Detected | Detected | Not Covered |
| 10 | 123274810 | Detected | Detected | Detected | Not Covered |
| 10 | 123279503 | Detected | Detected | Detected | Detected |
| 10 | 123279519 | Detected | Detected | Detected | Detected |
| 10 | 123279677 | Detected | Detected | Detected | Detected |
| 11 | 533874 | Detected | Detected | Detected | Not Covered |
| 11 | 533881 | Detected | Detected | Detected | Not Covered |
| 11 | 534242 | Not Covered | Detected | Not Covered | Not Covered |
| 11 | 534288 | Detected | Detected | Detected | Not Covered |
| 11 | 108117798 | Detected | Detected | Not Covered | Not Covered |
| 11 | 108119823 | Detected | Detected | Detected | Not Covered |
| 11 | 108123551 | Detected | Detected | Detected | Not Covered |
| 11 | 108123641 | Detected | Not Covered | Detected | Not Covered |
| 11 | 108138003 | Detected | Detected | Detected | Not Covered |
| 11 | 108155132 | Detected | Detected | Not Detected | Not Covered |
| 11 | 108170479 | Detected | Detected | Detected | Not Covered |
| 11 | 108170587 | Detected | Not Covered | Detected | Not Covered |
| 11 | 108172374 | Detected | Detected | Not Covered | Not Covered |
| 11 | 108172385 | Detected | Detected | Not Covered | Not Covered |
| 11 | 108172421 | Detected | Detected | Detected | Not Covered |

TABLE 9-continued

| Chromosome | Position | Reference |
|---|---|---|
| 11 | 108173640 | C |
| 11 | 108173736 | T |
| 11 | 108180945 | G |
| 11 | 108200958 | A |
| 11 | 108204681 | A |
| 11 | 108205769 | G |
| 11 | 108205780 | C |
| 11 | 108206594 | A |
| 11 | 108218045 | A |
| 11 | 108218089 | C |
| 11 | 108218196 | T |
| 11 | 108225590 | A |
| 11 | 108225661 | A |
| 11 | 108236087 | G |
| 11 | 108236118 | A |
| 11 | 108236203 | C |
| 12 | 25362805 | C |
| 12 | 25378647 | T |
| 12 | 25380275 | T |
| 12 | 25380283 | C |
| 12 | 25398207 | C |
| 12 | 25398215 | G |
| 12 | 25398284 | C |
| 12 | 25398295 | T |
| 12 | 112888165 | G |
| 12 | 112888189 | G |
| 12 | 112888199 | C |
| 12 | 112888210 | G |
| 12 | 112926852 | C |
| 12 | 112926888 | G |
| 12 | 112926899 | A |
| 12 | 112926908 | C |
| 12 | 121431413 | G |

| Chromosome | Position | Alternate |
|---|---|---|
| 11 | 108173640 | T |
| 11 | 108173736 | G |
| 11 | 108180945 | C |
| 11 | 108200958 | C |
| 11 | 108204681 | G |

TABLE 9-continued

| | | | |
|---|---|---|---|
| 11 | 108205769 | | C |
| 11 | 108205780 | | A |
| 11 | 108206594 | | T |
| 11 | 108218045 | | G |
| 11 | 108218089 | | G |
| 11 | 108218196 | | C |
| 11 | 108225590 | | T |
| 11 | 108225661 | | G |
| 11 | 108236087 | | A |
| 11 | 108236118 | | G |
| 11 | 108236203 | | T |
| 12 | 25362805 | | T |
| 12 | 25378647 | | G |
| 12 | 25380275 | | G |
| 12 | 25380283 | | T |
| 12 | 25398207 | | A |
| 12 | 25398215 | | A |
| 12 | 25398284 | | T |
| 12 | 25398295 | | C |
| 12 | 112888165 | | T |
| 12 | 112888189 | | A |
| 12 | 112888199 | | T |
| 12 | 112888210 | | A |
| 12 | 112926852 | | T |
| 12 | 112926888 | | C |
| 12 | 112926899 | | G |
| 12 | 112926908 | | A |
| 12 | 121431413 | | T |

| Chromosome | Position | Length | Mutation ID | Gene |
|---|---|---|---|---|
| 11 | 108173640 | 1 | COSM12792 | ATM |
| 11 | 108173736 | 1 | COSM1183962 | ATM |
| 11 | 108180945 | 1 | COSM21922 | ATM |
| 11 | 108200958 | 1 | COSM12951 | ATM |
| 11 | 108204681 | 1 | COSM12791 | ATM |
| 11 | 108205769 | 1 | COSM21636 | ATM |
| 11 | 108205780 | 1 | COSM1235404 | ATM |
| 11 | 108206594 | 1 | COSM22481 | ATM |
| 11 | 108218045 | 1 | COSM1183939 | ATM |
| 11 | 108218089 | 1 | COSM22485 | ATM |
| 11 | 108218196 | 1 | gDNA21 | ATM |

TABLE 9-continued

| Chromosome | Position | | | |
|---|---|---|---|---|
| 11 | 108225590 | 1 | COSM21930 | ATM |
| 11 | 108225661 | 1 | gDNA22 | ATM |
| 11 | 108236087 | 1 | COSM21626 | ATM |
| 11 | 108236118 | 1 | COSM1351060 | ATM |
| 11 | 108236203 | 1 | COSM21624 | ATM |
| 12 | 25362805 | 1 | COSM41307 | KRAS |
| 12 | 25378647 | 1 | COSM19940 | KRAS |
| 12 | 25380275 | 1 | COSM554 | KRAS |
| 12 | 25380283 | 1 | COSM546 | KRAS |
| 12 | 25398207 | 1 | AMXsynt11 | KRAS |
| 12 | 25398215 | 1 | COSM14208 | KRAS |
| 12 | 25398284 | 1 | COSM521 | KRAS |
| 12 | 25398295 | 1 | COSM507 | KRAS |
| 12 | 112888165 | 1 | COSM13011 | PTPN11 |
| 12 | 112888189 | 1 | COSM13013 | PTPN11 |
| 12 | 112888199 | 1 | COSM13015 | PTPN11 |
| 12 | 112888210 | 1 | COSM13000 | PTPN11 |
| 12 | 112926852 | 1 | COSM13034 | PTPN11 |
| 12 | 112926888 | 1 | COSM13027 | PTPN11 |
| 12 | 112926899 | 1 | COSM1358900 | PTPN11 |
| 12 | 112926908 | 1 | COSM13031 | PTPN11 |
| 12 | 121431413 | 1 | COSM21471 | HNF1A |

| Chromosome | Position | Mutation CDS |
|---|---|---|
| 11 | 108173640 | c.5380C > T |
| 11 | 108173736 | c.5476T > G |
| 11 | 108180945 | c.5821G > C |
| 11 | 108200958 | c.7325A > C |
| 11 | 108204681 | c.7996A > G |
| 11 | 108205769 | c.8084G > C |
| 11 | 108205780 | c.8095C > A |
| 11 | 108206594 | c.8174A > T |
| 11 | 108218045 | c.8624A > G |
| 11 | 108218089 | c.8668C > G |
| 11 | 108218196 | c.8671 + 104T > C |
| 11 | 108225590 | c.8839A > T |
| 11 | 108225661 | c.8850 + 60A > G |
| 11 | 108236087 | c.9023G > A |
| 11 | 108236118 | c.9054A > G |
| 11 | 108236203 | c.9139C > T |
| 12 | 25362805 | c.491G > A |

TABLE 9-continued

| | | | |
|---|---|---|---|
| 12 | 25378647 | c.351A > C | |
| 12 | 25380275 | c.183A > C | |
| 12 | 25380283 | c.175G > A | |
| 12 | 25398207 | c.111 + 1C > T | |
| 12 | 25398215 | c.104C > T | |
| 12 | 25398284 | c.35G > A | |
| 12 | 25398295 | c.24A > G | |
| 12 | 112888165 | c.181G > T | |
| 12 | 112888189 | c.205G > A | |
| 12 | 112888199 | c.215C > T | |
| 12 | 112888210 | c.226G > A | |
| 12 | 112926852 | c.1472C > T | |
| 12 | 112926888 | c.1508G > C | |
| 12 | 112926899 | c.1519A > G | |
| 12 | 112926908 | c.1528C > A | |
| 12 | 121431413 | c.617G > T | |

| Chromosome | Position | Mutation AA | Mutation Type | Strand | Target Frequency |
|---|---|---|---|---|---|
| 11 | 108173640 | p.L1794L | SNV | + | 5-15% |
| 11 | 108173736 | p.L1826V | SNV | + | 5-15% |
| 11 | 108180945 | p.V1941L | SNV | + | 5-15% |
| 11 | 108200958 | p.Q2442P | SNV | + | 5-15% |
| 11 | 108204681 | p.T2666A | SNV | + | 5-15% |
| 11 | 108205769 | p.G2695A | SNV | + | 5-15% |
| 11 | 108205780 | p.P2699T | SNV | + | 5-15% |
| 11 | 108206594 | p.D2725V | SNV | + | 5-15% |
| 11 | 108218045 | p.N2875S | SNV | + | 5-15% |
| 11 | 108218089 | p.L2890V | SNV | + | 5-15% |
| 11 | 108218196 | p.(=) | SNV | + | genomic |
| 11 | 108225590 | p.T2947S | SNV | + | 5-15% |
| 11 | 108225661 | p.(=) | SNV | + | genomic |
| 11 | 108236087 | p.R3008H | SNV | + | 5-15% |
| 11 | 108236118 | p.K3018K | SNV | + | 5-15% |
| 11 | 108236203 | p.R3047* | SNV | + | 5-15% |
| 12 | 25362805 | p.R164Q | SNV | − | 5-15% |
| 12 | 25378647 | p.K117N | SNV | − | 5-15% |
| 12 | 25380275 | p.Q61H | SNV | − | 5-15% |
| 12 | 25380283 | p.A59T | SNV | − | 5-15% |
| 12 | 25398207 | p.? | SNV | − | 5-15% |
| 12 | 25398215 | p.T35I | SNV | − | 5-15% |
| 12 | 25398284 | p.G12D | SNV | − | 5-15% |

TABLE 9-continued

| Chromosome | Position | | | | |
|---|---|---|---|---|---|
| 12 | 25398295 | p.V8V | SNV | - | 5-15% |
| 12 | 112888165 | p.D61Y | SNV | + | 5-15% |
| 12 | 112888189 | p.E69K | SNV | + | 5-15% |
| 12 | 112888199 | p.A72V | SNV | + | 5-15% |
| 12 | 112888210 | p.E76K | SNV | + | 5-15% |
| 12 | 112926852 | p.P491L | SNV | + | 5-15% |
| 12 | 112926888 | p.G503A | SNV | + | 5-15% |
| 12 | 112926899 | p.T507A | SNV | + | 5-15% |
| 12 | 112926908 | p.Q510K | SNV | + | 5-15% |
| 12 | 121431413 | p.W206L | SNV | + | 5-15% |

| Chromosome | Position | Sanger Detection* | CHPv2 Detection | TSACP Detection | TSTP Detection |
|---|---|---|---|---|---|
| 11 | 108173640 | Detected | Detected | Detected | Not Covered |
| 11 | 108173736 | Detected | Not Covered | Detected | Not Covered |
| 11 | 108180945 | Detected | Detected | Detected | Not Covered |
| 11 | 108200958 | Detected | Detected | Detected | Not Covered |
| 11 | 108204681 | Detected | Detected | Detected | Not Covered |
| 11 | 108205769 | Detected | Detected | Detected | Not Covered |
| 11 | 108205780 | Detected | Detected | Detected | Not Covered |
| 11 | 108206594 | Detected | Detected | Detected | Not Covered |
| 11 | 108218045 | Detected | Detected | Not Covered | Not Covered |
| 11 | 108218089 | Detected | Detected | Detected | Not Covered |
| 11 | 108218196 | Not Covered | Not Covered | Detected | Not Covered |
| 11 | 108225590 | Detected | Detected | Detected | Not Covered |
| 11 | 108225661 | Not Covered | Not Covered | Detected | Not Covered |
| 11 | 108236087 | Detected | Detected | Detected | Not Covered |
| 11 | 108236118 | Detected | Detected | Detected | Not Covered |
| 11 | 108236203 | Detected | Detected | Detected | Not Covered |
| 12 | 25362805 | Detected | Not Covered | Not Covered | Detected |
| 12 | 25378647 | Detected | Detected | Detected | Detected |
| 12 | 25380275 | Detected | Detected | Detected | Detected |
| 12 | 25380283 | Detected | Detected | Detected | Detected |
| 12 | 25398207 | Detected | Detected | Not Covered | Detected |
| 12 | 25398215 | Detected | Detected | Not Covered | Detected |
| 12 | 25398284 | Detected | Detected | Detected | Detected |
| 12 | 25398295 | Detected | Detected | Detected | Detected |
| 12 | 112888165 | Detected | Detected | Detected | Not Covered |
| 12 | 112888189 | Detected | Detected | Detected | Not Covered |
| 12 | 112888199 | Detected | Detected | Detected | Not Covered |
| 12 | 112888210 | Detected | Detected | Detected | Not Covered |

TABLE 9-continued

| | | | | | |
|---|---|---|---|---|---|
| 12 | 112926852 | Detected | Detected | Not Covered | Not Covered |
| 12 | 112926888 | Detected | Detected | Detected | Not Covered |
| 12 | 112926899 | Detected | Detected | Detected | Not Covered |
| 12 | 112926908 | Detected | Detected | Detected | Not Covered |
| 12 | 121431413 | Detected | Detected | Detected | Not Covered |

| Chromosome | Position | Reference |
|---|---|---|
| 12 | 121431428 | A |
| 12 | 121431481 | C |
| 12 | 121431506 | A |
| 12 | 121432032 | C |
| 12 | 121432040 | C |
| 12 | 121432117 | G |
| 12 | 121432117 | G |
| 13 | 28592629 | T |
| 13 | 28592642 | C |
| 13 | 28592653 | C |
| 13 | 28602329 | G |
| 13 | 28608255 | G |
| 13 | 28608281 | A |
| 13 | 28610138 | G |
| 13 | 28610183 | A |
| 13 | 48919244 | G |
| 13 | 48923148 | T |
| 13 | 48941628 | A |
| 13 | 48941648 | C |
| 13 | 48941658 | A |
| 13 | 48941672 | A |
| 13 | 48942685 | C |
| 13 | 48953760 | C |
| 13 | 48955538 | C |
| 13 | 48955550 | C |
| 13 | 48955571 | T |
| 13 | 49027168 | C |
| 13 | 49027249 | T |
| 13 | 49033890 | TAGAACATATCATC (SEQ ID NO: 29) |
| 13 | 49033916 | C |
| 13 | 49033926 | T |
| 13 | 49037865 | A |
| 13 | 49037877 | G |

TABLE 9-continued

| Chromosome | Position | Alternate |
|---|---|---|
| 12 | 121431428 | C |
| 12 | 121431481 | T |
| 12 | 121431506 | G |
| 12 | 121432032 | T |
| 12 | 121432040 | T |
| 12 | 121432117 | GC |
| 12 | 121432117 | C |
| 13 | 28592629 | C |
| 13 | 28592642 | A |
| 13 | 28592653 | T |
| 13 | 28602329 | A |
| 13 | 28608255 | GATCATATTCATATTCTCTGAA (SEQ ID NO: 30) |
| 13 | 28608281 | G |
| 13 | 28610138 | A |
| 13 | 28610183 | G |
| 13 | 48919244 | T |
| 13 | 48923148 | A |
| 13 | 48941628 | T |
| 13 | 48941648 | T |
| 13 | 48941658 | G |
| 13 | 48941672 | G |
| 13 | 48942685 | T |
| 13 | 48953760 | T |
| 13 | 48955538 | T |
| 13 | 48955550 | T |
| 13 | 48955571 | C |
| 13 | 49027168 | T |
| 13 | 49027249 | C |
| 13 | 49033890 | T |
| 13 | 49033916 | T |
| 13 | 49033926 | C |
| 13 | 49037865 | G |
| 13 | 49037877 | T |

| Chromosome | Position | Length | Mutation ID | Gene |
|---|---|---|---|---|
| 12 | 121431428 | 1 | COSM24900 | HNF1A |
| 12 | 121431481 | 1 | COSM24832 | HNF1A |
| 12 | 121431506 | 1 | COSM21474 | HNF1A |
| 12 | 121432032 | 1 | COSM24923 | HNF1A |
| 12 | 121432040 | 1 | COSM24692 | HNF1A |

TABLE 9-continued

| Chromosome | Position | | | |
|---|---|---|---|---|
| 12 | 121432117 | 1 | COSM21481 | HNF1A |
| 12 | 121432117 | 1 | gDNA23 | HNF1A |
| 13 | 28592629 | 1 | COSM1166729 | FLT3 |
| 13 | 28592642 | 1 | COSM783 | FLT3 |
| 13 | 28592653 | 1 | COSM25248 | FLT3 |
| 13 | 28602329 | 1 | COSM786 | FLT3 |
| 13 | 28608255 | 21 | COSM27907 | FLT3 |
| 13 | 28608281 | 1 | COSM19522 | FLT3 |
| 13 | 28610138 | 1 | COSM28042 | FLT3 |
| 13 | 28610183 | 1 | gDNA24 | FLT3 |
| 13 | 48919244 | 1 | COSM890 | RB1 |
| 13 | 48923148 | 1 | COSM915 | RB1 |
| 13 | 48941628 | 1 | COSM28816 | RB1 |
| 13 | 48941648 | 1 | COSM891 | RB1 |
| 13 | 48941658 | 1 | COSM1367204 | RB1 |
| 13 | 48941672 | 1 | COSM1367206 | RB1 |
| 13 | 48942685 | 1 | COSM879 | RB1 |
| 13 | 48953760 | 1 | COSM895 | RB1 |
| 13 | 48955538 | 1 | COSM887 | RB1 |
| 13 | 48955550 | 1 | COSM888 | RB1 |
| 13 | 48955571 | 1 | COSM1367255 | RB1 |
| 13 | 49027168 | 1 | COSM892 | RB1 |
| 13 | 49027249 | 1 | COSM35483 | RB1 |
| 13 | 49033890 | 13 | COSM870 | RB1 |
| 13 | 49033916 | 1 | COSM13117 | RB1 |
| 13 | 49033926 | 1 | COSM942 | RB1 |
| 13 | 49037865 | 1 | COSM1042 | RB1 |
| 13 | 49037877 | 1 | COSM883 | RB1 |

| Chromosome | Position | Mutation CDS |
|---|---|---|
| 12 | 121431428 | c.632A > C |
| 12 | 121431481 | c.685C > T |
| 12 | 121431506 | c.710A > G |
| 12 | 121432032 | c.779C > T |
| 12 | 121432040 | c.787C > T |
| 12 | 121432117 | c.872_873insC |
| 12 | 121432117 | c.864G > C |
| 13 | 28592629 | c.2516A > G |
| 13 | 28592642 | c.2503G > T |
| 13 | 28592653 | c.2492G > A |
| 13 | 28602329 | c.2039C > T |

TABLE 9-continued

| | | |
|---|---|---|
| 13 | 28608255 | c.1800_1801insTTCAGAGAATATGAATATGAT (SEQ ID NO: 31) |
| 13 | 28608281 | c.1775T > C |
| 13 | 28610138 | c.1352C > T |
| 13 | 28610183 | c.1310 − 3T > C |
| 13 | 48919244 | c.409G > T |
| 13 | 48923148 | c.596T > A |
| 13 | 48941628 | c.940 − 2A > T |
| 13 | 48941648 | c.958C > T |
| 13 | 48941658 | c.968A > G |
| 13 | 48941672 | c.982A > G |
| 13 | 48942685 | c.1072C > T |
| 13 | 48953760 | c.1363C > T |
| 13 | 48955538 | c.1654C > T |
| 13 | 48955550 | c.1666C > T |
| 13 | 48955571 | c.1687T > C |
| 13 | 49027168 | c.1735C > T |
| 13 | 49027249 | c.1814 + 2T > C |
| 13 | 49033890 | c.2028_2040del13 |
| 13 | 49033916 | c.2053C > T |
| 13 | 49033926 | c.2063T > C |
| 13 | 49037865 | c.2107 − 2A > G |
| 13 | 49037877 | c.2117G > T |

| Chromosome | Position | Mutation AA | Mutation Type | Target Strand | Frequency | Sanger Detection* |
|---|---|---|---|---|---|---|
| 12 | 121431428 | p.Q211P | SNV | + | 5-15% | Detected |
| 12 | 121431481 | p.R229* | SNV | + | 5-15% | Detected |
| 12 | 121431506 | p.N237S | SNV | + | 5-15% | Detected |
| 12 | 121432032 | p.T260M | SNV | + | 5-15% | Detected |
| 12 | 121432040 | p.R263C | SNV | + | 5-15% | Detected |
| 12 | 121432117 | p.G292fs*25 | INS | + | 5-15% | Detected |
| 12 | 121432117 | p.G288G | SNV | + | genomic | Not Covered |
| 13 | 28592629 | p.D839G | SNV | − | 5-15% | Detected |
| 13 | 28592642 | p.D835Y | SNV | − | 5-15% | Detected |
| 13 | 28592653 | p.G831E | SNV | − | 5-15% | Detected |
| 13 | 28602329 | p.A680V | SNV | − | 5-15% | Detected |
| 13 | 28608255 | p.D600_L601insFREYEYD | INS | − | 5-15% | Detected |
| 13 | 28608281 | p.V592A | SNV | − | 5-15% | Detected |
| 13 | 28610138 | p.S451F | SNV | − | 5-15% | Detected |
| 13 | 28610183 | p.? | SNV | − | genomic | Not Covered |
| 13 | 48919244 | p.E137* | SNV | + | 5-15% | Detected |

TABLE 9-continued

| | | | | | | |
|---|---|---|---|---|---|---|
| 13 | 48923148 | p.L199* | SNV | + | 5-15% | Detected |
| 13 | 48941628 | p.? | SNV | + | 5-15% | Detected |
| 13 | 48941648 | p.R320* | SNV | + | 5-15% | Detected |
| 13 | 48941658 | p.E323G | SNV | + | 5-15% | Detected |
| 13 | 48941672 | p.N328D | SNV | + | 5-15% | Detected |
| 13 | 48942685 | p.R358* | SNV | + | 5-15% | Detected |
| 13 | 48953760 | p.R455* | SNV | + | 5-15% | Detected |
| 13 | 48955538 | p.R552* | SNV | + | 5-15% | Detected |
| 13 | 48955550 | p.R556* | SNV | + | 5-15% | Detected |
| 13 | 48955571 | p.W563R | SNV | + | 5-15% | Detected |
| 13 | 49027168 | p.R579* | SNV | + | 5-15% | Detected |
| 13 | 49027249 | p.? | SNV | + | 5-15% | Detected |
| 13 | 49033890 | p.L676fs*16 | DEL | + | 5-15% | Detected |
| 13 | 49033916 | p.Q685* | SNV | + | 5-15% | Detected |
| 13 | 49033926 | p.L688P | SNV | + | 5-15% | Detected |
| 13 | 49037865 | p.? | SNV | + | 5-15% | Detected |
| 13 | 49037877 | p.C706F | SNV | + | 5-15% | Detected |

| Chromosome | Position | CHPv2 Detection | TSACP Detection | TSTP Detection |
|---|---|---|---|---|
| 12 | 121431428 | Detected | Detected | Not Covered |
| 12 | 121431481 | Not Covered | Detected | Not Covered |
| 12 | 121431506 | Not Covered | Detected | Not Covered |
| 12 | 121432032 | Detected | Not Covered | Not Covered |
| 12 | 121432040 | Detected | Not Covered | Not Covered |
| 12 | 121432117 | Not Covered | Detected | Not Covered |
| 12 | 121432117 | Not Covered | Detected | Not Covered |
| 13 | 28592629 | Detected | Detected | Not Covered |
| 13 | 28592642 | Detected | Detected | Not Covered |
| 13 | 28592653 | Detected | Detected | Not Covered |
| 13 | 28602329 | Detected | Detected | Not Covered |
| 13 | 28608255 | Not Detected | Not Detected | Not Covered |
| 13 | 28608281 | Detected | Detected | Not Covered |
| 13 | 28610138 | Detected | Detected | Not Covered |
| 13 | 28610183 | Detected | Detected | Not Covered |
| 13 | 48919244 | Detected | Detected | Not Covered |
| 13 | 48923148 | Detected | Detected | Not Covered |
| 13 | 48941628 | Detected | Not Covered | Not Covered |
| 13 | 48941648 | Detected | Not Covered | Not Covered |
| 13 | 48941658 | Detected | Not Covered | Not Covered |
| 13 | 48941672 | Detected | Not Covered | Not Covered |
| 13 | 48942685 | Detected | Detected | Not Covered |

TABLE 9-continued

| | | | | |
|---|---|---|---|---|
| 13 | 48953760 | Detected | Not Covered | Not Covered |
| 13 | 48955538 | Detected | Detected | Not Covered |
| 13 | 48955550 | Detected | Detected | Not Covered |
| 13 | 48955571 | Detected | Detected | Not Covered |
| 13 | 49027168 | Detected | Detected | Not Covered |
| 13 | 49027249 | Not Covered | Detected | Not Covered |
| 13 | 49033890 | Detected | Detected | Not Covered |
| 13 | 49033916 | Detected | Detected | Not Covered |
| 13 | 49033926 | Detected | Detected | Not Covered |
| 13 | 49037865 | Detected | Detected | Not Covered |
| 13 | 49037877 | Detected | Detected | Not Covered |

| Chromosome | Position | Reference |
|---|---|---|
| 13 | 49037903 | A |
| 13 | 49037913 | A |
| 13 | 49039164 | G |
| 13 | 49039183 | T |
| 13 | 49039189 | A |
| 13 | 49039215 | A |
| 14 | 105246551 | C |
| 15 | 66727455 | G |
| 15 | 66727483 | G |
| 15 | 90631838 | C |
| 15 | 90631879 | T |
| 15 | 90631934 | C |
| 16 | 68835650 | GGTGTGATTACAGTCAAAAGGCCTCTACGGT (SEQ ID NO: 32) |
| 16 | 68846087 | A |
| 16 | 68846137 | G |
| 16 | 68847282 | G |
| 16 | 68855924 | A |
| 16 | 68855934 | T |
| 16 | 68855966 | G |
| 16 | 68856041 | G |
| 16 | 68856093 | C |
| 16 | 68856105 | G |
| 17 | 7572962 | GT |
| 17 | 7572986 | G |
| 17 | 7573010 | T |
| 17 | 7574003 | G |
| 17 | 7574012 | C |
| 17 | 7574018 | G |

TABLE 9-continued

| | | |
|---|---|---|
| 17 | 7574026 | C |
| 17 | 7576855 | G |
| 17 | 7576865 | A |
| 17 | 7576883 | T |
| 17 | 7576897 | G |

| Chromosome | Position | Alternate |
|---|---|---|
| 13 | 49037903 | T |
| 13 | 49037913 | G |
| 13 | 49039164 | T |
| 13 | 49039183 | G |
| 13 | 49039189 | G |
| 13 | 49039215 | T |
| 14 | 105246551 | T |
| 15 | 66727455 | T |
| 15 | 66727483 | A |
| 15 | 90631838 | T |
| 15 | 90631879 | C |
| 15 | 90631934 | T |
| 16 | 68835650 | G |
| 16 | 68846087 | G |
| 16 | 68846137 | C |
| 16 | 68847282 | A |
| 16 | 68855924 | AC |
| 16 | 68855934 | C |
| 16 | 68855966 | A |
| 16 | 68856041 | A |
| 16 | 68856093 | T |
| 16 | 68856105 | A |
| 17 | 7572962 | G |
| 17 | 7572986 | A |
| 17 | 7573010 | C |
| 17 | 7574003 | A |
| 17 | 7574012 | A |
| 17 | 7574018 | A |
| 17 | 7574026 | A |
| 17 | 7576855 | A |
| 17 | 7576865 | C |
| 17 | 7576883 | C |
| 17 | 7576897 | A |

TABLE 9-continued

| Chromosome | Position | Length | Mutation ID | Gene |
|---|---|---|---|---|
| 13 | 49037903 | 1 | COSM940 | RB1 |
| 13 | 49037913 | 1 | COSM1367309 | RB1 |
| 13 | 49039164 | 1 | COSM868 | RB1 |
| 13 | 49039183 | 1 | COSM916 | RB1 |
| 13 | 49039189 | 1 | COSM551465 | RB1 |
| 13 | 49039215 | 1 | COSM254910 | RB1 |
| 14 | 105246551 | 1 | COSM33765 | AKT1 |
| 15 | 66727455 | 1 | COSM1235478 | MAP2K1 |
| 15 | 66727483 | 1 | COSM1235479 | MAP2K1 |
| 15 | 90631838 | 1 | COSM33733 | IDH2 |
| 15 | 90631879 | 1 | COSM1375400 | IDH2 |
| 15 | 90631934 | 1 | COSM41590 | IDH2 |
| 16 | 68835650 | 30 | AMXsynt10 | CDH1 |
| 16 | 68846087 | 1 | COSM1379165 | CDH1 |
| 16 | 68846137 | 1 | COSM19748 | CDH1 |
| 16 | 68847282 | 1 | COSM19750 | CDH1 |
| 16 | 68855924 | 1 | COSM25267 | CDH1 |
| 16 | 68855934 | 1 | COSM19746 | CDH1 |
| 16 | 68855966 | 1 | COSM19758 | CDH1 |
| 16 | 68856041 | 1 | COSM19743 | CDH1 |
| 16 | 68856093 | 1 | COSM19822 | CDH1 |
| 16 | 68856105 | 1 | COSM19418 | CDH1 |
| 17 | 7572962 | 1 | COSM13747 | TP53 |
| 17 | 7572986 | 1 | COSM307348 | TP53 |
| 17 | 7573010 | 1 | COSM1191161 | TP53 |
| 17 | 7574003 | 1 | COSM11073 | TP53 |
| 17 | 7574012 | 1 | COSM11286 | TP53 |
| 17 | 7574018 | 1 | COSM11071 | TP53 |
| 17 | 7574026 | 1 | COSM11514 | TP53 |
| 17 | 7576855 | 1 | COSM11354 | TP53 |
| 17 | 7576865 | 1 | COSM44823 | TP53 |
| 17 | 7576883 | 1 | COSM46088 | TP53 |
| 17 | 7576897 | 1 | COSM10786 | TP53 |

| Chromosome | Position | Mutation CDS |
|---|---|---|
| 13 | 49037903 | c.2143A > T |
| 13 | 49037913 | c.2153A > G |
| 13 | 49039164 | c.2242G > T |
| 13 | 49039183 | c.2261T > G |
| 13 | 49039189 | c.2267A > G |

TABLE 9-continued

| | | |
|---|---|---|
| 13 | 49039215 | c.2293A > T |
| 14 | 105246551 | c.49G > A |
| 15 | 66727455 | c.171G > T |
| 15 | 66727483 | c.199G > A |
| 15 | 90631838 | c.515G > A |
| 15 | 90631879 | c.474A > G |
| 15 | 90631934 | c.419G > A |
| 16 | 68835650 | c.241del30 |
| 16 | 68846087 | c.1058A > G |
| 16 | 68846137 | c.1108G > C |
| 16 | 68847282 | c.1204G > A |
| 16 | 68855924 | c.1733_1734insC |
| 16 | 68855934 | c.1742T > C |
| 16 | 68855966 | c.1774G > A |
| 16 | 68856041 | c.1849G > A |
| 16 | 68856093 | c.1901C > T |
| 16 | 68856105 | c.1913G > A |
| 17 | 7572962 | c.1146delA |
| 17 | 7572986 | c.1123C > T |
| 17 | 7573010 | c.1101 − 2A > G |
| 17 | 7574003 | c.1024C > T |
| 17 | 7574012 | c.1015G > T |
| 17 | 7574018 | c.1009C > T |
| 17 | 7574026 | c.1001G > T |
| 17 | 7576855 | c.991C > T |
| 17 | 7576865 | c.981T > G |
| 17 | 7576883 | c.963A > G |
| 17 | 7576897 | c.949C > T |

| Chromosome | Position | Mutation AA | Mutation Type | Strand | Target Frequency | Sanger Detection* |
|---|---|---|---|---|---|---|
| 13 | 49037903 | p.K715* | SNV | + | 5-15% | Detected |
| 13 | 49037913 | p.D718G | SNV | + | 5-15% | Detected |
| 13 | 49039164 | p.E748* | SNV | + | 5-15% | Detected |
| 13 | 49039183 | p.V754G | SNV | + | 5-15% | Detected |
| 13 | 49039189 | p.Y756C | SNV | + | 5-15% | Detected |
| 13 | 49039215 | p.K765* | SNV | + | 5-15% | Detected |
| 14 | 105246551 | p.E17K | SNV | − | 5-15% | Detected |
| 15 | 66727455 | p.K57N | SNV | + | 5-15% | Detected |
| 15 | 66727483 | p.D67N | SNV | + | 5-15% | Detected |
| 15 | 90631838 | p.R172K | SNV | − | 5-15% | Detected |
| 15 | 90631879 | p.P158P | SNV | − | 5-15% | Detected |

TABLE 9-continued

| | | | | | | |
|---|---|---|---|---|---|---|
| 15 | 90631934 | p.R140Q | SNV | − | 5-15% | Detected |
| 16 | 68835650 | p.G81_F91del | DEL | + | 5-15% | Detected |
| 16 | 68846087 | p.E353G | SNV | + | 5-15% | Detected |
| 16 | 68846137 | p.D370H | SNV | + | 5-15% | Detected |
| 16 | 68847282 | p.D402N | SNV | + | 5-15% | Detected |
| 16 | 68855924 | p.G579fs*9 | INS | + | 5-15% | Detected |
| 16 | 68855934 | p.L581P | SNV | + | 5-15% | Detected |
| 16 | 68855966 | p.A592T | SNV | + | 5-15% | Detected |
| 16 | 68856041 | p.A617T | SNV | + | 5-15% | Detected |
| 16 | 68856093 | p.A634V | SNV | + | 5-15% | Detected |
| 16 | 68856105 | p.W638* | SNV | + | 5-15% | Detected |
| 17 | 7572962 | p.K382fs* > 12 | DEL | − | 5-15% | Detected |
| 17 | 7572986 | p.Q375* | SNV | − | 5-15% | Detected |
| 17 | 7573010 | p.? | SNV | − | 5-15% | Detected |
| 17 | 7574003 | p.R342* | SNV | − | 5-15% | Detected |
| 17 | 7574012 | p.E339* | SNV | − | 5-15% | Detected |
| 17 | 7574018 | p.R337C | SNV | − | 5-15% | Detected |
| 17 | 7574026 | p.G334V | SNV | − | 5-15% | Detected |
| 17 | 7576855 | p.Q331* | SNV | − | 5-15% | Detected |
| 17 | 7576865 | p.Y327* | SNV | − | 5-15% | Detected |
| 17 | 7576883 | p.K321K | SNV | − | 5-15% | Detected |
| 17 | 7576897 | p.Q317* | SNV | − | 5-15% | Detected |

| Chromosome | Position | CHPv2 Detection | TSACP Detection | TSTP Detection |
|---|---|---|---|---|
| 13 | 49037903 | Detected | Detected | Not Covered |
| 13 | 49037913 | Detected | Detected | Not Covered |
| 13 | 49039164 | Detected | Detected | Not Covered |
| 13 | 49039183 | Detected | Detected | Not Covered |
| 13 | 49039189 | Detected | Detected | Not Covered |
| 13 | 49039215 | Detected | Detected | Not Covered |
| 14 | 105246551 | Detected | Detected | Detected |
| 15 | 66727455 | Not Covered | Not Covered | Detected |
| 15 | 66727483 | Not Covered | Not Covered | Detected |
| 15 | 90631838 | Detected | Not Covered | Not Covered |
| 15 | 90631879 | Detected | Not Covered | Not Covered |
| 15 | 90631934 | Detected | Not Covered | Not Covered |
| 16 | 68835650 | Not Detected | Not Detected | Not Covered |
| 16 | 68846087 | Detected | Not Covered | Detected |
| 16 | 68846137 | Detected | Detected | Detected |
| 16 | 68847282 | Detected | Detected | Detected |

TABLE 9-continued

| | | | | |
|---|---|---|---|---|
| 16 | 68855924 | Not Covered | Not Covered | Detected |
| 16 | 68855934 | Not Covered | Not Covered | Detected |
| 16 | 68855966 | Not Covered | Not Covered | Detected |
| 16 | 68856041 | Not Covered | Not Covered | Detected |
| 16 | 68856093 | Not Covered | Not Covered | Detected |
| 16 | 68856105 | Not Covered | Not Covered | Detected |
| 17 | 7572962 | Not Covered | Not Covered | Detected |
| 17 | 7572986 | Not Covered | Not Covered | Detected |
| 17 | 7573010 | Not Covered | Not Covered | Detected |
| 17 | 7574003 | Detected | Detected | Detected |
| 17 | 7574012 | Detected | Detected | Detected |
| 17 | 7574018 | Detected | Detected | Detected |
| 17 | 7574026 | Detected | Detected | Detected |
| 17 | 7576855 | Not Covered | Not Covered | Detected |
| 17 | 7576865 | Not Covered | Not Covered | Detected |
| 17 | 7576883 | Not Covered | Not Covered | Detected |
| 17 | 7576897 | Not Covered | Not Covered | Detected |

| Chromosome | Position | Reference |
|---|---|---|
| 17 | 7577022 | G |
| 17 | 7577046 | C |
| 17 | 7577105 | G |
| 17 | 7577120 | C |
| 17 | 7577538 | C |
| 17 | 7577548 | C |
| 17 | 7577559 | G |
| 17 | 7577580 | T |
| 17 | 7578115 | T |
| 17 | 7578190 | T |
| 17 | 7578196 | A |
| 17 | 7578203 | C |
| 17 | 7578235 | T |
| 17 | 7578388 | C |
| 17 | 7578442 | T |
| 17 | 7578449 | C |
| 17 | 7578461 | C |
| 17 | 7578526 | C |
| 17 | 7578535 | T |
| 17 | 7578542 | G |
| 17 | 7578550 | G |
| 17 | 7579295 | C |

TABLE 9-continued

| | | |
|---|---|---|
| 17 | 7579312 | C |
| 17 | 7579358 | C |
| 17 | 7579368 | A |
| 17 | 7579414 | C |
| 17 | 7579442 | G |
| 17 | 7579472 | G |
| 17 | 7579521 | C |
| 17 | 7579536 | C |
| 17 | 7579553 | A |
| 17 | 7579575 | G |
| 17 | 7579715 | AG |

| Chromosome | Position | Alternate |
|---|---|---|
| 17 | 7577022 | A |
| 17 | 7577046 | A |
| 17 | 7577105 | A |
| 17 | 7577120 | T |
| 17 | 7577538 | T |
| 17 | 7577548 | T |
| 17 | 7577559 | A |
| 17 | 7577580 | C |
| 17 | 7578115 | C |
| 17 | 7578190 | C |
| 17 | 7578196 | T |
| 17 | 7578203 | T |
| 17 | 7578235 | C |
| 17 | 7578388 | T |
| 17 | 7578442 | C |
| 17 | 7578449 | T |
| 17 | 7578461 | A |
| 17 | 7578526 | T |
| 17 | 7578535 | C |
| 17 | 7578542 | C |
| 17 | 7578550 | A |
| 17 | 7579295 | T |
| 17 | 7579312 | T |
| 17 | 7579358 | A |
| 17 | 7579368 | C |
| 17 | 7579414 | T |
| 17 | 7579442 | A |
| 17 | 7579472 | C |

TABLE 9-continued

| | 17 | | 7579521 | | A | |
| | 17 | | 7579536 | | A | |
| | 17 | | 7579553 | | G | |
| | 17 | | 7579575 | | A | |
| | 17 | | 7579715 | | A | |

| Chromosome | Position | Length | Mutation ID | Gene |
|---|---|---|---|---|
| 17 | 7577022 | 1 | COSM10663 | TP53 |
| 17 | 7577046 | 1 | COSM10710 | TP53 |
| 17 | 7577105 | 1 | COSM10863 | TP53 |
| 17 | 7577120 | 1 | COSM10660 | TP53 |
| 17 | 7577538 | 1 | COSM10662 | TP53 |
| 17 | 7577548 | 1 | COSM6932 | TP53 |
| 17 | 7577559 | 1 | COSM10812 | TP53 |
| 17 | 7577580 | 1 | COSM10725 | TP53 |
| 17 | 7578115 | 1 | gDNA25 | TP53 |
| 17 | 7578190 | 1 | COSM10758 | TP53 |
| 17 | 7578196 | 1 | COSM44317 | TP53 |
| 17 | 7578203 | 1 | COSM10667 | TP53 |
| 17 | 7578235 | 1 | COSM43947 | TP53 |
| 17 | 7578388 | 1 | COSM10738 | TP53 |
| 17 | 7578442 | 1 | COSM10808 | TP53 |
| 17 | 7578449 | 1 | COSM10739 | TP53 |
| 17 | 7578461 | 1 | COSM10670 | TP53 |
| 17 | 7578526 | 1 | COSM10801 | TP53 |
| 17 | 7578535 | 1 | COSM11582 | TP53 |
| 17 | 7578542 | 1 | COSM11462 | TP53 |
| 17 | 7578550 | 1 | COSM44226 | TP53 |
| 17 | 7579295 | 1 | COSM44985 | TP53 |
| 17 | 7579312 | 1 | COSM43904 | TP53 |
| 17 | 7579358 | 1 | COSM10716 | TP53 |
| 17 | 7579368 | 1 | COSM46103 | TP53 |
| 17 | 7579414 | 1 | COSM44492 | TP53 |
| 17 | 7579442 | 1 | COSM43910 | TP53 |
| 17 | 7579472 | 1 | gDNA26, COSM250061 | TP53 |
| 17 | 7579521 | 1 | COSM12168 | TP53 |
| 17 | 7579536 | 1 | COSM44907 | TP53 |
| 17 | 7579553 | 1 | COSM43664 | TP53 |
| 17 | 7579575 | 1 | COSM46286 | TP53 |
| 17 | 7579715 | 1 | COSM85573 | TP53 |

TABLE 9-continued

| Chromosome | Position | Mutation CDS |
|---|---|---|
| 17 | 7577022 | c.916C > T |
| 17 | 7577046 | c.892G > T |
| 17 | 7577105 | c.833C > T |
| 17 | 7577120 | c.818G > A |
| 17 | 7577538 | c.743G > A |
| 17 | 7577548 | c.733G > A |
| 17 | 7577559 | c.722C > T |
| 17 | 7577580 | c.701A > G |
| 17 | 7578115 | c.672 + 62A > G |
| 17 | 7578190 | c.659A > G |
| 17 | 7578196 | c.653T > A |
| 17 | 7578203 | c.646G > A |
| 17 | 7578235 | c.614A > G |
| 17 | 7578388 | c.542G > A |
| 17 | 7578442 | c.488A > G |
| 17 | 7578449 | c.481G > A |
| 17 | 7578461 | c.469G > T |
| 17 | 7578526 | c.404G > A |
| 17 | 7578535 | c.395A > G |
| 17 | 7578542 | c.388C > G |
| 17 | 7578550 | c.380C > T |
| 17 | 7579295 | c.375 + 17G > A |
| 17 | 7579312 | c.375G > A |
| 17 | 7579358 | c.329G > T |
| 17 | 7579368 | c.319T > G |
| 17 | 7579414 | c.273G > A |
| 17 | 7579442 | c.245C > T |
| 17 | 7579472 | c.215G > C |
| 17 | 7579521 | c.166G > T |
| 17 | 7579536 | c.151G > T |
| 17 | 7579553 | c.134T > C |
| 17 | 7579575 | c.112C > T |
| 17 | 7579715 | c.80delC |

| Chromosome | Position | Mutation AA | Mutation Type | Strand | Target Frequency | Sanger Detection* |
|---|---|---|---|---|---|---|
| 17 | 7577022 | p.R306* | SNV | − | 5-15% | Detected |
| 17 | 7577046 | p.E298* | SNV | − | 5-15% | Detected |
| 17 | 7577105 | p.P278L | SNV | − | 5-15% | Detected |
| 17 | 7577120 | p.R273H | SNV | − | 5-15% | Detected |
| 17 | 7577538 | p.R248Q | SNV | − | 5-15% | Detected |

TABLE 9-continued

| | | | | | | |
|---|---|---|---|---|---|---|
| 17 | 7577548 | p.G245S | SNV | − | 5-15% | Detected |
| 17 | 7577559 | p.S241F | SNV | − | 5-15% | Detected |
| 17 | 7577580 | p.Y234C | SNV | − | 5-15% | Detected |
| 17 | 7578115 | p.(=) | SNV | − | genomic | Not Covered |
| 17 | 7578190 | p.Y220C | SNV | − | 5-15% | Detected |
| 17 | 7578196 | p.V218E | SNV | − | 5-15% | Detected |
| 17 | 7578203 | p.V216M | SNV | − | 5-15% | Detected |
| 17 | 7578235 | p.Y205C | SNV | − | 5-15% | Detected |
| 17 | 7578388 | p.R181H | SNV | − | 5-15% | Detected |
| 17 | 7578442 | p.Y163C | SNV | − | 5-15% | Detected |
| 17 | 7578449 | p.A161T | SNV | − | 5-15% | Detected |
| 17 | 7578461 | p.V157F | SNV | − | 5-15% | Detected |
| 17 | 7578526 | p.C135Y | SNV | − | 5-15% | Detected |
| 17 | 7578535 | p.K132R | SNV | − | 5-15% | Detected |
| 17 | 7578542 | p.L130V | SNV | − | 5-15% | Detected |
| 17 | 7578550 | p.S127F | SNV | − | 5-15% | Detected |
| 17 | 7579295 | p.? | SNV | − | 5-15% | Detected |
| 17 | 7579312 | p.T125T | SNV | − | 5-15% | Detected |
| 17 | 7579358 | p.R110L | SNV | − | 5-15% | Detected |
| 17 | 7579368 | p.Y107D | SNV | − | 5-15% | Detected |
| 17 | 7579414 | p.W91* | SNV | − | 5-15% | Detected |
| 17 | 7579442 | p.P82L | SNV | − | 5-15% | Detected |
| 17 | 7579472 | p.R72P | SNV | − | genomic | Not Covered |
| 17 | 7579521 | p.E56* | SNV | − | 5-15% | Detected |
| 17 | 7579536 | p.E51* | SNV | − | 5-15% | Detected |
| 17 | 7579553 | p.L45P | SNV | − | 5-15% | Detected |
| 17 | 7579575 | p.Q38* | SNV | − | 5-15% | Detected |
| 17 | 7579715 | p.P27fs*17 | DEL | − | 5-15% | Detected |

| Chromosome | Position | CHPv2 Detection | TSACP Detection | TSTP Detection |
|---|---|---|---|---|
| 17 | 7577022 | Detected | Detected | Detected |
| 17 | 7577046 | Detected | Detected | Detected |
| 17 | 7577105 | Detected | Detected | Detected |
| 17 | 7577120 | Detected | Detected | Detected |
| 17 | 7577538 | Detected | Detected | Detected |
| 17 | 7577548 | Detected | Detected | Detected |
| 17 | 7577559 | Detected | Detected | Detected |
| 17 | 7577580 | Detected | Detected | Detected |
| 17 | 7578115 | Not Covered | Detected | Not Covered |
| 17 | 7578190 | Detected | Detected | Detected |

TABLE 9-continued

| | | | | |
|---|---|---|---|---|
| 17 | 7578196 | Detected | Detected | Detected |
| 17 | 7578203 | Detected | Detected | Detected |
| 17 | 7578235 | Detected | Detected | Detected |
| 17 | 7578388 | Detected | Detected | Detected |
| 17 | 7578442 | Detected | Detected | Detected |
| 17 | 7578449 | Detected | Detected | Detected |
| 17 | 7578461 | Detected | Detected | Detected |
| 17 | 7578526 | Detected | Detected | Detected |
| 17 | 7578535 | Detected | Detected | Detected |
| 17 | 7578542 | Detected | Detected | Detected |
| 17 | 7578550 | Detected | Detected | Detected |
| 17 | 7579295 | Not Covered | Not Covered | Not Detected |
| 17 | 7579312 | Not Covered | Not Covered | Detected |
| 17 | 7579358 | Detected | Detected | Detected |
| 17 | 7579368 | Detected | Detected | Detected |
| 17 | 7579414 | Detected | Detected | Detected |
| 17 | 7579442 | Detected | Detected | Detected |
| 17 | 7579472 | Detected | Detected | Detected |
| 17 | 7579521 | Not Covered | Not Covered | Detected |
| 17 | 7579536 | Not Covered | Not Covered | Detected |
| 17 | 7579553 | Not Covered | Not Covered | Detected |
| 17 | 7579575 | Not Covered | Not Covered | Detected |
| 17 | 7579715 | Not Covered | Not Covered | Detected |

| Chromosome | Position | Reference |
|---|---|---|
| 17 | 7579801 | G |
| 17 | 37880220 | T |
| 17 | 37880261 | G |
| 17 | 37880981 | A |
| 17 | 37881332 | G |
| 17 | 37881378 | A |
| 17 | 37881440 | C |
| 18 | 48575112 | T |
| 18 | 48575183 | T |
| 18 | 48575195 | C |
| 18 | 48575209 | C |
| 18 | 48575671 | C |
| 18 | 48581198 | G |
| 18 | 48581229 | C |
| 18 | 48581243 | C |
| 18 | 48584560 | C |

TABLE 9-continued

| Chromosome | Position | Alternate |
|---|---|---|
| 18 | 48584593 | C |
| 18 | 48584602 | ACT |
| 18 | 48586262 | C |
| 18 | 48586291 | G |
| 18 | 48591838 | A |
| 18 | 48591847 | A |
| 18 | 48591855 | A |
| 18 | 48591865 | C |
| 18 | 48593405 | G |
| 18 | 48593465 | G |
| 18 | 48593475 | T |
| 18 | 48593495 | A |
| 18 | 48603032 | C |
| 18 | 48604682 | A |
| 18 | 48604697 | A |
| 18 | 48604754 | G |
| 18 | 48604769 | C |

| Chromosome | Position | Alternate |
|---|---|---|
| 17 | 7579801 | C |
| 17 | 37880220 | C |
| 17 | 37880261 | T |
| 17 | 37880981 | AGCATACGTGATG (SEQ ID NO: 33) |
| 17 | 37881332 | A |
| 17 | 37881378 | G |
| 17 | 37881440 | T |
| 18 | 48575112 | C |
| 18 | 48575183 | C |
| 18 | 48575195 | T |
| 18 | 48575209 | T |
| 18 | 48575671 | G |
| 18 | 48581198 | T |
| 18 | 48581229 | A |
| 18 | 48581243 | T |
| 18 | 48584560 | T |
| 18 | 48584593 | T |
| 18 | 48584602 | A |
| 18 | 48586262 | T |
| 18 | 48586291 | C |
| 18 | 48591838 | G |
| 18 | 48591847 | G |

TABLE 9-continued

| | | |
|---|---|---|
| 18 | 48591855 | G |
| 18 | 48591865 | G |
| 18 | 48593405 | C |
| 18 | 48593465 | A |
| 18 | 48593475 | TAC |
| 18 | 48593495 | G |
| 18 | 48603032 | T |
| 18 | 48604682 | G |
| 18 | 48604697 | G |
| 18 | 48604754 | T |
| 18 | 48604769 | A |

| Chromosome | Position | Length | Mutation ID | Gene |
|---|---|---|---|---|
| 17 | 7579801 | 1 | gDNA35 | TP53 |
| 17 | 37880220 | 1 | COSM14060 | ERBB2 |
| 17 | 37880261 | 1 | COSM1251412 | ERBB2 |
| 17 | 37880981 | 12 | COSM20959 | ERBB2 |
| 17 | 37881332 | 1 | COSM14065 | ERBB2 |
| 17 | 37881378 | 1 | COSM686 | ERBB2 |
| 17 | 37881440 | 1 | COSM21985 | ERBB2 |
| 18 | 48575112 | 1 | COSM1389031 | SMAD4 |
| 18 | 48575183 | 1 | COSM14229 | SMAD4 |
| 18 | 48575195 | 1 | COSM218557 | SMAD4 |
| 18 | 48575209 | 1 | COSM14168 | SMAD4 |
| 18 | 48575671 | 1 | COSM13115 | SMAD4 |
| 18 | 48581198 | 1 | COSM14118 | SMAD4 |
| 18 | 48581229 | 1 | COSM1226725 | SMAD4 |
| 18 | 48581243 | 1 | COSM308153 | SMAD4 |
| 18 | 48584560 | 1 | COSM14057 | SMAD4 |
| 18 | 48584593 | 1 | COSM22901 | SMAD4 |
| 18 | 48584602 | 2 | COSM14217 | SMAD4 |
| 18 | 48586262 | 1 | COSM14163 | SMAD4 |
| 18 | 48586291 | 1 | COSM14167 | SMAD4 |
| 18 | 48591838 | 1 | COSM1389054 | SMAD4 |
| 18 | 48591847 | 1 | COSM1389057 | SMAD4 |
| 18 | 48591855 | 1 | COSM14109 | SMAD4 |
| 18 | 48591865 | 1 | COSM14111 | SMAD4 |
| 18 | 48593405 | 1 | COSM14249 | SMAD4 |
| 18 | 48593465 | 1 | COSM14103 | SMAD4 |
| 18 | 48593475 | 2 | COSM14223 | SMAD4 |
| 18 | 48593495 | 1 | AMXsynt12 | SMAD4 |

TABLE 9-continued

| | | | | |
|---|---|---|---|---|
| 18 | 48603032 | 1 | COSM14096 | SMAD4 |
| 18 | 48604682 | 1 | COSM14114 | SMAD4 |
| 18 | 48604697 | 1 | COSM1389099 | SMAD4 |
| 18 | 48604754 | 1 | COSM14134 | SMAD4 |
| 18 | 48604769 | 1 | COSM1389106 | SMAD4 |

| Chromosome | Position | Mutation CDS |
|---|---|---|
| 17 | 7579801 | c.74 + 38C > G |
| 17 | 37880220 | c.2264T > C |
| 17 | 37880261 | c.2305G > T |
| 17 | 37880981 | c.2324_2325ins12 |
| 17 | 37881332 | c.2524G > A |
| 17 | 37881378 | c.2570A > G |
| 17 | 37881440 | c.2632C > T |
| 18 | 48575112 | c.306T > C |
| 18 | 48575183 | c.377T > C |
| 18 | 48575195 | c.389C > T |
| 18 | 48575209 | c.403C > T |
| 18 | 48575671 | c.431C > G |
| 18 | 48581198 | c.502G > T |
| 18 | 48581229 | c.533C > A |
| 18 | 48581243 | c.547C > T |
| 18 | 48584560 | c.733C > T |
| 18 | 48584593 | c.766C > T |
| 18 | 48584602 | c.776_777delCT |
| 18 | 48586262 | c.931C > T |
| 18 | 48586291 | c.955 + 5G > C |
| 18 | 48591838 | c.1001A > G |
| 18 | 48591847 | c.1010A > G |
| 18 | 48591855 | c.1018A > G |
| 18 | 48591865 | c.1028C > G |
| 18 | 48593405 | c.1156G > C |
| 18 | 48593465 | c.1216G > A |
| 18 | 48593475 | c.1229_1230insCA |
| 18 | 48593495 | c.1246A > G |
| 18 | 48603032 | c.1333C > T |
| 18 | 48604682 | c.1504A > G |
| 18 | 48604697 | c.1519A > G |
| 18 | 48604754 | c.1576G > T |
| 18 | 48604769 | c.1591C > A |

TABLE 9-continued

| Chromosome | Position | Mutation AA | Mutation Type | Strand | Target Frequency | Sanger Detection* |
|---|---|---|---|---|---|---|
| 17 | 7579801 | p.(=) | SNV | − | genomic | Not Covered |
| 17 | 37880220 | p.L755S | SNV | + | 5-15% | Detected |
| 17 | 37880261 | p.D769Y | SNV | + | 5-15% | Detected |
| 17 | 37880981 | p.A775_G776insYVMA | INS | + | 5-15% | Detected |
| 17 | 37881332 | p.V842I | SNV | + | 5-15% | Detected |
| 17 | 37881378 | p.N857S | SNV | + | 5-15% | Detected |
| 17 | 37881440 | p.H878Y | SNV | + | 5-15% | Detected |
| 18 | 48575112 | p.P102P | SNV | + | 5-15% | Detected |
| 18 | 48575183 | p.V126A | SNV | + | 5-15% | Detected |
| 18 | 48575195 | p.P130L | SNV | + | 5-15% | Detected |
| 18 | 48575209 | p.R135* | SNV | + | 5-15% | Detected |
| 18 | 48575671 | p.S144* | SNV | + | 5-15% | Detected |
| 18 | 48581198 | p.G168* | SNV | + | 5-15% | Detected |
| 18 | 48581229 | p.S178* | SNV | + | 5-15% | Detected |
| 18 | 48581243 | p.Q183* | SNV | + | 5-15% | Detected |
| 18 | 48584560 | p.Q245* | SNV | + | 5-15% | Detected |
| 18 | 48584593 | p.Q256* | SNV | + | 5-15% | Detected |
| 18 | 48584602 | p.T259fs*4 | DEL | + | 5-15% | Detected |
| 18 | 48586262 | p.Q311* | SNV | + | 5-15% | Detected |
| 18 | 48586291 | p.? | SNV | + | 5-15% | Detected |
| 18 | 48591838 | p.Q334R | SNV | + | 5-15% | Detected |
| 18 | 48591847 | p.E337G | SNV | + | 5-15% | Detected |
| 18 | 48591855 | p.K340E | SNV | + | 5-15% | Detected |
| 18 | 48591865 | p.S343* | SNV | + | 5-15% | Detected |
| 18 | 48593405 | p.G386R | SNV | + | 5-15% | Detected |
| 18 | 48593465 | p.A406T | SNV | + | 5-15% | Detected |
| 18 | 48593475 | p.Q410fs*6 | INS | + | 5-15% | Detected |
| 18 | 48593495 | p.R416G | SNV | + | 5-15% | Detected |
| 18 | 48603032 | p.R445* | SNV | + | 5-15% | Detected |
| 18 | 48604682 | p.R502G | SNV | + | 5-15% | Detected |
| 18 | 48604697 | p.K507E | SNV | + | 5-15% | Detected |
| 18 | 48604754 | p.E526* | SNV | + | 5-15% | Detected |
| 18 | 48604769 | p.R531R | SNV | + | 5-15% | Detected |

| Chromosome | Position | CHPv2 Detection | TSACP Detection | TSTP Detection |
|---|---|---|---|---|
| 17 | 7579801 | Not Covered | Not Covered | Detected |
| 17 | 37880220 | Detected | Detected | Not Covered |
| 17 | 37880261 | Detected | Detected | Not Covered |
| 17 | 37880981 | Detected | Not Covered | Detected |

TABLE 9-continued

| | | | | |
|---|---|---|---|---|
| 17 | 37881332 | Detected | Not Detected | Not Covered |
| 17 | 37881378 | Detected | Detected | Not Covered |
| 17 | 37881440 | Detected | Detected | Not Covered |
| 18 | 48575112 | Detected | Not Covered | Not Covered |
| 18 | 48575183 | Detected | Detected | Not Covered |
| 18 | 48575195 | Detected | Detected | Not Covered |
| 18 | 48575209 | Detected | Detected | Not Covered |
| 18 | 48575671 | Detected | Not Covered | Not Covered |
| 18 | 48581198 | Detected | Detected | Not Covered |
| 18 | 48581229 | Detected | Detected | Not Covered |
| 18 | 48581243 | Detected | Detected | Not Covered |
| 18 | 48584560 | Detected | Detected | Not Covered |
| 18 | 48584593 | Detected | Detected | Not Covered |
| 18 | 48584602 | Detected | Detected | Not Covered |
| 18 | 48586262 | Detected | Detected | Not Covered |
| 18 | 48586291 | Detected | Detected | Not Covered |
| 18 | 48591838 | Detected | Detected | Detected |
| 18 | 48591847 | Detected | Detected | Detected |
| 18 | 48591855 | Detected | Detected | Detected |
| 18 | 48591865 | Detected | Detected | Detected |
| 18 | 48593405 | Detected | Detected | Not Covered |
| 18 | 48593465 | Detected | Detected | Not Covered |
| 18 | 48593475 | Detected | Detected | Not Covered |
| 18 | 48593495 | Detected | Detected | Not Covered |
| 18 | 48603032 | Detected | Detected | Not Covered |
| 18 | 48604682 | Detected | Detected | Detected |
| 18 | 48604697 | Detected | Detected | Detected |
| 18 | 48604754 | Detected | Detected | Detected |
| 18 | 48604769 | Detected | Detected | Detected |

| Chromosome | Position | Reference |
|---|---|---|
| 19 | 1207076 | TG |
| 19 | 1220321 | T |
| 19 | 1220371 | G |
| 19 | 1220382 | C |
| 19 | 1220487 | G |
| 19 | 1220502 | G |
| 19 | 1221293 | C |
| 19 | 1221319 | C |
| 19 | 1223125 | C |
| 19 | 3115012 | C |

TABLE 9-continued

| | | |
|---|---|---|
| 19 | 3118942 | A |
| 19 | 3119239 | C |
| 19 | 17945696 | C |
| 19 | 17948009 | G |
| 20 | 36031631 | C |
| 20 | 57480494 | C |
| 20 | 57484420 | C |
| 20 | 57484596 | A |
| 22 | 24133967 | C |
| 22 | 24133990 | C |
| 22 | 24134006 | C |
| 22 | 24143240 | C |
| 22 | 24145528 | C |
| 22 | 24145582 | C |
| 22 | 24145588 | G |
| 22 | 24145675 | G |
| 22 | 24176353 | GC |

| Chromosome | Position | Alternate |
|---|---|---|
| 19 | 1207076 | T |
| 19 | 1220321 | C |
| 19 | 1220371 | T |
| 19 | 1220382 | T |
| 19 | 1220487 | T |
| 19 | 1220502 | T |
| 19 | 1221293 | T |
| 19 | 1221319 | T |
| 19 | 1223125 | G |
| 19 | 3115012 | T |
| 19 | 3118942 | T |
| 19 | 3119239 | T |
| 19 | 17945696 | T |
| 19 | 17948009 | A |
| 20 | 36031631 | T |
| 20 | 57480494 | T |
| 20 | 57484420 | T |
| 20 | 57484596 | T |
| 22 | 24133967 | T |
| 22 | 24133990 | A |
| 22 | 24134006 | T |
| 22 | 24143240 | T |

TABLE 9-continued

| | | | | |
|---|---|---|---|---|
| 22 | 24145528 | CCCGAGGTGCTGGTCCCCAT (SEQ ID NO: 34) | | |
| 22 | 24145582 | T | | |
| 22 | 24145588 | A | | |
| 22 | 24145675 | C | | |
| 22 | 24176353 | G | | |

| Chromosome | Position | Length | Mutation ID | Gene |
|---|---|---|---|---|
| 19 | 1207076 | 1 | COSM21212 | STK11 |
| 19 | 1220321 | 1 | gDNA27 | STK11 |
| 19 | 1220371 | 1 | COSM21570 | STK11 |
| 19 | 1220382 | 1 | COSM27316 | STK11 |
| 19 | 1220487 | 1 | COSM20944 | STK11 |
| 19 | 1220502 | 1 | COSM25229 | STK11 |
| 19 | 1221293 | 1 | COSM29005 | STK11 |
| 19 | 1221319 | 1 | COSM21355 | STK11 |
| 19 | 1223125 | 1 | COSM21360 | STK11 |
| 19 | 3115012 | 1 | COSM21651 | GNA11 |
| 19 | 3118942 | 1 | COSM52969 | GNA11 |
| 19 | 3119239 | 1 | gDNA28 | GNA11 |
| 19 | 17945696 | 1 | COSM34213 | JAK3 |
| 19 | 17948009 | 1 | COSM34214 | JAK3 |
| 20 | 36031631 | 1 | COSM1227526 | SRC |
| 20 | 57480494 | 1 | COSM244725 | GNAS |
| 20 | 57484420 | 1 | COSM27887 | GNAS |
| 20 | 57484596 | 1 | COSM27888 | GNAS |
| 22 | 24133967 | 1 | COSM1002 | SMARCB1 |
| 22 | 24133990 | 1 | COSM991 | SMARCB1 |
| 22 | 24134006 | 1 | COSM24595 | SMARCB1 |
| 22 | 24143240 | 1 | COSM992 | SMARCB1 |
| 22 | 24145528 | 19 | COSM51386 | SMARCB1 |
| 22 | 24145582 | 1 | COSM993 | SMARCB1 |
| 22 | 24145588 | 1 | COSM999 | SMARCB1 |
| 22 | 24145675 | 1 | gDNA30 | SMARCB1 |
| 22 | 24176353 | 1 | COSM1057 | SMARCB1 |

| Chromosome | Position | Mutation CDS |
|---|---|---|
| 19 | 1207076 | c.169delG |
| 19 | 1220321 | c.465 − 51T > C |
| 19 | 1220371 | c.465 − 1G > T |
| 19 | 1220382 | c.475C > T |
| 19 | 1220487 | c.580G > T |
| 19 | 1220502 | c.595G > T |

TABLE 9-continued

| Chromosome | Position | | | c. notation |
|---|---|---|---|---|
| 19 | 1221293 | | | c.816C > T |
| 19 | 1221319 | | | c.842C > T |
| 19 | 1223125 | | | c.1062C > G |
| 19 | 3115012 | | | c.547C > T |
| 19 | 3118942 | | | c.626A > T |
| 19 | 3119239 | | | c.771C > T |
| 19 | 17945696 | | | c.2164G > A |
| 19 | 17948009 | | | c.1715C > T |
| 20 | 36031631 | | | c.1460C > T |
| 20 | 57480494 | | | c.489C > T |
| 20 | 57484420 | | | c.601C > T |
| 20 | 57484596 | | | c.680A > T |
| 22 | 24133967 | | | c.118C > T |
| 22 | 24133990 | | | c.141C > A |
| 22 | 24134006 | | | c.157C > T |
| 22 | 24143240 | | | c.472C > T |
| 22 | 24145528 | | | c.566_567ins19 |
| 22 | 24145582 | | | c.601C > T |
| 22 | 24145588 | | | c.607G > A |
| 22 | 24145675 | | | c.601 + 66G > C |
| 22 | 24176353 | | | c.1148delC |

| Chromosome | Position | Mutation AA | Mutation Type | Strand | Target Frequency | Sanger Detection* |
|---|---|---|---|---|---|---|
| 19 | 1207076 | p.E57fs*7 | DEL | + | 5-15% | Detected |
| 19 | 1220321 | p.(=) | SNV | + | genomic | Not Covered |
| 19 | 1220371 | p.? | SNV | + | 5-15% | Detected |
| 19 | 1220382 | p.Q159* | SNV | + | 5-15% | Detected |
| 19 | 1220487 | p.D194Y | SNV | + | 5-15% | Detected |
| 19 | 1220502 | p.E199* | SNV | + | 5-15% | Detected |
| 19 | 1221293 | p.Y272Y | SNV | + | 5-15% | Detected |
| 19 | 1221319 | p.P281L | SNV | + | 5-15% | Detected |
| 19 | 1223125 | p.F354L | SNV | + | 5-15% | Detected |
| 19 | 3115012 | p.R183C | SNV | + | 5-15% | Detected |
| 19 | 3118942 | p.Q209L | SNV | + | 5-15% | Detected |
| 19 | 3119239 | p.T257T | SNV | + | genomic | Not Covered |
| 19 | 17945696 | p.V722I | SNV | − | 5-15% | Detected |
| 19 | 17948009 | p.A572V | SNV | − | 5-15% | Detected |
| 20 | 36031631 | p.P487L | SNV | + | 5-15% | Detected |
| 20 | 57480494 | p.Y163Y | SNV | + | 5-15% | Detected |
| 20 | 57484420 | p.R201C | SNV | + | 5-15% | Detected |
| 20 | 57484596 | p.Q227L | SNV | + | 5-15% | Detected |

TABLE 9-continued

| | | | | | | |
|---|---|---|---|---|---|---|
| 22 | 24133967 p.R40* | SNV | + | 5-15% | Detected |
| 22 | 24133990 p.Y47* | SNV | + | 5-15% | Detected |
| 22 | 24134006 p.R53* | SNV | + | 5-15% | Detected |
| 22 | 24143240 p.R158* | SNV | + | 5-15% | Detected |
| 22 | 24145528 p.L191fs*26 | INS | + | 5-15% | Detected |
| 22 | 24145582 p.R201* | SNV | + | 5-15% | Detected |
| 22 | 24145588 p.A203T | SNV | + | 5-15% | Detected |
| 22 | 24145675 p.(=) | SNV | + | genomic | Not Covered |
| 22 | 24176353 p.P383fs | DEL | + | 5-15% | Detected |

| Chromosome | Position | CHPv2 Detection | TSACP Detection | TSTP Detection |
|---|---|---|---|---|
| 19 | 1207076 | Detected | Detected | Detected |
| 19 | 1220321 | Detected | Not Covered | Detected |
| 19 | 1220371 | Detected | Not Covered | Detected |
| 19 | 1220382 | Detected | Not Covered | Detected |
| 19 | 1220487 | Detected | Detected | Not Covered |
| 19 | 1220502 | Detected | Detected | Not Covered |
| 19 | 1221293 | Detected | Detected | Detected |
| 19 | 1221319 | Detected | Detected | Detected |
| 19 | 1223125 | Detected | Detected | Detected |
| 19 | 3115012 | Not Covered | Detected | Not Covered |
| 19 | 3118942 | Detected | Detected | Not Covered |
| 19 | 3119239 | Not Covered | Detected | Not Covered |
| 19 | 17945696 | Detected | Detected | Not Covered |
| 19 | 17948009 | Detected | Detected | Not Covered |
| 20 | 36031631 | Not Covered | Not Covered | Detected |
| 20 | 57480494 | Not Covered | Not Covered | Detected |
| 20 | 57484420 | Detected | Detected | Detected |
| 20 | 57484596 | Detected | Not Covered | Not Covered |
| 22 | 24133967 | Detected | Detected | Not Covered |
| 22 | 24133990 | Detected | Detected | Not Covered |
| 22 | 24134006 | Detected | Detected | Not Covered |
| 22 | 24143240 | Detected | Detected | Not Covered |
| 22 | 24145528 | Not Detected | Not Covered | Not Covered |
| 22 | 24145582 | Detected | Detected | Not Covered |
| 22 | 24145588 | Detected | Detected | Not Covered |
| 22 | 24145675 | Not Covered | Detected | Not Covered |
| 22 | 24176353 | Detected | Detected | Not Covered |

What is claimed is:

1. A mixture of nucleic acid molecules comprising at least one reference sequence and at least 15 variants of the at least one reference sequence, wherein the nucleotide sequences of the at least one reference sequence and each variant are defined prior to forming the mixture, wherein each variant is at least 50% identical to the at least one reference sequence, and wherein the variants comprise at least one single nucleotide polymorphism (SNP), multiple nucleotide polymorphisms (MNP), an insertion, a deletion, a copy number variation, a gene fusion, a duplication, an inversion, a repeat polymorphism, a homopolymer of the at least one reference sequence, and/or a nonhuman sequence.

2. The mixture of nucleic acid molecules of claim 1, comprising at least 30 variants.

3. The mixture of nucleic acid molecules of claim 1, wherein each variant is related to cancer, an inherited disease, or an infectious disease.

4. The mixture of nucleic acid molecules of claim 1, wherein the nucleic acid sequence of each variant differs from its neighbor variant by a predetermined percentage of 10% or less.

5. The mixture of nucleic acid molecules of claim 1, wherein each variant comprises a homopolymer sequence of at least 3 nucleotides.

6. The mixture of nucleic acid molecules of claim 1, wherein each variant possesses a nucleic acid barcode.

7. The mixture of nucleic acid molecules of claim 1, wherein each variant comprises a subsequence of the at least one reference sequence.

8. The mixture of nucleic acid molecules of claim 1, wherein the at least one reference sequence is selected from MPL, NRAS, ALK, MSH6, IDH1, ERBB4, VHL, MLH1, CTNNB1, FOXL2, PIK3CA, FGFR3, PDGFRA, KIT, KDR, FBXW7, APC, CSF1R, NPM1, EGFR, MET, SMO, BRAF, EZH2, FGFR1, JAK2, CDKN2A, GNAQ, ABL1, NOTCH1, RET, PTEN, FGFR2, HRAS, ATM, KRAS, PTPN11, HNF1A, FLT3, RB1, AKT1, IDH2, CDH1, TP53, ERBB2, SMAD4, STK11, GNA11, JAK3, SRC, GNAS, and SMARCB1.

9. A composition comprising the mixture of nucleic acid molecules of claim 1, wherein each nucleic acid molecule is an oligonucleotide.

10. A composition comprising the mixture of nucleic acid molecules of claim 1, wherein each nucleic acid molecule is a plasmid.

11. The composition of claim 10, further comprising a cell wherein the plasmid is transfected into and/or mixed with the cell.

12. The composition of claim 11, wherein the composition is formalin-fixed-paraffin embedded (FFPE) to produce a FFPE sample.

13. A composition comprising the mixture of nucleic acid molecules of claim 1, wherein two or more of the nucleic acid molecules are on a single plasmid.

14. The composition of claim 13, further comprising a cell wherein the plasmid is transfected into and/or mixed with the cell.

15. The composition of claim 14, wherein the composition is formalin-fixed-paraffin embedded (FFPE) to produce a FFPE sample.

16. A frequency ladder comprising the mixture of nucleic acid molecules of claim 1, wherein the mixture is diluted to produce a plurality of variants at different frequencies.

17. A frequency ladder comprising the mixture of nucleic acid molecules of claim 1, wherein the mixture is diluted with the at least one reference sequence to produce a plurality of variants at different frequencies.

18. A formalin-fixed, paraffin embedded (FFPE) sample composition comprising a cell, and
  a plasmid, wherein the plasmid is transfected into and/or mixed with the cell, and wherein the plasmid is a mixture of nucleic acid molecules comprising at least one reference sequence and at least 15 variants of the at least one reference sequence,
  wherein the nucleotide sequences of the at least one reference sequence and each variant are defined prior to forming the mixture,
  wherein each variant is at least 50% identical to the at least one reference sequence, and
  wherein the variants comprise at least one single nucleotide polymorphism (SNP), multiple nucleotide polymorphisms (MNP), an insertion, a deletion, a copy number variation, a gene fusion, a duplication, an inversion, a repeat polymorphism, a homopolymer of the at least one reference sequence, and/or a nonhuman sequence.

* * * * *